United States Patent [19]

Ikunaka et al.

[11] Patent Number: 6,083,943
[45] Date of Patent: Jul. 4, 2000

[54] SUBSTITUTED AZAHETEROCYCLECARBOXYLIC ACID

[75] Inventors: Masaya Ikunaka; Yuji Shishido, both of Chita-gun; Masami Nakane, Nagoya, all of Japan

[73] Assignee: Pfizer Inc, New York, N.Y.

[21] Appl. No.: 09/280,403

[22] Filed: Mar. 19, 1999

Related U.S. Application Data

[62] Continuation of application No. 08/957,176, Oct. 24, 1997, abandoned, which is a continuation of application No. 08/617,896, filed as application No. PCT/JP94/01514, Sep. 13, 1994, abandoned.

[30] Foreign Application Priority Data

Sep. 17, 1993 [JP] Japan ................................. 5-255064

[51] Int. Cl.[7] .................. A61K 31/40; A61K 31/445; C07D 207/14; C07D 211/56
[52] U.S. Cl. ................. 514/230.5; 514/311; 514/326; 514/314; 514/317; 514/318; 514/319; 514/320; 514/321; 514/323; 514/324; 514/329; 544/105; 544/106; 546/153; 546/155; 546/157; 546/174; 546/194; 546/196; 546/197; 546/202; 546/205; 546/207; 546/209; 546/210; 546/213; 546/214; 546/223; 546/224
[58] Field of Search .................. 544/105, 106; 546/153, 155, 157, 174, 194, 196, 197, 202, 205, 207, 209, 210, 213, 214, 223, 224; 514/230.5, 311, 326, 314, 329, 317, 318, 319, 320, 321, 323, 324

[56] References Cited

U.S. PATENT DOCUMENTS 5,232,929  8/1993  Desai et al. .............................. 514/314

FOREIGN PATENT DOCUMENTS 0610021  8/1994  European Pat. Off. .
WO9109844  7/1991  WIPO .
WO9210476  6/1992  WIPO .
WO9220676  11/1992  WIPO .
WO9300331  1/1993  WIPO .
WO9319064  9/1993  WIPO .
WO9410170  5/1994  WIPO .

*Primary Examiner*—Richard L. Raymond
*Assistant Examiner*—Bruck Kifle
*Attorney, Agent, or Firm*—Peter C. Richardson; Paul H. Ginsburg

[57] ABSTRACT

A compound of the chemical formula (I) and its pharmaceutically acceptable salt:

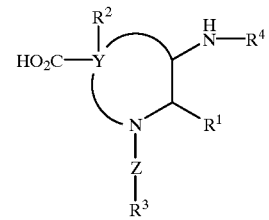

I wherein Y is $C_2$–$C_4$ alkylene; Z is a valence bond or $C_1$–$C_6$ alkylene; $R^1$ is substituted or unsubstituted aryl (e.g., phenyl and naphthyl) or heteroaryl (e.g., thienyl and furyl); $R^2$ is hydrogen or $C_1$–$C_6$ alkyl; $R^3$ is hydrogen, hydroxy or the like; $R^4$ is substituted or unsubstituted benzyl or the like. Typical examples are (2S*,3S*,4R*,5R*)-4-Carboxy-3-[N-(5-Isopropyl-2-methoxy-benzyl)amino]-5-methyl-2-phenylpyrrolidine and (2S*,3S*,5S*)-5-Carboxy-3-[N-(2-methoxy-5-trifluoromethoxybenzyl)amino]-2-phenylpiperidine. The novel substituted azaheterocyclecarboxylic acids in this invention have excellent substance P antagonistic activity and are thus useful for the treatment of gastrointestinal disorders, central nervous system disorders, allergy, inflammatory diseases, asthma, pain, emesis or migraine in mammals, especially humans.

12 Claims, No Drawings

SUBSTITUTED AZAHETEROCYCLECARBOXYLIC ACID

This is a continuation of U.S. Ser. No. 08/957,176, filed Oct. 24, 1997, abandoned, which was a continuation of U.S. Ser. No. 617,896, filed Mar. 13, 1996, abandoned, which was filed under 35 USC 371 from PCT/JP94/01514, filed on Sep. 13, 1994.

TECHNICAL FIELD

This invention relates to novel and useful substituted azaheterocyclecarboxylic acids of interest to those in the field of medical chemistry and chemotherapy. More particularly, it is concerned with a novel series of substituted azaheterocyclecarboxylic acids, including their pharmaceutically acceptable salts, which are of special value in view of their ability to antagonize substance P. In this way, these compounds are of use in treating gastrointestinal disorders, central nervous system disorders, inflammatory diseases, asthma, pain, migraine and emesis.

BACKGROUND ART

Substance P is a naturally occurring undecapeptide belonging to the tachykinin family of peptides, the latter being so-named because of their prompt stimulatory action on smooth muscle tissue. More specially, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine, as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc.

It is reported that the tachykinin antagonists are useful for allergic conditions, immunoregulation, vasodilation, bronchospasm, reflex or neuronal control of the viscera and senile dementia of the Alzheimer type and for the treatment of emesis and sunburn.

In the recent past, some attempts to develop the tachykinin antagonist such as the one against substance P have been carried out for the purpose of the treatment of the above disorders or diseases.

WO 91/09844 and WO 93/0031 disclose a wide variety of azaheterocyclic compounds as tachykinin antagonists such as substance P antagonists. However, none of the azaheterocyclic compounds disclosed in these references has a carboxy group on the azaheterocyclic ring.

Under the circumstances, the present inventors have worked to prepare compounds useful as substance P antagonist, and after extensive research, have succeeded in synthesizing a series of compounds as will be disclosed in detail herein.

The purpose of the present invention is to provide the novel substituted azaheterocyclecarboxylic acid with substance P antagonistic activity. In addition, the purpose of the invention is also to provide the pharmaceutical composition, which includes the substituted azaheterocyclecarboxylic acid as an active ingredient, for treating of gastrointestinal disorders, central nervous system disorders, allergy, inflammatory diseases, asthma, pain, migraine or emesis in mammalia, especially human.

BRIEF DESCRIPTION OF THE INVENTION

The present invention provides novel substituted azaheterocyclecarboxylic acids of the following chemical formula (I) and its pharmaceutically acceptable salt.

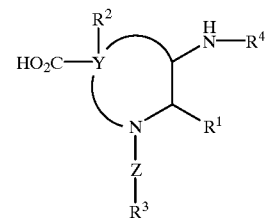

I wherein

Y is $C_2$–$C_4$ alkylene;

Z is a valence bond or $C_1$–$C_6$ alkylene;

$R^1$ is phenyl, biphenyl, indanyl, naphthyl, thienyl, furyl, pyridyl, thiazolyl, isothiazolyl, oxazolyl, isoxazolyl, tetrazolyl, quinolyl, phenyl $C_1$–$C_6$ alky- or benzhydryl, wherein each of the ring moieties may optionally be substituted by one or more substituents independently selected from halogen, $C_1$–$C_6$ alkyl, halosubstituted $C_1$–$C_6$ alkyl, $C_1$–$C_6$ alkoxy and halosubstituted $C_1$–$C_6$ alkoxy;

$R^2$ is hydrogen or $C_1$–$C_6$ alkyl;

$R^3$ is hydrogen, hydroxy, cyano, amino or carboxy; and $R^4$ represents a group of the formula (II) or (III)

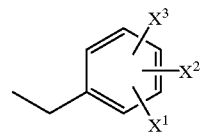

II

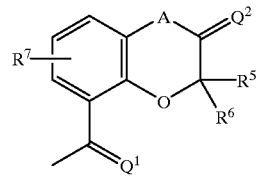

III wherein $X^1$, $X^2$ and $X^3$ are each halo, hydrogen, nitro, $C_1$–$C_6$ alkyl, halosubstituted $C_1$–$C_6$ alkyl, $C_1$–$C_6$ alkoxy, halosubstituted $C_1$–$C_6$ alkoxy, hydroxy, amino, $C_1$–$C_6$ alkylthio, $C_1$–$C_6$ alkylsulfinyl or $C_1$–$C_6$ alkylsulfonyl;

$Q^1$ and $Q^2$ are each $H_2$, oxygen or sulfur;

A is valence bond, methylene, oxygen, sulfur or NH;

$R^5$ and $R^6$ are each hydrogen or $C_1$–$C_6$ alkyl; and $R^7$ is hydrogen, halogen, $C_1$–$C_6$ alkyl, halosubstituted $C_1$–$C_6$ alkyl or $C_1$–$C_6$ alkoxy;

provided that when Z is a valence bond, $R^3$ must be hydrogen.

Also, the present invention provides a pharmaceutical composition for the treatment of gastrointestinal disorders, central nervous system disorders, allergy, inflammatory diseases, asthma, pain, migraine or emesis in a mammalian subject, which comprises a therapeutically effective amount of a compound of formula (I) or its pharmaceutically acceptable salt together with a pharmaceutically acceptable carrier.

Further, the present invention provides a method of treating or preventing gastrointestinal disorders, central nervous system disorders, allergy, inflammatory diseases, asthma, pain, migraine or emesisin a mammalian subject, which comprises administering to the said subject a therapeutically effective amount of a compound of formula (I) or its pharmaceutically acceptable salt.

DETAILED DESCRIPTION OF THE INVENTION

In this specification, the term "alkyl" is used herein to mean straight or branched hydrocarbon chain radicals including, but not limited to, methyl, ethyl, n-propyl, isopropyl, n-butyl, isobutyl, t-butyl, and the like;

the term "alkoxy" is used herein to mean —O-alkyl including, but not limited to, methoxy, ethoxy, propoxy, isopropoxy, n-butoxy, isobutoxy, t-butoxy and the like;

the term "halo" is used herein to mean fluorine, chlorine, bromine and iodine;

the term "halosubstituted alkyl" is used herein to mean an alkyl radical substituted with one or more halogens including, but not limited to, chloromethyl, trifluoromethyl, 2,2,2-trichloroethyl and the like; and the term "halosubstituted alkoxy" is used herein to mean an alkoxy radical substituted with one or more halogens including, but not limited to, chloromethoxy, trifluoromethoxy, 2,2,2-trichloroethoxy and the like.

The preferred values of Y are $CH_2CH_2$ (i.e., piperidine compounds) or $CH_2$ (i.e., pyrrolidine compounds), wherein the substituent —$CO_2H$ is at 5- or 4 position, respectively.

The preferred group for $R^1$ is phenyl, thienyl, fluorophenyl, chlorophenyl and bromophenyl, especially phenyl.

A particularly preferred sub-group of compounds of the invention consists of the compounds of formula I, wherein $R^4$ is formula (II), Y is ethylene or propylene, $R^1$ is phenyl, Z—$R^3$ is hydrogen and $R^2$ is attached to the carbon atom adjacent to the nitrogen of $NZR^3$. Especially preferred group for $R^2$ is hydrogen when Y is $CH_2CH_2$ and methyl when Y is $CH_2$.

Preferred individual compounds of this invention are the following:

(2S*,3S*,4S*,5R*)-4-carboxy-3-[N-(5-isopropyl-2-methoxy-benzyl)amino]-5-methyl-2-phenylpyrrolidine and (2S*,3S*,5S*)-5-carboxy-3-[N-(2-methoxy-5-trifluoromethoxybenzyl)amino]-2-phenylpiperidine.

The compounds of formula I form acid addition salts. The pharmaceutically acceptable acid addition salts are those formed from acids which form non-toxic acid salts.

The compounds of formula I may be prepared by a number of synthetic methods well known to those skilled in the art. Thus, the following routes 1 and 2 are available to prepare the objective compounds of the present invention.

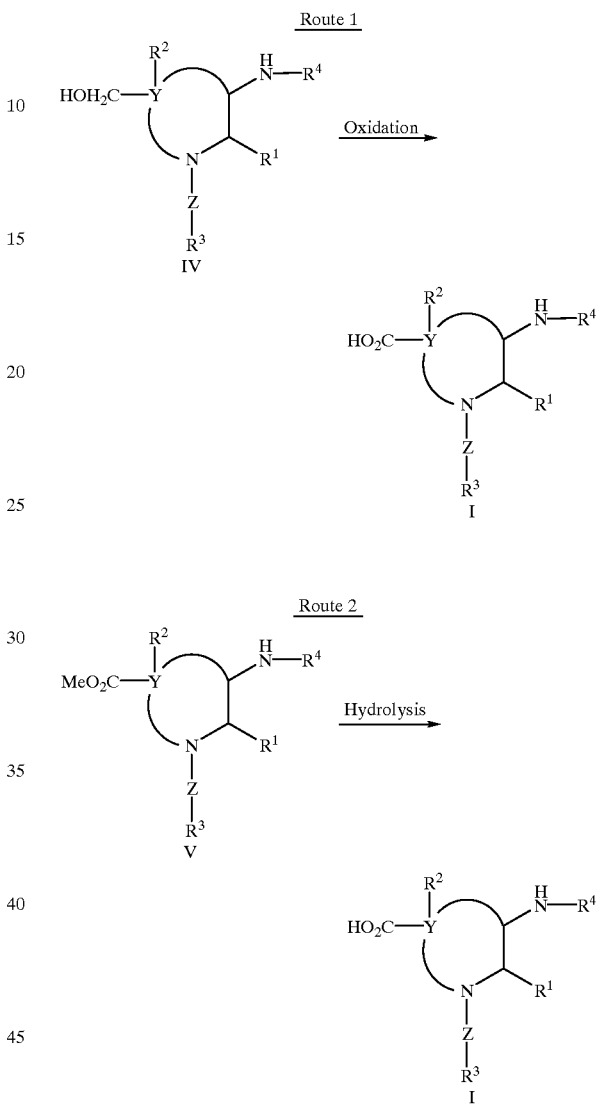

Route 1 is through the oxidation of an alchohol (IV). A lot of conditions which are well-known to those skilled in the art can be adopted for the oxidation. For example, reagents such as $KMnO_4$, $K_2CrO_4$, $K_2Cr_2O_7$ or enzymatic condition and the like can be used.

The second route 2 is through the hydrolysis of methyl ester (V). A lot of conditions which are well-known to those skilled in the art can be adopted for the hydrolysis. For example, acidic condition such as concentrated HCl at reflux temperature, alkaline condition, enzymatic condition and the like can be used.

Scheme 1
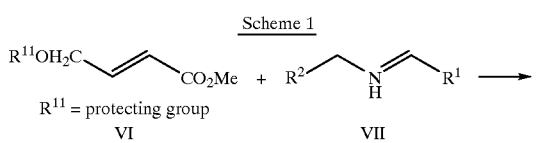
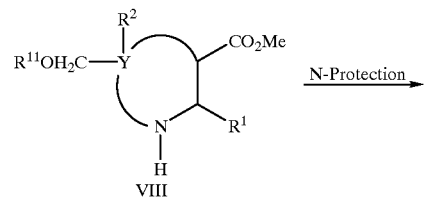
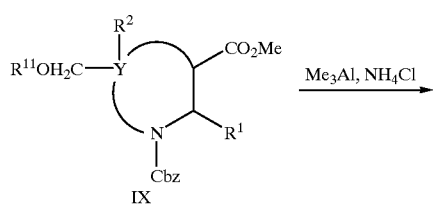
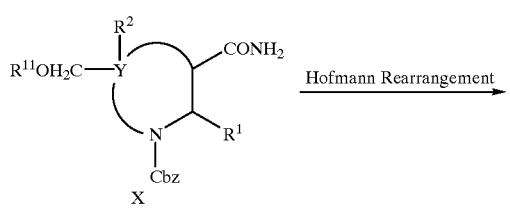
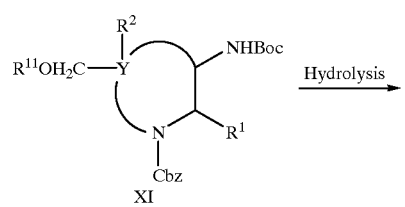
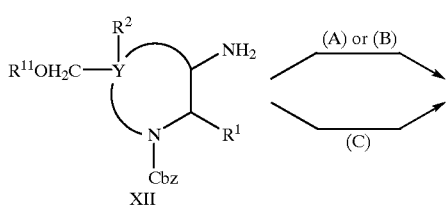
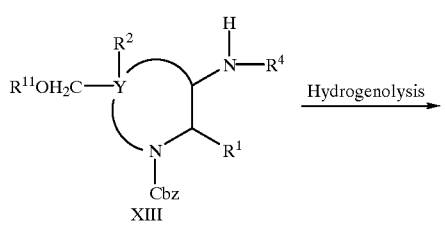
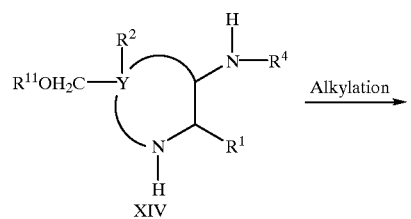
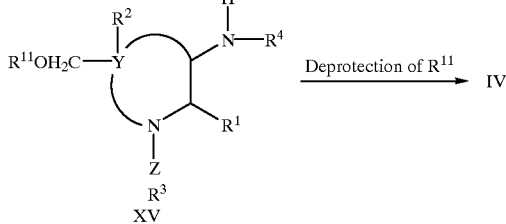
(A)
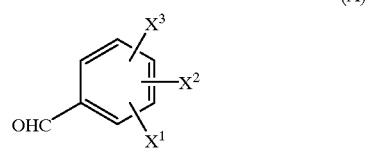
(B)
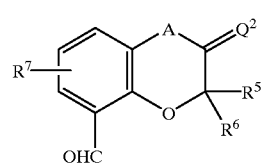
(C)
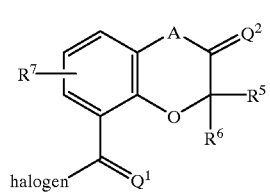
Scheme 2
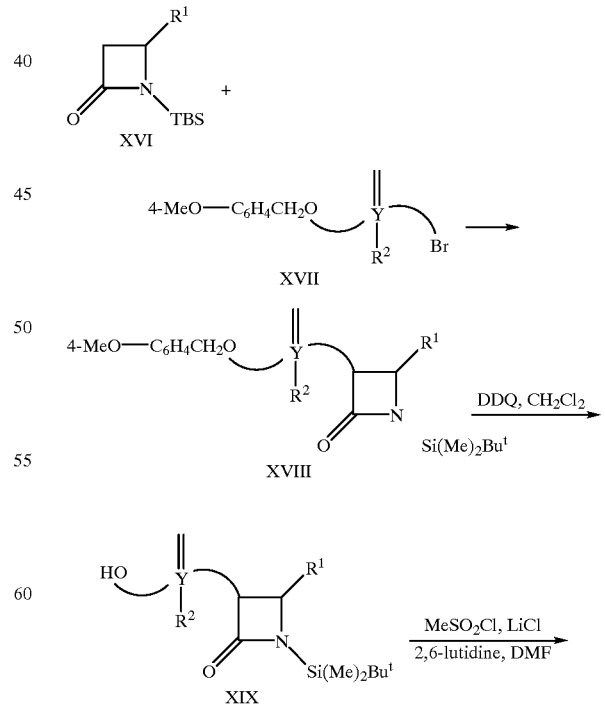

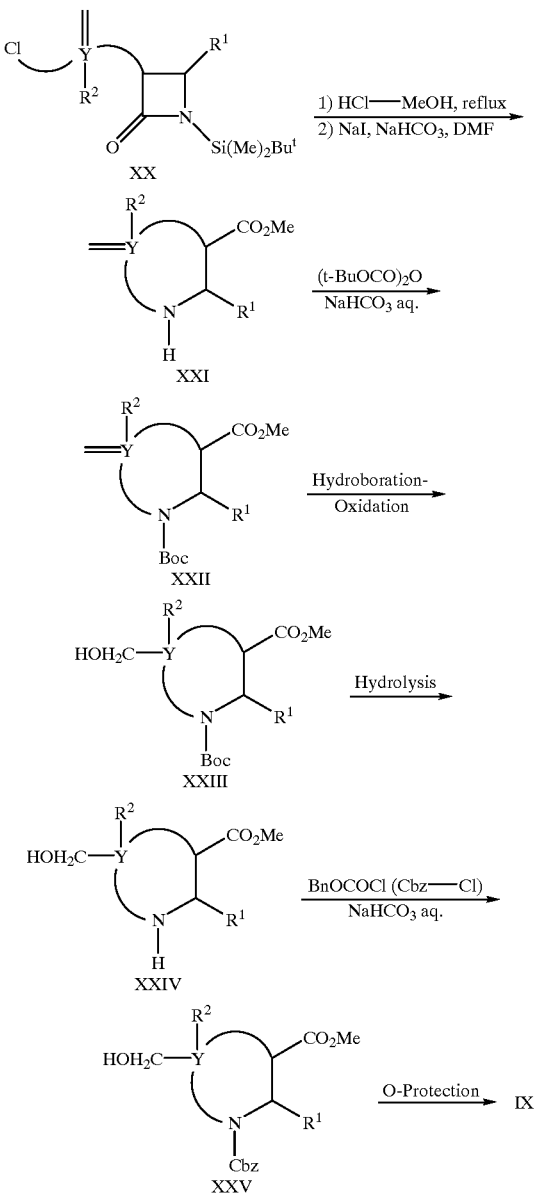

The starting material (IV) in route 1 can be synthesized according to the scheme 1.

The ring of the present invention can be synthesized by coupling of olefin (VI) with imine (VII) in the presence of a base in an inert solvent in the similar manner to the literature (J. Org. Chem., 53, 1384 (1988)). Preferred solvent is selected from tetrahydrofuran (THF), dioxane, dimethoxyethane (DME), toluene and the like. Preffered base is selected from triethylamine ($Et_3N$), 1,8-diazabicyclo[5,4,0]undec-7-ene (DBU) and the like. The preffered temperature is 0° C. to room temperature.

After N-protection of (VIII) by BnOCOCl (Cbz-Cl) in the presence of a base such as $NaHCO_3$ or $Et_3N$, the metoxycarbonyl side chain of (IX) is converted to amide by $Me_3Al$—$NH_4Cl$ in an inert solvent such as $CH_2Cl_2$ or benzene at room temperature to 100° C. Hoffmann rearrangement on (X) using $Pb(Ac)_4$—$^tBuOH$ gives (XI). Hydrolysis of (XI) is carried out by using cHCl—AcOEt, HCl—MeOH, $CF_3CO_2H$ and the like to give an amine (XII). The side chain $R^4$ is introduced by reductive alkylation with an aldehyde (A) or (B) in the presence of a reducing agent such as $NaBH_3CN$ or $NaBH(OAc)_3$ or by (thio)acylation using (C) in an inert solvent such as methanol (MeOH), $CH_2CH_2$ or $Cl(CH_2CH_2)Cl$.

(XIII) is then subjected to hydrogenolysis to give XIV. On introduction of —Z—R3 to XIV, R11 is deprotected from XV to give the satarting material (IV) in the route 1. The typical conditions for hydrogenolysis of (XIII) employs $H_2$ or $HCO_2NH_4$ in the presence of catalytic amount of Pd—C, $Pd(OH)_2$—C and the like in an inert solvent such as MeOH or ethanol (EtOH).

The introductions for —Z—$R^3$ can be carried out using an electrophile such as halogen-Z—$R^3$ in the presence of a base such as $Et_3N$, $KO^tBu$ in an inert solvent such as $CH_2CH_2$ or $Cl(CH_2CH_2)Cl$ at room temperature to 150° C.

The condition of deprotection of $R^{11}$ depends on the kind of the protecting group of $R^{11}$. For example, when $R^{11}$ is benzyl, catalytic hydrogenolysis $H_2$/Pd—C, $H_2$/$Pd(OH)_2$—C, Raney Ni and the like in an inert solvent such as methanol) or catalytic transfer hydrogenolysis ($HCO_2NH_4$ or $HCO_2H$ in the presence of catalytic amount of Pd—C, $Pd(OH)_2$—C and the like in an inert solvent such as methanol), and when $R^{11}$ is $Si(Me)_2{}^tBu$, $(nBu)_4NF$, $(nBu)_4NF$—AcOH, HF, AcOH and the like in an inert solvent such as THF or MeCN can be adopted.

An alternative route for synthesis of (IX) in Scheme 1 is shown in Scheme 2, which employs the β-lactam intermediates. The starting material (XVIII) is synthesized by coupling (XVI) with (XVII). This coupling reaction is carried out in the presence of a base such as $LiNEt_2$, $LiN^iPr_2$, $LiN(SiMe_3)_2$, or $NaN(SiMe_3)_2$ in an inert solvent such as THF, DME or $Et_2O$ at −100° C. to room temperature. In this reaction a co-solvent such as DMPU or HMPA can be used when it is needed. The beta-lactam (XVIII) is oxidatively deprotected, and the hydroxy group of (XIX) was substituted with Cl group. The β-lactam ring of (XX) was then converted to the ring of the present invention. The deprotection of 4-methoxybenzyl group in the step from (XVIII) to (XIX) is applied to the similar manner to the method described in Tetrahedron, 42, 3021 (1982), that is, DDQ in phosphate buffer (pH 7). In the presence of a base such as 2,6-lutidine in an inert solvent such as DMF, $MeSO_2Cl$—LiCl is convenient for chlorination of hydroxy group of (XIX) to (XX) as described in J. Org. Chem., 36, 3044 (1971). The conditions for the ring reorganization reaction from (XX) to (XXI) involves methanolysis with HCl—MeOH and treatment with NaI—$NaHCO_3$ in an inert solvent such as DMF at reflux temperature. After the NH group of the compound (XXI) is protected as a t-butyl carbamate using $(^tBuOCO)_2O$ in the presence of a base such as $NaHCO_3$ in an inert solvent system containing $H_2O$, the exomethylene group in (XXI) is subjected to hydroboration-oxidation to give (XXIII). The hydroborating agent can be selected from $BH_3$—$SMe_2$, $BH_3$—THF, 9-BBN (9-borabicyclo[3.3.1]nonane), thexylborane, disiamylborane, catecholborane and catalytic $(PPh_3)_3RhCl$ and the like in an inert solvent such as THF, DME, $Et_2O$ or diglyme at 0° C. to room temperature. The oxidizing reagent can be selected from 30% $H_2O_2$, triethylamine N-oxide, $NaBrO_3$ and the like.

The compound (XXIII) is then hydrolized in the similar manner to the step from (XI) to (XII), and (XXIV) is protected at NH group with Cbz-Cl in the similar manner to the step from (VIII) to (IX). The OH group of (XXV) is protected by $R^{11}$ to give (IX). When the $R^{11}$ group is $^tBu(Me)_2Si$—, $^tBu(Me)_2SiCl$ can be used in the presence of a base such as imidazol or $Et_3N$ in an inert solvent such as DMF or CH$_2$Cl$_2$ and when the R$^{11}$ croup is benzyl (Bn), BnOC(=NH)CCl$_3$—CF$_3$SO$_3$H can be employed in an inert solvent, especially CH$_2$Cl$_2$-cyclohexane(1:2).

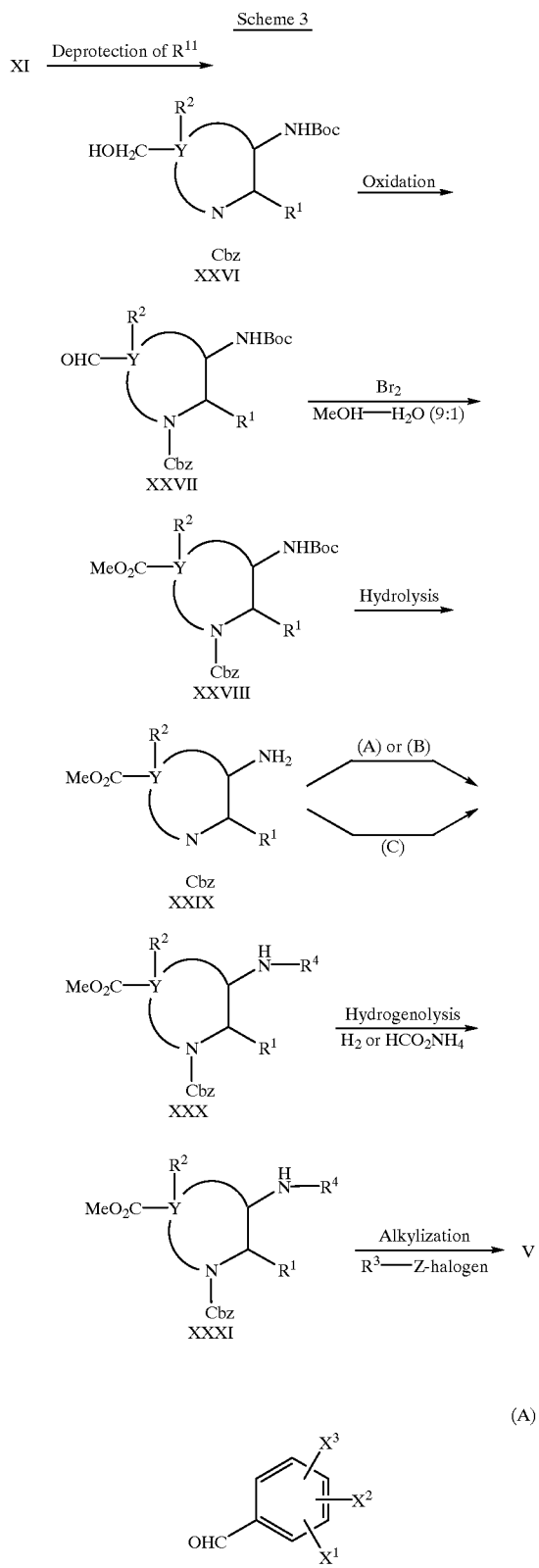

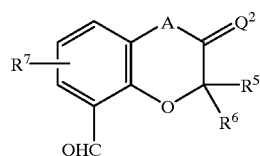

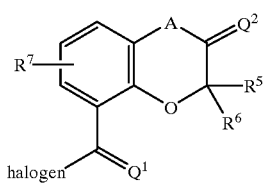

On the other hand, the starting material (V) in route 2 can be synthesized according to the Scheme 3. The compound (XI) described in scheme 1 is deprotected in the similar manner to the step from (XV) to (IV) in Scheme 1 to give the alchohol (XXVI). The alchohol (XXVI) is oxidized to aldehyde (XXVII), which is then subjected to oxidative esterification. PCC, PDC, SO$_3$.Py or (COCl)$_2$ can be used as a oxidant in an inert solvent such as CH$_2$Cl$_2$ or DMSO. A base such as Et$_3$N can be added to this oxidation reaction, if it is needed. In the coversion from aldehyde (XXVII) to ester (XXVIII), Br$_2$ in MeOH—H$_2$O (9:1) is employed satisfactorily. The deprotection of Boc group of (XXVIII) is carried out in the similar manner to the step from (XI) to (XII). The side chain R$^4$ is introduced to the resulting amine (XXIX) by the reaction with (A), (B) or (C) in the similar manner to the step from (XII) to (XIII). The Cbz group in the compound (XXX) is deprotected in the similar manner to the step from (XIII) to (XIV). Finally, —Z—R$^3$ can be introduced to XXXI in the similar manner to the step from (XIV) to (XV) to give the starting material (V) in route 2.

In case of preparing the substituted benzaldehyde (A) in Scheme 2 and Scheme 3, the standard methods (formylation of a substituted alkoxybenzene) well-known to those skilled in the art can be used according to the literatures as follows: (1) Duff's reaction (hexamethylenetetramine/TFA), *Synth. Commun.*, 15, 61 (1985), (2) TiCl$_4$/dichloromethylmethylether, *J. Org. Chem.*, 51, 4073 (1986), (3) A two step process involving chloromethylation (HCl, HCHO) and oxidation with 2-nitropropane and NaOMe), JP-58-501127 and (4) *J. Amer. Chem. Soc.*, 2466, (1955). Additionally, in order to prepare the substituted benzaldehyde, a Pd-catalyzed coupling reaction on halosubstituted alkoxybenzene in the following literature can be employed: (5) *Angew. Chem. Int. Ed. Engl.*, 25, 508 (1986), J. K. Stille et al., (6) *J. Org. Chem.*, 53 1170 (1988), J. K. Stille et al., (7) *Tetrahedron Lett.*, 4467 (1975), K. Sonogashira et al., (8) *Synthesis*, 627 (1980), N. Hagihara et al., The compounds (B) and (C) in scheme 2 and 3 can be synthesized according to the similar manner disclosed in WO 93/09116.

The reaction in the general synthesis is easily monitored by thin-layer chromatography (TLC). The reaction time is in general from a few minutes to several hours. The compounds can be isolated and purified by conventional procedures, such as recrystallisation or chromatography.

As the substituted azaheterocyclecarboxylic acids of formula I of this invention all possess several asymmetric centers, they are capable of existing in a variety of stereoisomeric forms or configurations. The present invention is meant to include all such forms within its scope. For instance, diastereomeric mixtures can be separated by methods well known to those skilled in the art, e.g., by fractional crystallization and the like, while racemic mixtures can be separated by standard resolution methods of organic chemistry.

Since all the substituted azaheterocyclecarboxylic acids of this invention are basic compounds, they are all capable of forming a wide variety of different salts with various inorganic and organic acids.

Although such salts must be pharmaceutically acceptable for administration to animals, it is often desirable in practice to initially isolate the substituted azaheterocyclecarboxylic acids from the reaction mixture as a pharmaceutically unacceptable salt and then simply convert to the free base compound by treatment with an alkaline reagent and thereafter, subsequently convert the free base to a pharmaceutically acceptable acid addition salt. The acid addition salts of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained.

The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts.

Substituted azaheterocyclecarboxylic acids of the invention which have also acidic groups are capable of forming base salts with various pharmaceutically acceptable cations. Examples of such salts include the alkali metal or alkaline-earth metal salts and particularly, the sodium and potassium salts. These salts are all prepared by conventional techniques.

The chemical bases which are used as reagents to prepare the pharmaceutically acceptable base salts of this invention are those which form non-toxic base salts with the substituted azaheterocyclecarboxylic acids herein described. These particular non-toxic base salts include those derived form such pharmaceutically acceptable cations as sodium, potassium, calcium and magnesium, etc. These salts can easily be prepared by treating the aforementioned substituted azaheterocyclecarboxylic acids with an aqueous solution containing the desired pharmaceutically acceptable cations, and then by evaporating the resulting solutions to dryness, preferably under reduced pressure. Alternatively, they may also be prepared by mixing lower alkanoic solutions of the acidic compounds and the suitable alkali metal alkoxide together, and then evaporating the resulting solution to dryness in the same manner as before. In either case, stoichiometric quantities of reagents are preferably employed in order to ensure completeness of reaction and production of the maximum yields of the desired final product.

The substituted azaheterocyclecarboxylic acids of the formula I exhibit significant substance P receptor-binding activity and therefore are of value in the treatment of a wide variety of clinical conditions in mammals which are characterized by the presence of an excess of said substance P activity. Such conditions include gastrointestinal disorders such as ulcer and colitis and other like diseases of the gastrointestinal tract; central nervous system disorders such as anxiety and psychosis; inflammatory diseases such as rheumatoid arthritis and inflammatory bowel diseases; respiratory diseases such as asthma; allergy; emesis; sunburn; urinary incontinence; angiogenesis; and pain, including migraine. Hence, these compounds are readily adapted to therapeutic use as substance P antagonists for the control and/or treatment of any of the aforesaid clinical conditions in mammals, including humans.

The radiolabelled substituted azaheterocyclecarboxylic acids of the formula (I) are useful as research and diagnostic tools in metabolism pharmacokinetic studies and in binding assays with the drug in both animal and human. Specific applications in research include radioligand binding assays, autoradiography studies and in vivo binding studies, while specific applications in the diagnostic area include studies of substance P receptor in the human brain, such as up/down regulation in a diseases state, and in vivo binding in the relevant tissues for inflammation, e.g., immune-type cell or cells that are directly involved in inflammatory bowel disorders and the like. Specifically, the radiolabelled forms of the substituted azaheterocyclecarboxylic acids are the tritium and $^{14}$C-isotope labelled substituted azaheterocyclecarboxylic acids in this invention.

The substituted azaheterocyclecarboxylic acids of formula (I) hereinbefore described can be administered to a mammalian subject, e.g., a human subject, via either the oral, parenteral or topical routes. In general, these compounds are typically administered to a human subject in doses ranging from about 1 mg to 300 mg per day. Variations will necessarily occur depending upon the weight and condition of the subject being treated, and the activity of the particular compound. However, a dosage level that is in the range from about 0.06 mg to about 6 mg per kg of body weight per day is most desirably employed for the treatment of inflammatory diseases or the like in a human subject. The compounds of the present invention may be administered alone or in combination with pharmaceutically acceptable carriers or diluents by any of the three routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in bovine caudate tissue or IM-9 cells employing radioactive ligands. The substance P antagonist activity of the substituted azaheterocyclecarboxylic acids described herein is evaluated by using the standard assay procedure described by M. A. Cascieri et al., as reported in the *Journal of Biological Chemistry*, 258, 5158 (1983). This method essentially involves determining the concentration of the individual compound required to reduce by 50% the amount of radiolabelled substance P ligands bound at their receptor sites in said isolated cow tissues or IM-9 cells, thereby affording characteristic $IC_{50}$ values for each compound tested. In this test, some preferred compounds indicated low $IC_{50}$ values of less than 1 nM with respect to inhibition of binding at its receptor.

Some compounds of the present invention, when tested as an antiinflammatory agent, exhibit a significant degree of activity in a capsaicin-induced plasma extravasation test [described by A. Nagahisa et al., European Journal of Pharmacology, 217, 191 (1992)].

In this test, antiinflammatory activity is determined as the percent inhibition of plasma protein extravasation in the ureter of male Hartley quinea pigs (weighing 300–350 g) in response to the intraperitoneal injection of capsaicin into anesthetized animals. The compounds of the present invention are dissolved in 0.1% methyl cellulose/water and dosed orally 1 h before capsaicin challenge. Evans Blue dye (30 mg/kg) is administered intravenously 5 min before capsaicin challenge. The animals are killed 10 min after capsaicin injection and both right and left ureters are removed. The Evans Blue dye is extracted and determined colorimetrically.

The anti-psychotic activity of the compounds of the present invention as neuroleptic agents for the control of various psychotic disorders is determined primarily by a study of their ability to suppress substance P-induced hypermotility in rats. This study is carried out by first dosing the rats with a control compound or with an appropriate test compound of the present invention, then injecting the rats with substance P by intracerebral administration via canula and thereafter measuring their individual locomotor response to the said stimuli.

In the above capsaicin-induced plasma extravasation test and anti-psychotic tests, compounds are considered active if the difference in response between the drug-treated animals and a control group receiving the vehicle alone is statistically significant.

EXAMPLES

The present invention is illustrated by the following examples. However, it should be understood that the invention is not limited to the specific details of these examples. Melting points were taken with a Yanako micro melting point apparatus and uncorrected. Infrared ray absorption spectra (IR) were measured by a Shimazu infrared spectrometer (IR-470). The peak shapes are denoted as follows: vs, very strong; s, strong; m, medium; w, weak. Proton nuclear magnetic resonance spectra (NMR) were measured in $CDCl_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Example 1

(1) (2R*,3S*,4S*,5S*)-4-Benzyloxymethyl-3,5-bis (methoxycarbon-yl)-2-phenylpyrrolidine To a stirred suspension of glycine methyl ester hydrochloride (11.8 g, 94.2 mmol) in EtOH (80 ml) was added $Et_3N$ (13.1 ml, d0.726, 94.2 mmol) at room temperature. To this heterogeneous mixture was added a solution of benzaldehyde (10.0 g, 94.2 mmol) in EtOH (20 ml) dropwise at room temperature. At the end of the addition turbidity of the reaction mixture decreased to a considerable extent. After stirring at room temperature for 2 hours, the solvent EtOH was evaporated in vacuo. To the residue was added half sat. NaCl aq. solution (20 ml), and the mixture was extracted with AcOEt (80 ml ×1). The AcOEt solution was washed with sat. NaCl aq. solution (×1), dried ($Na_2SO_4$), and concentrated in vacuo to give crude N-benzylidene glycine methyl ester (15.5 g, 93%). To a stirred mixture of freshly prepared crude N-benzylidene glycine methyl ester (15.5 g, 87.5 mmol), anhydrous LiBr (11.4 g, 131 mmol), and molecular sieves 4A (activated powder, Aldrich, 20.0 g) in dry THF (160 ml) was added a solution of 1,8-diazabicyclo [5.4.0]undec-7-ene (DBU, 16.0 g, 105 mmol) in dry THF (20.0 ml) dropwise with cooling in a dry ice-acetone bath under an atmosphere of $N_2$. To the resulting orange reaction mixture was added a solution of methyl (E)-4-benzyloxybutenoate (15.7 g, 76.1 mmol, known compound in the literatures: (a) Villieras, J.; Rambaud, M.; Graff, M.; *Tetrahedron Lett.*, 26, 53 (1985), (b) Villieras, J.; Rambaud, M.; *Synthesis* 300 (1983) and (c) Solladi, G.; Frechou, C.; Hutt, J.; Demailly, G.; *Bull. Soc. Chim. Fr.*, 827, (1987)) in dry THF (20 ml) dropwise with dry ice-acetone cooling, during which the orange color vanished. The white reaction mixture was stirred under the same cooling conditions for an hour, and then at room temperature for additional 30 minutes; at this point, the reaction mixture became yellow, and methyl (E)-4-benzyloxybutenoate was consumed completely. The reaction mixture was re-cooled in the dry ice acetone bath, and sat. $NH_4Cl$ aq. solution (50 ml) was added. After adding Celite, the mixture was filtered through a pad of Celite, and the filter cake was washed with AcOEt (50 ml×3). The organic layer was separated from the combined filtrate and washings, and the aqueous layer was extracted with AcOEt (30 ml×3). The combined organic layer and AcOEt extracts were washed with sat. NaCl aq. solution (×2), dried ($Na_2SO_4$), and concentrated in vacuo to give a pale yellow oil (31.8 g). This was chromatographed over silica gel ($SiO_2$, Merck Kieselgel 60, 250 g). Elution with n-hexane-AcOEt(7:1→5:1) gave practically pure title compound (19.8 g, 68.5%) as a pale yellow viscous oil: $IR_{max}$ (film): 3350(w), 1735(vs), 1605(w), 1490(m), 1205(s), 1170 (s), 750(s), 700(vs) $cm^{-1}$; $^1$H-NMR δ: 7.48–7.18(m, 10H), 4.60(d, J=8.1 Hz, 1H), 4.56(s, 2H), 3.89(d, J=7.7 Hz, 1H), 3.79(s, 3H), 3.67(d, J=4.8 Hz, 2H), 3.37(dd, J=8.1, 5.5 Hz, 1), 3.20(s, 3H), 2.96(ddt, J=5.5, 7.7, 4.8 Hz, 1H) ppm.

(2) (2R*,3S*,4S*,5S*)-4-Benzyloxymethyl-5-hydroxymethyl-3-methoxycarbonyl-2-phenylpyrrolidine To a stirred and ice-cooled solution of (2R*,3S*,4S*,5S*)-4-benzyloxymethyl-3,5-bis(methoxycarbonyl)-2-phenylpyrrolidine (42.27 g, 0.11 mol) in anhydrous MeOH (Dojindo, 350 ml) was added $NaBH_4$ (12.51 g, 0.33 mol) portionwise. The turbid reaction mixture was stirred with ice-cooling for 2 hours, and then at room temperature for 4.5 hours. The reaction mixture was re-cooled in the ice bath, and Hydrogen Chloride-Methanol Reagent 10 (Tokyo Kasei) was added until the mixture became acidic (pH 1–2). This was concentrated in vacuo, and the syrupy residue was basified to pH ca.10 by adding 10% NaOH aq. solution. The mixture was extracted with AcOEt (80 ml×5). The combined AcOEt extracts were washed with sat. NaCl aq. solution (×1), dried ($Na_2SO_4$), and concentrated in vacuo to give crude title compound (37.0 g, 95%) as a viscous pale yellow oil: IR $ν_{max}$ (film): 3330(s), 1730(vs), 1605(w), 1595(w), 1495(s), 1170(s), 750(s), 700(s) $cm^{-1}$; $^1$H-NMR δ: 7.45–7.16(m, 10H), 4.58(d, J=8.3 Hz, 1H), 4.55(s, 2H), 3.85(dd, J=11.2, 4.6 Hz, 1H), 3.79(dd, J=11.2, 3.9 Hz, 1H), 3.58(dd, J=9.2, 5.3 Hz, 1H), 3,52(dd, J=9.2, 6.6 Hz, 1H), 3.35–3.25(m, 1H), 3.15(s, 3H), 3.14(dd, J=8.3, 5.7 Hz, 1H), 2.17(br.s, 2H) ppm. This was employed in the next step for salt formation without further purification.

(3) (2R*,3S*,4S*,5S*)-4-Benzyloxymethyl-5-hydroxymethyl-3-methoxycarbonyl-2-phenylpyrrolidine semifumarate To a solution of crude (2R*,3S*,4S*,5S*)-4-benzyloxymethyl-5-hydroxymethyl-3-methoxycarbonyl-2-phenylpyrrolidine (38.0 g, 0.11 mol) in EtOH (120 ml) was added a warmed solution of fumaric acid (6.21 g, 0.054 mol) in EtOH (60 ml); on addition, precipitation of white solids took place immediately. To this was added EtOH (80 ml) and $Et_2O$ (60 ml), and the mixture was left to stand in a refrigerator at 4 C. overnight. The white solids were collected by filtration under suction, washed with $Et_2O$ (×1), and dried in vacuo at a temperature of 60 C. for 2 days to give the title semifumarate (35.9 g, 81%) as white powders. The combined filtrate and washings were concentrated in vacuo to give a pale yellow foam (8.08 g), which was crystallized from EtOH-$Et_2O$ to give a second crop of the title compound (1.42 g, 3.2%): a total yield of the title compound, 37.3 g (84%); mp 154–156 C.: $IR_{max}$ (nujol): 3340(s), 2800–2100(br.) 1730(vs) 1130(s), 750(s), 700(s), 675(s) $cm^{-1}$; $^1$H-NMR δ (DMSO-$d_6$): 7.45–7.15(m, 10H), 6.60(s, 1H), 4.50(d, J=9.0 Hz, 1H), 4.48(s, 2H), 3.80–3.35 (m, 7H), 3.15(dd, J=8.8, 6.2 Hz, 1H), 3.03(s, 3H), 2.99(dd, J=9.0, 5.2 Hz, 1H), 2.60–2.38(m, 1H) ppm.

(4) (2R*,3S*,4S*,5S*)-1-Benzyloxycarbonyl-4-benzyloxymethyl-5-hydroxymethyl-3-methoxycarbonyl-2-phenylpyrrolidine To a stirred and ice-cooled suspension of (2R*,3S*,4S*,5S*)-4-benzyloxymethyl-5-hydroxymethyl-3-methoxycarbonyl-2-phenylpyrrolidine semifumarate (12.0 g, 29.0 mmol) in 1M NaOH aqueous solution (70.0 ml, 70.0 mmol) and DME (40 ml) was added benzyl chloroformate (Cbz-Cl, 4.97 ml, d1.195, 34.8 mmol) rapidly. After the heterogeneous white reaction mixture was stirred with ice-cooling for an hour, $H_2O$ (40 ml) and AcOEt(40 ml) was added to dissolve the white solids, and then a further amount of Cbz-Cl (1.0 ml, d1.195, 7.0 mmol) was added to the mixture at room temperature; on the addition, the reaction mixture became neutral. After stirring at room temperature for 30 minutes, the reaction went to almost completion. The stirring was continued at room temperature overnight, and then the layers were separated. The aqueous layer was extracted with AcOEt (50 ml×4). The combined organic layer and AcOEt extracts were washed with 0.5M NaOH aq. solution (×2), half sat. NaCl aq. solution (×1), 0.5M HCl aq. solution (×1), sat. NaCl aq. solution (×1), sat. $NaHCO_3$ aq. solution (×1) and sat. NaCl aq. solution (×1), dried ($MgSO_4$), and concentrated in vacuo to give crude title compound (15.9 g, quant.) as an almost colorless viscous oil: $IR_{max}$ (film): 3420(s), 1738(vs), 1698(vs), 1680(vs), 1605 (w), 1595(w), 1492(s), 1280(s), 1210(s), 1075(s), 758(s), 699(vs) $cm^{-1}$; $^1$H-NMR δ: 7.53–7.10(m, 14H), 6.94(br.s, 1H), 5.30(d, J=9.5 Hz, 1H), 5.02(br.s, 2H), 4.53(d, J=12.1 Hz, 1H), 4.47(d, J=12.1 Hz, 1H), 4.13–3.90(m, 3H), 3.62 (dd, J=9.7, 3.5 Hz, 1H), 3.58–3.41(m, 1H), 3.53(dd, J=9.7, 4.6 Hz, 1H), 3.29(s, 3H), 2.73(br.s, 1H), 1.61(br.s, OH, 1H) ppm. This was employed in the next step without further purification.

(5) (2R*,3S*,4S*,5S*)-1-Benzyloxycarbonyl-4-benzyloxymethyl-5-(t-butyldimethylsilyloxy)methyl-3-methoxycarbonyl-2-phenylpyrrolidine To a stirred and ice-cooled solution of crude (2R*,3S*,4S*,5S*)-1-benzyloxycarbonyl-4-benzyloxymethyl-5-hydroxymethyl-3-methoxycarbonyl-2-phenylpyrrolidine (15.9 g, ca.29.0 mmol) and imidazole (Im, 7.90 g, 116 mmol) in DMF (32.0 ml) was added t-butyldimethylsilyl chloride (8.74 g, 58.0 mmol)in one portion. The cooling bath was removed immediately after the addition, and the stirring was continued at room temperature for ca.5 hours. The reaction mixture was diluted with PhMe—AcOEt (2:1, 300 ml), washed with $H_2O$ (×3), and sat. NaCl aq. solution (×2), dried ($MgSO_4$), and concentrated in vacuo to give a color-less oil (20.5 g). This was chromatographed over $SiO_2$ (Merck Kieselgel 60, 200 g). Elution with n-hexane-AcOEt (50:1→20:1→15:1) gave title compound (16.8 g, 96%) as a colorless viscous oil: IR $ν_{max}$ (film): 1743(s), 1705(vs), 1495(m), 1100(s), 780(s), 745(s), 737(s), 700(s) $cm^{-1}$; $^1$H-NMR δ: 7.48–7.37(m, 3H), 7.37–7.14(m, 11H), 6.90 (br.s, 1H), 5.27(br.d,J=6.1 Hz, 1H), 5.02(br.s, 2H), 4.51–4.41(m, 1H), 4.47(s, 2H), 3.97(dd, J=10.3, 2.6 Hz, 1H), 3.94–3.83(m, 1H), 3.60(d, J=3.7 Hz, 2H), 3.54(dd, J=11.8, 9.5 Hz, 1H), 3.33–3.15(m,1H), 3.28(s, 3H), 0.90 (br.s, 9H), 0.05(br.s, 6H) ppm.

(6) (2R*,3S*,4S*,5S*)-1-Benzyloxycarbonyl-4-benzyloxymethyl-5-(t-butyldimethylsilyloxy)methyl-3-carbamoyl-2-phenylpyrro-lidine Under an atmosphere of $N_2$, a 2.0M solution of $Me_3Al$ in toluene (PhMe) (Aldrich, 150 ml, 300 mmol) was added dropwise to a stirred and ice-cooled suspension of $NH_4Cl$ (14.9 g, 278 mmol) in dry PhMe (280 ml). The stirring at room temperature for 30 minutes gave rise to the clear and homogeneous reaction mixture. To this was added a solution of (2R*,3S*,4S*,5S*)-1-benzyloxycarbonyl-4-benzyloxymethyl-5-(t-butyldimethylsilyloxy)methyl-3-methoxycarbonyl-2-phenylpyrrolidine (16.8 g, 27.8 mmol) in dry PhMe (30 ml) dropwise. The resultant turbid reaction mixture was stirred and heated at an inner temperature of 50 C. for 24 hours. H₂O (20 ml) was added cautiously to the ice-cooled and stirred reaction mixture. To this was then added a 1.0M potassium sodium tartrate aqueous solution (280 ml, 280 mmol), and the stirring was continued under the same cooling conditions for an hour. The mixture was filtered through a pad of Celite, and the filter cake was washed with AcOEt throughly. From the combined filtrate and AcOEt washings the organic layer was separated, and the aqueous layer was extracted with AcOEt (100 ml×3). The combined organic layer and AcOEt extracts were washed with sat. NaCl aq. solution (×1), dried (MgSO₄), and concentrated in vacuo to give a foam (15.4 g). This was chromatographed over SiO₂ (Merck Kieselgel 60, 160 g). Elution with n-hexane-AcOEt (6:1→4:1→1:1) gave pure title compound (12.0 g, 73%) as a white glass: $IR_{max}$ (film): 3350(m), 3200(m), 1699(vs), 1680(vs), 1605(m), 1490(m), 1100(s), 780(s), 730(s), 697(s) cm⁻¹; ¹H-NMR δ: 7.53–7.40 (m, 3H), 7.40–7.03(m, 12H), 5.60(br.s, 1H), 5.27(d, J=9.2 Hz, 1H), 5.03(br.s, 2H), 4.48(br.s, 2H), 4.47(dd, J=10.3, 8.1 Hz, 1H), 4.27(br.s, 1H), 3.99(dd, J=10.3, 2.9 Hz, 1H), 3.88–3.76(m, 1H), 3.70(dd, J=10.3, 3.3 Hz, 1H), 3.60(dd, J=10.3, 4.7 Hz, 1H), 3.32(dd, J=11.7, 9.2 Hz, 1H), 3.24–3.08 (m, 1H), 0.90(br.s, 9H), 0.05(br.s, 6H) ppm.

(7) (2S*,3S*,4S*,5S*)-1-Benzyloxycarbonyl-4-benzyloxymethyl-3-[N-(t-butoxycarbonyl)amino]-5-(t-butyldimethylsilyloxy)methyl-2-phenylpyrrolidine To a warmed and stirred solution of (2R*,3R*,4S*,5S*)-1-benzyloxycarbonyl-4-benzyloxymethyl-5-(t-butyldimethylsilyloxy)methyl-3-carbamoyl-2-phenylpyrrolidine (12.6 g, 21.3 mmol) in t-BuOH (200 ml) was added Pb(OAc)₄ (16.1 g, 36.3 mmol) in one portion.[7] The resulting brown mixture was stirred and heated at a gentle reflux for 45 minutes. The mixture was ice-cooled, neutralized with sat. NaHCO₃ aq. solution, and then filtered through a pad of Celite. The filter cake was washed with CH₂Cl₂. The combined filtrate and washings were concentrated in vacuo. The aqueous residue was extracted with CH₂Cl₂ (50 ml×3). The combined CH₂Cl₂ extracts were washed with sat. NaCl aq. solution (×1), dried (MgSO₄), and concentrated in vacuo to give title compound (14.5 g, quant.) as a pale Yellow oil: $IR_{max}$ (film): 1715(vs), 1700(vs), 1683(vs), 778(s), 738(s), 698(s) cm⁻; ¹H-NMR δ: 5.13(br.d, J=7.7 Hz, 1H; NCH₂Ph), 4.51(br.s, 2H; OCH₂Ph), 1.25[s, 9H; NHCO₂C(CH₃)₃], 0.92[s, 9H; OSiC(CH₃)₃], 0.10[br.s, 6H; OSi(CH₃)₂] ppm. This was employed in the next step without further purification.

(8) (2S*,3S*,4S*,5S*)-1-Benzyloxycarbonyl-4-benzyloxymethyl-3-[N-(t-butoxycarbonyl)amino]-5-hydroxymethyl-2-phenylpyrrolidine To a stirred and ice-cooled solution of (2S*,3S*,4S*,5S*)-1-benzyloxycarbonyl-4-benzyloxymethyl-3-[N-(t-butoxycarbonyl)amino]-5-(t-butyldimethylsilyloxy)methyl-2-phenylpyrrolidine (14.5 g, ca.21.3 mmol) in dry THF (20 ml) was added a mixture of glacial AcOH (1.59 ml, d1.049, 27.7 mmol) and a 1.0M solution of (n-Bu)₄NF in THF (Aldrich, 32.0 ml, 32.0 mmol) dropwise. After stirring at room temperature for 6 hours, a further amount of a 1.0M solution of (n-Bu)₄NF in THF (15.0 ml, 15.0 mmol) was added dropwise at room temperature. After the stirring was continued for 2 days, the resultant orange mixture was neutralized with sat. NaHCO₃ aq. solution, and concentrated in vacuo at a bath temperature of 40 C. The residue was diluted with AcOEt (200 ml), washed with H₂O (×2), sat. NaHCO₃ aq. solution (×1), and sat. NaCl aq. solution (×1), dried (MgSO₄), and concentrated in vacuo to give a dark red viscous oil (13.9 g). This was chromatographed over SiO₂ (Merck Kieselgel 60, 130 g). Elution with n-hexane-AcOEt (20:1→10:1→5:1→4:1→2:1) gave a red solid (10.6 g). This was recrystallized from AcOEt-n-hexane; the crystals were filtered off, washed with AcOEt-n-hexane (1:4, ×1), and dried in vacuo to give the title compound (9.0 g, 78%) as a slightly purple crystals. A portion of it was recrystallized from AcOEt-n-hexane to afford an analytical sample of the title compound: mp 126.5–129.5 C. (white fine needles); $IR_{max}$ (nujol): 3430(s), 3380(s), 1690(vs), 1518(s), 1498(m), 1100(s), 785(m), 770(s), 747(s), 740(s), 715(s), 695(s) cm⁻¹; ¹H-NMR δ: 7.45–7.15(m, 17H), 6.94(br.s, 1H), 5.22(d, J=8.1 Hz, 1H), 5.02(br.s, 2H), 4.87(br.s, 1H) 4.52(s, 2H), 4.30(dd, J=19.0, 9.0 Hz, 1H), 4.2–4.00(m, 2H), 4.03–3.90 (m, 1H), 3.68–3.50(m, 2H), 2.10–1.85(m, 1H), 1.37(br.s, 9H) ppm.

(9) (2S*,3S*,4S*,5S*)-1-Benzyloxycarbonyl-4-benzyloxymethyl-3-[N-(t-butoxycarbonyl)amino]-5-iodomethyl-2-phenylpyrrolidine To a stirred mixture of (2S*,3S*,4S*,5S*)-1-benzyloxycarbonyl-4-benzyloxymethyl-3-[N-(t-butoxycarbonyl)amino]-5-hydroxymethyl-2-phenylpyrrolidine (9.00 g, 16.5 mmol), Ph₃P (10.8 g, 41.3 mmol) and Im (2.81 g, 41.3 mmol) in dry PhMe (240 ml) was added I₂ (8.38 g, 33.0 mmol) in one portion at room temperature. After stirring and heating at a gentle reflux for an hour, the dark brown mixture was allowed to cool to room temperature, and then sat. Na₂SO₃ aq. solution (70 ml) was added until the dark color due to the excess I₂ was discharged. The layers were separated, and the organic layer was washed with sat. NaCl aq. solution (×1), dried (MgSO₄), and concentrated in vacuo to give a deep red oil (22.9 g). This was chromatographed over SiO₂ (Merck Kieselgel 60, 230 g). Elution with n-hexane-AcOEt (30:1→10:1→6:1) gave the title compound (9.95 g, 92%) as a white solid. A portion of it (105 mg) was recrystallized from isopropyl ether (IPE) to afford an analytical sample of the title compound as white powders (mp 107.5–108.5 C.); $IR_{max}$ (nujol): 3440(s), 1705(vs), 1500(s), 1165(s), 780(m), 770(m), 755(m), 740(m), 707(s), 695(s) cm⁻¹; ¹H-NMR δ: 7.60–7.15(m, 14H), 7.09(br.s, 2H), 5.19(d, J=8.8 Hz, 1H), 5.03(br.s, 2H), 2H), 4.44(ddd, J=9.0, 9.0, 9.0 Hz, 1H), 4.15–3.97(m, 1H), 3.97–3.75(m, 2H), 3.71(dd, J=9.7, 5.3 Hz, 1H), 3.64(dd, J=9.7, 5.3 Hz, 1H), 2.34–2.18(m, 1H), 1.36(br.s, 9H) ppm.

(10) (2S*,3S*,4R*,5R*)-1-Benzyloxycarbonyl-4-benzyloxymethyl-3-[N-(t-butoxycarbonyl)amino]-5-methyl-2-phenylpyrrolidine A mixture of (2S*,3S*,4S*,5S*)-1-benzyloxycarbonyl-4-benzyloxymethyl-3-[N-(t-butoxycarbonyl)amino]-5-iodomethyl-2-phenylpyrrolidine (9.85 g, 15.0 mml), Et₃N (5.23 ml, d0.726, 37.5 mmol), and 10% Pd-C (1.83 g) in EtOH-AcOEt (2:1, 210 ml) was stirred under a slightly positive pressure of H₂ (baloon) at room temperature for 5 hours, during which the white solids of Et₃NH⁺I⁻ precipitated. The catalysts and white precipitates were filtered off by the aid of a Celite pad, and washed with AcOEt followed by CH₂Cl₂ throughly. The combined filtrate and washings were concentrated in vacuo. The residue was diluted with PhMe-AcOEt (1:1, 200 ml), washed with sat. Na₂SO₃ aq. solution (×3), H₂O (×2), and sat. NaCl aq. solution (×1), dried (MgSO₄), and concentrated in vacuo to give the title compound (7.60 g, 95%) as slightly yellow solids. This was employed in the next step without further purification. A portion of it (0.15 g) was recrystallized from AcOEt-n-hexane to give an analytical sample of the title compound (0.11 g, 65%) as white fine needles (mp 143–144 C.): $IR_{max}$ (nujol): 3380(s), 1710(s), 1688(s), 1520(s), 1500(w), 770

(m), 738(s), 715(s), 698(s) cm$^{-1}$; $^1$H-NMR δ: 7.50–7.17(m, 1H), 7.12–6.93(m,1H), 5.25(d, J=8.4 Hz, 1H), 5.04(br.s, 2H), 4.49(br.s, 2H), 4.26(ddd, J=11.3, 9.0, 9.0 Hz, 1H), 4.16–4.00(m, 1H), 3.95–3.77(m, 1H), 3.55(br.d, J=4.8 Hz, 2H), 1.97–1.80(m, 1H), 1.63(br.d, J=4.4 Hz, 3H), 1.40(br.s, 9H) ppm.

(11) (2S*,3S*,4S*,5R*)-3-Amino-1-benzyloxycarbonyl-4-benzyloxy-methyl-5-methyl- 2-phenylpyrrolidine To a stirred solution of (2S*,3S,4R*,5R*)-1-benzyloxycarbonyl-4-benzyloxymethyl-3-[N-(t-butoxycarbonyl)amino]-5-methyl-2-phenylpyrrolidine (0.60 g, 1.13 mmol) in AcOEt (13.0 ml) was added conc. HCl aq. (8.0 ml) at room temperature; on the addition, evolution of CO$_2$ gas was observed. After stirring at room temperature for 30 minutes, the reaction mixture was concentrated in vacuo. The residue was basified with 10% NaOH aq. solution to pH 10–11, and the mixture was extracted with CH$_2$Cl$_2$. The combined CH$_2$Cl$_2$ extracts were washed with sat. NaCl aq. solution, dried (K$_2$CO$_3$), and concentrated in vacuo to give crude title compound (0.51 g, quant.) as a yellow viscous oil: IR$_{max}$ (nujol): 3380(w), 3330(w), 1698 (s), 1495(m), 1110(s), 738(s), 698(s) cm$^{-1}$; $^1$H-NMR δ: 7.60–7.15(m, 9H), 7.02(br.s, 1H), 5.04(br.s, 2H), 5.01(d, J=8.3 Hz, 1H), 4.52(s, 2H), 3.83(dq, J=9.2, 5.9 Hz, 1H), 3.61(d, J=4.8 Hz, 2H), 3.51(dd, J=11.0, 8.3 Hz, 1H), 1.86–1.67(m, 1H), 1.60(d, J=5.9 Hz, 3H), 1.45–1.07(br.m, 3H; NH$_2$+OH) ppm. This was employed in the next step without further purification.

(12) (2S*,3S*,4R*,5R*)-1-Benzyloxycarbonyl-4-benzyloxymethyl-3-[N-(5-isopropyl-2-methoxybenzyl)amino]-5-methyl-2-phenylpyrrolidine To a stirred solution of crude (2S*,3S*,4R*,5R*)-3-amino-1-benzyloxycarbonyl-4-benzyloxymethyl-5-methyl-2-phenylpyrrolidine (0.51 g, 1.13 mmol) in dry CH$_2$Cl$_2$ (12 ml) was added a solution of 5-isopropyl-2-methoxybenzaldehyde (0.25 g, 1.41 mmol) in dry CH$_2$Cl$_2$ (2 ml) at room temperature. To this solution was added NaBH(OAc)$_3$ (0.36 g, 1.70 mmol) portionwise at room temperature. The added NaBH(OAc)$_3$ dissolved gradually with stirring at room temperature. After 3 hours the slightly turbid reaction mixture was basified to pH 10–11 with 10% NaOH aq. solution, and the mixture was separated. The aqueous layer was extracted with CH$_2$Cl (×3). The combined CH$_2$Cl$_2$ solution was washed with sat. NaCl aq. solution (×1), dried (K$_2$CO$_3$), and concentrated in vacuo to give a viscous oil (0.79 g). This was subjected to SiO$_2$ chromatography (Merck Kieselgel 60, 8.0 g) eluted with CH$_2$Cl$_2$—MeOH (300:1) to give title compound (0.16 g, 24%) as a viscous colorless oil and an oily mixture (0.47 g) of 5-isopropyl-2-methoxybenzaldehyde and title compound. The latter mixture was chromatographed again over SiO$_2$ (Merck Kieselgel 60, 7.0 g). Elution with n-hexane-AcOEt (30:1) followed by CH$_2$Cl$_2$—MeOH (100:1) gave an additional amount of the title compound (0.45 g, 67%); the total yield of the title compound amounted to 0.61 g (91%): IR$_{max}$ (film): 3350(w), 1700(vs), 1610(w), 1497(s), 1250(s), 1110 (s), 815(m), 772(m), 735(s), 698(s) cm$^{-1}$; $^1$H-NMR δ: 7.50–7.11(m, 14H), 7.02(dd, J=8.2, 2.2 Hz, 1H), 7.01(br.s, 1H), 6.92(d, J=2.2 Hz, 1H), 6.70(d, J=8.2 Hz, 1H), 5.20–4.93(m, 3H), 3.95–3.78(m,1H), 3.78–3.49(m, 4H), 3.63(s, 3H), 3.33(dd, J=10.3, 8.0 Hz), 2.77 (sep, J=7.0 Hz, 1H), 2.11–1.95(m, 1H), 1.58(br.s, 1H; NH), 1.49(br.s, 3H), 1.17(d, J=7.0 Hz, 6H) ppm.

(13) (2S*,3S*,4R*,5R*)-4-Benzyloxymethyl-3-[-N-(5-isopropyl-2-methoxybenzyl)amino]-5-methyl-2-phenylpyrrolidine 20% Pd(OH)$_2$—C (Pearlman's catalyst, Aldrich; 0.33 g) was added to a solution of (2S*,3S*,4R*,5R*)-1-benzyloxycarbonyl-4-benzyloxymethyl-3-[N-(5-isopropyl-2-methoxybenzyl)amino]-5-methyl-2-phenylpyrrolidine (0.61 g,1.03 mmol) and HCO$_2$NH$_4$ (0.39 g, 6.18 mmol) in MeOH (20 ml). The mixture was stirred and heated at a gentle reflux for 30 minutes. The catalysts were filtered off by the aid of a Celite pad, and washed with MeOH. The combined filtrate and washings were concentrated in vacuo. To the residue was added 1M NaOH aq. solution until the mixture became basic (pH 10–11). This was extracted with CH$_2$Cl$_2$ (×4). The combined CH$_2$Cl$_2$ extracts were washed with sat. NaCl aq. solution (×1), dried (K$_2$CO$_3$), and concentrated in vacuo to give a pale yellow oil (0.47 g). This was chromatographed over SiO$_2$ (Merck Kieselgel 60, 7.0 g). Elution with CH$_2$Cl$_2$—MeOH (300:1→200:1→100→60:1→50:1) gave title compound (0.40 g, 85%) as a pale yellow viscous oil: IR$_{max}$ (film): 3340(w), 1610(m), 1498(s), 1250(s), 1110(s), 810(m), 738 (s), 700(s) cm$^1$; $^1$H-NMR δ: 7.43–7.20(m, 10H), 7.01(dd, J=8.4, 2.2 Hz, 1H), 6.82(d, J=2.2 Hz, 1H), 6.65(d, J=8.4 Hz, 1H), 4.56(s, 2H), 4.20(d, J=5.5 Hz, 1H), 3.67(d, J=13.6 Hz, 1H), 3.493(dd, J=9.3, 6.2 Hz, 1H), 3,489(s, 3H), 3.57(dd, J=9.3, 6.4 Hz, 1H), 3.42(d, J=13.6 Hz, 1H), 3.13(dd, J=5.5, 2.6 Hz, 1H), 3.06(dq, J=6.2, 6.2 Hz, 1H), 2.74(sep, J=7.0 Hz, 1H), 2.17–1.85(m, 3H), 1.42(d, J=6.2 Hz, 3H), 1.16(d, J=7.0 Hz, 6H) ppm.

(14) (2S*,3S*,4R*,5R*)-4-Benzyloxymethyl-3-[N-(5-isopropyl-2-methoxybenzyl)amino]-5-methyl-2-phenylpyrrolidine dihydrochloride An excess amount of Hydrogen Chloride, Methanol Reagent 10 (Tokyo Kasei) was added to (2S*,3S*,4R*,5R*)-4-benzyloxymethyl-3-[N-(5-isopropyl-2-methoxybenzyl)amino]-5-methyl-2-phenylpyrrolidine (0.40 g, 0.87 mmol) until the mixture became acidic. The solvent MeOH was evaporated in vacuo, and the syrupy residue was crystallized from EtOH—Et$_2$O to give title compound (0.40 g, 87%) as white powders (mp 129–133 C.): IR$_{max}$ (nujol): 3450(w), 3100–2100(br.s), 1510(s), 1255 (s), 1087(m), 810(w), 755(m), 700(s) cm$^{-1}$; $^1$H-NMR δ (DMSO-d$_6$): 7.83(br.s, 2H), 7.62–7.40(m, 3H), 7.40–7.33 (m, 4H), 7.37–7.25(m, 1H), 7.25–7.12(m, 2H), 6.89(d, J=8.4 Hz, 1H), 5.11(br.s, 1H), 4.59(s, 2H), 3.78–3.50(m, 5H), 3.67(br.s, 2H), 3.45–3.30[m, 3H; overlaped with the signals (δ 3.35) due to H$_2$O], 3.35[s, 3H; overlaped with the signals (δ 3.35) due to H$_2$O], 2.77(sep, J=7.0 Hz, 1H), 2.55–2.48[m, 1H; overlaped with the signals (δ 2.50) due to DMSO], 1.64(br.d, J=5.9 Hz, 3H), 1.14(d, J=7.0 Hz, 6H) ppm.

(15) (2S*,3S*,4R*,5R*)-3-[N-(t-Butoxycarbonyl)amino]-4-hydroxymethyl-5-methyl-2-phenylpyrrolidine Na (1.88 g, 81.8 mmol) was added portionwise to liq. NH$_3$ (ca.250 ml) with stirring and cooling in a dry ice-acetone bath. To the resulting deep blue solution was added dropwise a solution of (2S*,3S*,4R*,5R*)-1-benzyloxycarbonyl-4-benzyloxymethyl-3-[N-(t-butoxycarbonyl)-amino]-5-methyl-2-phenylpyrrolidine (5.90 g, 11.1 mmol) in dry THF (50 ml). After stirring with dry ice-acetone cooling for 2 hours the cooling bath was removed, and the stirring was continued under the NH$_3$-refluxing conditions for 30 minutes, during which the deep blue color persisted. The reaction mixture was cooled with dry ice-acetone, and solid NH$_4$Cl was added until the deep blue color was discharged. After the solvent NH$_3$ was evaporated, the white solid residue was extracted with CH$_2$Cl$_2$. The combined CH$_2$Cl$_2$ extracts were dried (K$_2$CO$_3$), and concentrated in vacuo to give a mixture (4.55 g) of the title compound, (2S*,3S*, 4R*,5R*)-1-benzyloxycarbonyl-4-benzyloxymethyl-3-[N-(t-butoxycarbonyl)-amino]-5-methyl-2-phenylpyrrolidine, and 1,2-diphenylethane in an approximate ratio of 1:0.085:0.5; the ratio was estimated by $^1$H-NMR spectroscopy: δ 3.01 ppm (dq, J=8.8, 6.0 Hz, 1H; NCHMe for the title compound); δ 4.49 ppm (s, 0.17H; CH$_2$OCH$_2$Ph for (2S*,3S*,4S*,5R*)-1-benzyloxycarbonyl-4-benzyloxymethyl-3-[N-(t-butoxycarbonyl)-amino]-5-methyl-2-phenylpyrrolidine); δ 2.92 ppm [s, 2H; Ph(CH$_2$)$_2$Ph]. A solution of this crude product (4.55 g) in dry THF (30 ml) was added to a deep blue solution of Na (1.20 g, 52.2 mmol) in liq. NH$_3$ (ca.200 ml) dropwise with stirring and dry ice-acetone cooling. The reaction mixture was stirred under the same cooling conditions for 2 hours, and then under the NH$_3$-refluxing conditions for 30 minutes. The deep blue color was discharged dy adding solid NH$_4$Cl with dry ice-acetone cooling. After evaporating the solvent NH$_3$, the solid residue was extracted with CH$_2$Cl$_2$. The combined CH$_2$Cl$_2$ extracts were dried (K$_2$CO$_3$), and concentrated in vacuo to give a 7:3 mixture (3.84 g) of the title compound and 1,2-diphenylethane as a pale yellow viscous oil, the ratio being estimated also by $^1$H-NMR spectroscopy; the net yield of title compound was calculated to be 90% based on the above ratio taken into account: IR$_{max}$ (film): 3390(s), 1700 (vs), 1685(vs), 1603(w), 1522(s), 1510(s), 1497(s),1170(s), 768(w), 738(w), 698(s) cm$^{-1}$; $^1$H-NMR δ: title compound, 7.43–7.30(m, 5H), 4.40(d, J=7.4 Hz, 1H), 4.38(br.d, J=7.4 Hz, 1H; NHBoc), 4.08(ddd, J=7.4, 7.4, 5.5 Hz, 1H), 3.70–3.58(m, 2H), 3.01(dq, J=8.8, 6.0 Hz, 1H), 1.76–1.64 (m, 1H), 1.35–1.22(m, 2H; OH+NH), 1.312(d, J=6.0 Hz, 3H), 1.309(s, 9H) ppm; 1,2-diphenylethane, 7.30–7,25(m, 1.8H), 7.22–7.15(m, 2.7H), 2.92(s, 1.8H) ppm. While this crude product solidified on standing at room temperature, it was employed in the next step without further purification.

(16) (2S*,3S*,4R*,5R*)-1-Benzyloxycarbonyl-3-[N-(t-butoxycarbonyl)amino]-4-hydroxymethyl-5-methyl-2-phenylpyrrolidine Benzyl chloroformate (Cbz-Cl, 1.57 ml, d1.195, 11.0 mmol) was added to a stirred and ice-cooled mixture of crude (2S*,3S*,4R*,5R*)-3-[N-(t-butoxycarbonyl)amino]-4-hydroxymethyl-5-methyl-2-phenylpyrrolidine (3.84 g, ca.10.0 mmol), and 2M NaOH aq. solution (8.0 ml, 16.0 mmol) in DME-THF (1:1, 14 ml). After stirring at room temperature for 2.5 hours, 2M NaOH aq. solution (2.0 ml, 4.0 mmol) and Cbz-Cl (0.29 ml, d1.195, 2.0 mmol) were added at room temperature, and the stirring was continued for 2 hours. The mixture was extracted with AcOEt (×4). The combined AcOEt extracts were washed with sat. NaCl aq. solution (×1), dried (MgSO$_4$), and concentrated in vacuo to give a white solid (5.57 g). This was recrystallized from AcOEt-n-hexane to give pure title compound (3.33 g, 76%). The yellow orange mother liquor (2.22 g) was chromatographed over SiO$_2$ (Merck Kieselgel 60, 20 g). Elution with n-hexane-AcOEt (10:1→5:1) give (2S*,3S*,4R*,5R-)-1-benzyloxycarbonyl-4-[(benzyloxycarbonyloxy)methyl]-3-[N-(t-oxycarbonyl)amino]-5-methyl-2-phenylpyrrolidine (0.31 g, 5.4%) as a fairly pure solid, which was recrystallized from AcOEt-n-hexane to give an analytical sample of (2S*,3S*,4R*,5R*)-1-benzyloxycarbonyl-4-[(benzyloxycarbonyloxy)methyl]-3-[N-(t-butoxycarbonyl)amino]-5-methyl-2-phenylpyrrolidine (0.28 g, 4.9%): mp 148.0–188.5 C. (white needles); IR $_{max}$ (nujol): 3400(m), 1763(m), 1735(s), 1690(s), 1510(s), 782(m), 770(m), 740(s), 713(s), 695(s) cm$^{-1}$; $^1$H-NMR δ: 7.44–7.13(m, 13H), 7.03 (br.s, 2H), 5.22(d, J=8.8 Hz, 1H), 5.15(s, 2H), 5.04(br.s, 2H), 4.48–4.24(m, 2H), 4.25–4.10(M, 1H), 3.92(d, J=9.2 Hz, 1H), 3.84(dq, J=9.8, 6.1 Hz, 1H), 2.00–1.83(m, 1H), 1,63(d, J=4.8 Hz, 3H), 1.39(s, 9H) ppm; Further elution with n-hexane-AcOEt (5:1→1:1) gave an additional amount of title compound (0.48 g) as a fairely pure solid, which was recrystallized from AcOEt-n-hexane to give pure title compound (0.29 g, 6.8%); the total yield of title compound amounted to 3.62 g (82%): mp 153.5–154.0 C. (white fine needles); IR$_{max}$ (nujol): 3450(s), 3400(s), 1690vs), 1518(s), 1170(s), 772(m), 760(w), 740(m), 710(m), 700(s) cm$^{-1}$; $^1$H-NMR δ: 7.50–7.13(m, 9H), 7.08(br.s, 1H), 5.15(d, J=8.4 Hz, 1H), 5.05(br.s, 2H), 4.36(ddd, J=11.0, 8.4, 8.4 Hz, 1H), 4.01 br.d, J=11.0 Hz, 1H), 3.90(dq, J=9.9, 6.0 Hz, 1H), 3.64(br.s, 2H), 1.65–1.45(m, 5H), 1.40(s, 9H) ppm.

(17) (2S*,3S*,4R*,5R*)-3-Amino-1-benzyloxycarbonyl-4-hydroxymethyl-5-methyl-2-phenylpyrrolidine To a stirred solution of (2S*,3S*,4R*,5R*)-1-benzyloxycarb-onyl-4-(benzyloxycarbonyloxy)-methyl-3-[N-(t-butoxycarbonyl)-amino]-5-methyl-2-phenylpyrrolidine (0.80 g, 1,82 mmol) in AcOEt (15 ml) was added conc. HCl aq. (8.0 ml) at room temperature; on the addition evolution of CO$_2$ gas took place. After stirring at room temperature for 1.5 hours, the reaction mixture was concentrated in vacuo to give a syrupy residue. This was basified to pH 10–11 with 20% NaOH aq. solution, and then extracted with AcOEt. The combined AcOEt extracts were washed with sat. NaCl aq. solution (×1), dried (K$_2$CO$_3$), and concentrated in vacuo to give title compound (0.61 g, 98%): IR$_{max}$ (film): 3380(m), 1700(s), 1682(s), 1605(m), 1585(m), 1110(s), 750(m), 700(s) cm$^{-1}$; $^1$H-NMR δ: 7.52–7.13(m, 9H), 6.99(br.s, 1H), 5.05(br.s, 3H), 4.92(d, J=8.1 Hz, 1H), 3.89(dd, J=10.4, 2.9 Hz, 1H), 3.76(dd, J=10.4, 10.4 Hz, 1H), 3.60–3.45 (m, 1H), 3.50(dd, J=11.2, 8.1 Hz, 1H), 2.10–1.70 (m, 3H), 1.61(br.d, J=4.3 Hz, 3H) ppm. This was employed in the next step without further purification.

(18) (2S*,3S*,4R*,5R*)-1-Benzyloxycarbonyl-4-hydroxymethyl-3[N-(5-isopropyl-2-methoxybenzyl)amino]-5-methyl-2-phenylpyrrolidine To a stirred solution of (2S*,3S*,4S*,5R*)-3-amino-1-benzyloxycarbonyl-4-hydroxymethyl-5-methyl-2-phenylpyrrolidine (0.61 g, 1.79 mmol) in dry CH$_2$Cl$_2$ (14 ml) was added a solution of 5-isopropyl-2-methoxybenzaldehyde (0.40 g, 2.24 mmol) in dry CH$_2$Cl$_2$(2 ml) at room temperature. To this was then added NaBH (OAc)$_3$ (0.57 g, 2.69 mmol) portionwise at room temperature. The added NaBH(OAc)$_3$ dissolved gradually with stirring at room temperature. After stirring for 3 hours at room temperature, the reaction mixture was basified to pH 10–11 with 10% NaOH aq. solution. The mixture was separated, and the aqueous layer was extracted with CH$_2$Cl$_2$ (×3). The combined CH$_2$Cl$_2$ solution was washed with sat. NaCl aq. solution (×1), dried (K$_2$CO$_3$), and concentrated in vacuo to give a yellow oil (1.34 g). This was chromatographed over SiO$_2$ (Merck Kieselgel 60, 20 g). Elution with n-hexane-AcOEt (30:1) followed by CH$_2$Cl$_2$—MeOH (400:1→200:1) gave title compound (0.70 g, 78%) as a viscous pale yellow oil: IR$_{max}$ (film): 3330(s), 1700(s), 1610(m), 1500(s), 1250(s), 1110(s), 1030(s), 815(s), 770(s), 738(s), 700(s) cm$^-$; $^1$H-NMR δ: 7.45–7.16(m, 9H), 7.05(dd, J=8.4, 1.8 Hz, 1H), 7.02(br.s, 1H), 6.88(d, J=1.8 Hz, 1H), 6.71(d, J=8.4 Hz, 1H), 5.33–4.93(m, 3H), 3.97–3.65(m, 3H), 3.81(d, J=12.1 Hz, 1H), 3.72(d,J=12.1 Hz, 1H), 3.67(s, 3H), 3.53–3.35(m, 1H), 3.38(dd,J=11.5, 7.9 Hz), 2.79 (sep, J=7.0 Hz, 1H), 2.17–1.98(m, 1H), 1.56(br.s, 4H), 1.18(d, J=7.0 Hz, 6H) ppm.

(19) (2S*,3S*,4R*,5R*)-4-Hydroxymethyl-3-[N-(5-isopropyl-2-methoxybenzyl)amino]5-methyl-2-phenylpyrrolidine 20% Pd(OH)$_2$—C (Pearlman's catalyst, Aldrich; 0.44 g) was added to a solution of (2S*,3S*,4R*,5R*)-1-benzyloxycarbonyl-4-hydroxymethyl-3-[N-(5-isopropyl-2-methoxybenzyl)amino]-5-methyl-2-phenylpyrrolidine(0.70 g, 1.36 mmol) and HCO$_2$NH$_4$ (0.51 g, 8.16 mmol) in MeOH (20 ml). The reaction mixture was stirred and heated at a gentle reflux for 30 minutes. The catalysts were filtered off by the aid of a Celite pad, and washed with MeOH. The combined filtrate and washings were concentrated in vacuo. The residue was basified to pH 10 with 1M NaOH aq. solution, and extracted with AcOEt (×4). The combined AcOEt extracts were dried (K$_2$CO$_3$), and concentrated in vacuo to give a pale yellow viscous oil (0.46 g), which crystallized spontaneously on standing in a refrigerator for 2 days. This was recrystallized from AcOEt-n-hexane to give title compound (0.33 g, 63%) as white crystals. The yellow mother liquor was chromatographed over SiO$_2$ (Merck Kieselgel 60, 2.0 g). Elution with CH$_2$Cl$_2$—MeOH (50:1→20:1) gave an additional amount of title compound (0.06 g, 12%) as a pale yellow viscous oil, which crystallized spontaneously on standing at room temperature; the total yield of title compound amounted to 0.39 g (76%): mp 76.0–78.0 C. (white powders); IR$_{max}$ (nujol): 3180(w), 1610 (w), 1509(s), 1240(s), 1050(m), 800(m), 750(m), 696(m) cm$^{-1}$; $^1$H-NMR δ: 7.47–7.22(m, 5H), 7.01(dd, J=8.4, 2.2 Hz, 1H), 6.68(d, J=8.4 Hz, 1H), 6.65(d, J=2.2 Hz, 1H), 4.50(d, J=7.7 Hz, 1H), 3.78(dd, J=10.3, 4.3 Hz, 1H), 3.66 (dd, J=10.3, 9.4 Hz, 1H), 3.64(s, 3H), 3.61(d,J=12.3 Hz, 1H), 3.47(d,J=12.3 Hz, 1H), 3.39(dd, J=9.7, 7.7 Hz, 1H), 2.92(dq, J=9.4, 6.0 Hz, 1H), 2.76(sep, J=6.8 Hz, 1H), 2.13(br.s, 3H), 1.84(ddd, J=9.4, 9.4, 4.3 Hz, 1H), 1.27(d, J=6.0 Hz, 3H), 1.16(d, J=6.8 Hz, 6H) ppm.

(20) (2S*,3S*,4R*,5R*)-4-Hydroxymethyl-3-[N-(5-isopropyl-2-methoxybenzyl)amino]-5-methyl-2-phenylpyrrolidine fumarate Fumaric acid (94.6 mg, 0.8 mmol) was added to a solution of (2S*,3S*,4R*,5R*)-4-hydroxymethyl-3-[N-(5-isopropyl-2-methoxybenzyl)amino-5-methyl-2-phenylpyrrolidine (0.31 g, 0.81 mmol) in EtOH to give the clear solution, and the solvent EtOH was evaporated in vacuo. The residual solid was recrystallized from EtOH—AcOEt; after keeping, in a freezer overnight, the white crystals were filtered off, washed with Et$_2$O—EtOH (20:1), and dried in vacuo at 40 C. to afford the title fumarate (0.34 g, 83%) as white powders (mp 161.0–162.5 C.): IR$_{max}$ (nujol): 3300(m), 3000–2200(br.,m), 1680(s), 1625(s), 1505(s), 1240(m), 1038(s), 820(s), 770(s), 750(s), 740(m), 700(s) cm$^{-1}$; $^1$H-NMR δ (DMSO-d$_6$): 7.50–7.26(m, 5H), 7.01(dd, J=8.4, 1.8 Hz, 1H), 6.87(d,J=1.8 Hz, 1H), 6.76(d,J=8.4 Hz, 1H), 6.47(s, 2H), 4.45(d, J=5.5 Hz, 1H), 4.10–3.30(m, 7H), 3.51(s, 3H), 3.34–3.17(m, 2H), 3.17–3.06(m 1H), 2.74(sep, J=7.0 Hz, 1H), 1.97–1.83(m, 1H), 1.36(d, J=6.2 Hz, 3H), 1.12(d, J=7.0 Hz, 6H) ppm.

(21) (2S*,3S*,4R*,5R*)-1-Benzyloxycarbonyl-3-[N-(t-butoxycarbonyl)amino]-4-formyl-5-methyl-2-phenylpyrrolidine To a stirred and water-cooled solution of (2S*,3S*,4R*,5R*)-1-benzyloxycarbonyl-3-[N-(t-butoxycarbonyl) amino]-4-hydroxymethyl-5-methyl-2-phenylpyrrolidine (2.60 g, 5.90 mmol) and Et$_3$N (5.70 ml, d0.726, 40.9 mmol) in DMSO (dried over molecular sieves 4, 36 ml) was added sulfer trioxide pyridine complex (SO$_3$ Py, Wako, 5.42 g, 34.1 mmol) portionwise. Just after the addition the water bath was removed, and the stirring was continued at room temperature for 1.5 hours. The reaction mixture was poured into a mixture of ice and water (80 ml). The mixture was extracted with CH$_2$Cl$_2$ (30 ml×5). The combined CH$_2$Cl$_2$ extracts were washed with 10% citric acid aq. solution (30 ml×4) until the aqueous washing reached the acidity of citric acid (pH ca.3), H$_2$O (30 ml×1), sat. NaHCO$_3$ aq. solution (40 ml×1), and sat. NaCl aq. solution (×1), dried (MgSO$_4$), and concentrated in vacuo to give crude title compound (3.66 g, quant.) as a pale yellow viscous oil; while the yield was overestimated owing to contamination with the solvent employed, this crude product solidified on standing in a refrigerator: IR$_{max}$ (film): 3400(m, shoulder), 3350(m), 2720 (w), 1710(vs), 1690(vs, shoulder), 1605(w), 1585(w), 1520 (s), 1500(s), 1165(s), 770(m), 730(s), 700(s) cm$^{-1}$; $^1$H-NMR δ: 9.65(d, J=3.7 Hz, 1H), 7.40–7.10(m, 9H), 7.05(br.s, 1H), 5.27(d, J=8.5 Hz, 1H), 5.06(br.s, 2H), 4.78–4.57(m, 1H), 4.24(dq, J=9.5, 6.1 Hz, 1H), 4.05(br.d, J=9.2 Hz, 1H), 2.77–2.50(m, 1H), 1.61(d, J=6.1 Hz, 1H), 1.37(s, 9H) ppm. This was employed in the next step without further purification.

(22) (2S*,3S*,4R*,5R*)-1-Benzyloxycarbonyl-3-[N-(t-butoxycarbon-yl)amino]-4-methoxycarbonyl-5-methyl-2-phenylpyrrolidine To a stirred and ice-cooled mixture of crude (2S*,3S*,4R*,5R*)-1-benzyloxycarbonyl-3-[N-(t-butoxycarbonyl) amino]-4-formyl-5-methyl-2-phenylpyrrolidine (3.66 g, 5.90 mmol) and NaHCO$_3$ (19.8 g, 0.24mol) in MeOH—H$_2$O (9:1 by volume; 30 ml) was added a 2.0 M solution of Br$_2$ in MeOH—H$_2$O (9:1; 30 ml, 60 mmol) dropwise. The reaction mixture was stirred at room temperature for 2 hours, during which the color changed from deep red to orange. Sat. Na$_2$S$_2$O$_3$ (hypo) aq. solution was added dropwise to the mixture with ice-cooling, until the orange color due to the excess Br$_2$ was discharged. The mixture was filtered through a pad of Celite, and the filter cake was washed with CH$_2$Cl$_2$. The combined filtrate and washings were concentrated in vacuo. The syrupy residue was diluted with AcOEt—PhMe (2:1, 120 ml), washed with sat. Na$_2$S$_2$O$_3$ aq. solution (×2), sat. NaHCO$_3$ aq. solution (×1), and sat. NaCl aq. solution, dried (MgSO$_4$), and concentrated in vacuo to give a white solid (2.96 g). This was recrystallized from AcOEt-n-hexane to give title compound (2.44 g, 88% in 2 steps from (2S*,3S*,4R*,5R*)-1-benzyloxycarbonyl-3-[N-(t-butoxycarbonyl)amino]-4-hydroxymethyl-5-methyl-2-phenylpyrrolidine) as white powders. mp 147–148 C.; IR$_{max}$ (nujol): 3310(s), 1728(s), 1701(s, shoulder), 1690(vs), 1537 (s), 1535(s), 1280(m), 1165(m), 750(m), 700(s) cm$^{-1}$; $^1$H-NMR δ: 7.52–7.15(m, 9H), 7.05(br.s, 1H), 5.28(br.d, J=8.1 Hz, 1H), 5.05(br.s, 2H), 4.60(ddd, J=11.7, 8.8, 8.1 Hz, 1H), 4.35–4.17(m, 1H), 4.02(br.d, J=8.8 Hz, 1H), 3.71(s, 3H), 2.58(dd, J=11.7, 9.9 Hz, 1H), 1.62(br.d, J=5.5 Hz, 3H), 1.39(s, 9H) ppm.

(23) (2S*,3S*,4R*,5R*)-3-Amino-1-benzyloxycarbonyl-4-methoxycarbonyl]-5-methyl-2-phenylpyrrolidine Hydrogen chloride, Methanol reagent 10 (Tokyo Kasei, 25 ml) was added to (2S*,3S*,4R*,5R*)-1-benzyloxycarbonyl-3-[N-(t-butoxycarbonyl)amino]-4-methoxycarbonyl-5-methyl-2-phenylpyrrolidine (1.25 g, 2.67 mmol) at room temperature. The resulting heterogeneous mixture was stirred and heated at reflux; the reaction mixture became homogeneous as the inner temperature increased, and then white solids precipitated. After 15 minutes, the solvent MeOH was evaporated in vacuo. To the solid residue was added 10% NaOH aq. solution until the resulting mixture became basic (pH 10–11). This was extracted AcOEt (×4). The combined AcOEt extracts were washed with sat. NaCl aq. solution (×1), dried (Na$_2$SO$_4$), and concentrated in vacuo to give crude title compound (0.93 g, 95%) as yellow viscous oil: IR$_{max}$ (film): 3395(m), 3320(w), 1730(vs), 1700(vs), 1605(w), 1585(w), 1495(s), 1210(s), 1165(s), 1105(s), 1025(s), 745(s), 700(s) cm$^{-1}$; $^1$H-NMR δ: 7.46–7.18(m, 9H), 7.07(br.s, 1H), 5.08(d, J=8.4 Hz, 1H), 5.06(br.s, 2H), 4.13(dq, J=9.7, 6.1 Hz, 1H), 3.85 (dd, J=11.0, 8.4 Hz, 1H), 3.75(s, 3H), 2.51(dd, J=11.0, 9.7

Hz, 1H), 1.64(br.d, J=6.1 Hz, 3H), 1.27(br.s, 2H; NH$_2$) ppm. This was employed in the next step without further purification.

(24) (2S*,3S*,4R*,5R*)-1-Benzyloxycarbonyl-3-[N-(5-isopropyl-2-methoxybenzyl)amino]-4-methoxycarbonyl-5-methyl-2-phenylpyrrolidine To a stirred solution of (2S*,3S*,4R*,5R*)-3-amino-1-benzyloxycarbonyl-4-methoxycarbonyl-5-methyl-2-phenylpyrrolidine (0.93 g, 2.52 mmol) in dry CH$_2$Cl$_2$ (20 ml) was added a solution of 5-isopropyl-2-methoxybenzaldehyde (0.56 g, 3.15 mmol) in dry CH$_2$Cl$_2$ (5 ml) at room temperature. To this was added NaBH(OAc)$_3$ (0.80 g, 3.78 mmol) portionwise at room temperature. The added NaBH(OAc)$_3$ dissolved gradually with stirring at room temperature. After stirring for 1.5 hours at room temperature, the reaction mixture was basified to pH 10–11 by adding 10% NaOH aq. solution with ice-cooling. The layers were separated, and the aqueous layer was extracted with CHCl$_3$ (×3). The combined CH$_2$Cl$_2$ layer and CHCl$_3$ extracts were washed with sat. NaCl aq. solution (×1), dried (Na$_2$SO$_4$—K$_2$CO$_3$), and concentrated in vacuo to give a yellow viscous oil (1.69 g). This was chromatographed over SiO$_2$ (Merck Kieselgel 60, 20 g). Elution with n-hexane-AcOEt (30: 1) followed by CH$_2$Cl$_2$—MeOH (200:1) gave title compound (1.36 g, quant.) as a pale yellow viscous oil: IR$_{max}$ (film): 3350(w), 1735(s), 1700(vs), 1487(s), 1290(s), 1250(s), 1030(s), 810(s), 735(s), 700(s) cm$^{-1}$; $^1$H-NMR δ: 7.50–7.15(m, 10H), 7.03(dd, J=8.4, 2.2 Hz, 1H), 6.96(d, J=2.2 Hz, 1H), 6.70(d, J=8.4 Hz, 1H), 5.15(br.d, J=7.7 Hz, 1H), 5.03(br.s, 2H), 4.22–4.06(m, 1H), 3.84–3.58(m, 3H), 3.71(s, 3H), 3.64(s, 3H), 2.90–2.58 (m, 2H), 1.61(br.d, J=5.5 Hz, 3H), 1.19(d, J=7.0 Hz, 6H) ppm.

(25) (2S*,3S*,4R*,5R*)-3-[N-(-Isopropyl-2-methoxybenzyl)amino]4-methoxycarbonyl-5-methyl-2-phenylpyrrolidine 20% Pd(OH)$_2$—C (Pearlman's catalyst, Aldrich; 0.81 g) was added to a solution of (2S*,3S*,4R*,5R*)-1-benzyloxycarbonyl-3-[N-(5-isopropyl-2-methoxybenzyl) amino]-4-methoxycarbonyl-5-methyl-2-phenylpyrrolidine (1.36 g, 2.57 mmol) and HCO$_2$NH$_4$ (0.97 g, 15.4 mmol) in MeOH (30 ml). The reaction mixture was stirred and heated at a gentle reflux for 30 minutes. The catalysts were filtered off by the aid of a Celite pad, and washed with MeOH. The combined filtrate and washings were concentrated in vacuo. The syrupy residue was basified to pH 10 with 1M NaOH aq. solution, and extracted with CH$_2$Cl$_2$ (×3). The combined CH$_2$Cl$_2$ extracts were washed with sat. NaCl aq. solution, dried (Na$_2$SO$_4$), and concentrated in vacuo to give a pale yellow viscous oil (0.94 g). This was chromatographed over SiO$_2$ (Merck Kieselgel 60, 13.0 g). Elution with n-hexane-AcOEt (20:1→10:1→5:1) followed by CH$_2$Cl$_2$—MeOH (60:1) gave title compound (0.73 g, 72%) as a pale yellow viscous oil: IR$_{max}$ (film): 3330(w), 1728(s), 1610(m), 1500 (s), 1250(s), 1170(s), 813(s), 765(m), 750(m), 740(m), 700 (s) cm$^{-1}$; $^1$H-NMR δ: 7.42–7.21(m, 5H), 7.02(dd, J=8.4, 2.2 Hz, 1H), 6.83(d, J=2.2 Hz, 1H), 6.66(d. J=8.4 Hz, 1H), 4.35(d, J=5.8 Hz, 1H), 3.75(s, 3H), 3.68(d,J=13.2 Hz, 1H), 3.56(dd,J=5.8, 3.1 Hz, 1H), 3.51(s, 3H), 3.48(dq,J=7.7, 6.2 Hz, 1H), 3.41(d, J=13.2 Hz, 1H), 2.79(sep, J=7.0 Hz, 1H), 2.60(deformed dd, J=7.7, 3.1 Hz, 1H), 1.77(br.s, 2H; NH×2), 1.44(d, J=6.2 Hz, 3H), 1.19(d, J=7.0 Hz, 6H) ppm.

(26) (2S*,3S*,4R*,5R)-3-[N-(5-Isopropyl-2-methoxybenzyl)amino]-4-methoxycarbonyl-5-methyl-2-phenylpyrrolidine fumarate Fumaric acid (58.5 mg, 0.50 mmol) was added to a solution of (2S*,3S*,4R*,5R*)-3-[N-(5-isopropyl-2-methoxybenzyl)amino]-4-methoxycarbonyl-5-methyl-2-phenylpyrrolidine (0.20 g, 0.50 mmol) in EtOH. The resulting heterogeneous mixture was sonicated to allow complete salt formation. The crystalline salts thus generated were dissolved in a minimum volume of EtOH with heating at reflux, and recrystallized on cooling to room temperature. After keeping in a refrigerator overnight, the white crystals were filtered off, washed with Et$_2$O—EtOH (20:1, ×1), dried in vacuo at 40 C. to give the title fumarate (0.20 g, 85%) as white powders. An additional amount of the title compound (0.02 g, 8%) was obtained as a second crop by crystallization of the mother liquor from EtOH—Et$_2$O; the total yield of the title compound amounted to 0.24 g (93%): mp 169.0–171.0 (white powders); IR$_{max}$ (nujol): 3330(s), 3000–2100(br., s), 1735(s), 1710(s), 1653(m), 1603(s), 1240(s), 1178(s), 818 (s), 788(m), 768(s), 743(s), 700(s) cm$^{-1}$; $^1$H-NMR δ (DMSO-d$_6$): 7.47–7.30)m, 4H), 7.35–7.21(m, 1H), 7.00(dd, J=8.4, 2.0 Hz, 1H), 6.79(d, J=2.0 Hz, 1H), 6.76(d, J=8.4 Hz, 1H), 6.59(s, 2H), 4.29(d, J=6.2 Hz, 1H), 4.15–3.10(m, 8H), 3.67(s, 3H), 3.54(s, 3H), 2.73(sep, J=7.0 Hz, 1H), 2.60–2.50 (m, 1H), 1.30(d, J=6.2 Hz, 3H), 1.12(d, J=7.0 Hz, 6H) ppm.

(27) (2S*,3S*,4R,5R*)-4-Carboxy-3-[N-(5-isopropyl-2-methoxybenzyl)amino]-5-methyl-2-phenylpyrrolidine dihydrochloride A solution of (2S*,3S*,4R*,5R*)-3-[N-(5-isopropyl-2-methoxybenzyl)amino]-4-methoxycarbonyl-5-methyl-2-phenylpyrrolidine (0.39 g, 0.98 mmol) in 6M HCl aq. solution (6.0 ml) was stirred and heated at a gentle reflux for 30 minutes, wherein precipitation of white solids initiated ca. 10 minutes after refluxing. The reaction mixture was cooled to room temperature, and then EtOH (4.0 ml) was added. After the mixture was ice-cooled for 30 minutes, the white precipitates were filtered off, washed with EtOH (×2), and dried in vacuo at a temperature between 40 and 50 C. for 2 days to afford title compound (0.43 g, 96%) as white needles.

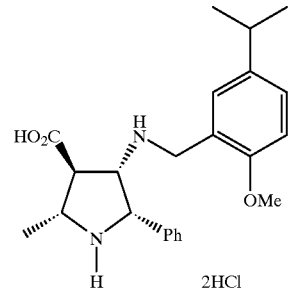

mp 159–164 C.: IR$_{max}$ (nujol): 3400(s), 3200(s), 3130(s), 2370(s), 2300(br., s), 1735(s), 1710(s), 1585(s), 1510(s), 1260(s), 1143(s), 1017(s), 830(s), 770(s), 745(s), 702(s) cm$^{-1}$; $^1$H-NMR δ (DMSO-d$_6$): 7.907.73(m, 2H), 7.60–7.45 (m, 3H), 7.25–7.13(m, 2H), 6.90(d, J=9.2 Hz, 1H), 5.35–5.15(m, 1H), 4.63–4,41(m, 1H), 4.20–4.01(m, 1H), 4.00–3.83(m, 1H), 3.803.15(m, 1H), 3.67(s, 3H), 2.79(sep, J=6.8 Hz, 1H), 2.55–2.42(m, 1H), 1.71(br.d, J=5.9 Hz, 3H), 1.15(d, J=6.8 Hz, 6H) ppm.

Example 2

(1) (2S*,3S*,4R*,5R*)1-Benzyloxycarbonyl-3-[N-(2-methoxy-5-trifluoromethoxybenzyl)amino]-4-methoxycarbonyl-5-methyl-2-phenylpyrrolidine To a stirred solution of (2S*,3S*,4S*,5R*)-3-amino-1-benzyloxycarbonyl-4-methoxycarbonyl-5-methyl-2-phenylpyrrolidine (793 mg, 2.15 mmol) and 2-methoxy-5-trifluoromethoxybenzaldehyde (569 mg, 2.58 mmol) in dry CH$_2$Cl$_2$ (10 ml) was added NaBH(OAc)$_3$ (639 mg, 3.01 mmol) portionwise at room temperature. After stirring for 2 h at room temperature, the reaction mixture was basified to pH 10–11 by adding 10% NaOH aq. solution with ice-cooling. The organic layer was separated, and the aqueous layer was extracted with $CH_2Cl_2$ (60 ml×4). The combined $CH_2Cl_2$ solution was washed with brine, dried ($MgSO_4$) and concentrated in vacuo to give crude title compound (1.32 g) as a yellow viscous oil. This was purified by column chromatography on silica gel (65 g) with hexane-ethyl acetate (3:1–2:1) to give the pure title compound (1.08 g, 88%) as a pale yellow oil.

$^1$H-NMR δ 7.42–7.17 (m, 10 H), 7.08–6.99 (m, 2H), 6.78–6.70 (m, 1H), 5.18 (br. d, J=7.7 Hz, 1H), 5.04 (br. s, 2H), 4.20–4.07 (m, 1H), 3.80–3.60 (m, 3H), 3.73 (s, 3H), 3.70 (s, 3H), 2.83–2.67 (m, 1H), 1.61 (d, J=5.9 Hz, 3H), 1.50 (br. s, 1H) ppm.

$IR_{max}$(film, $cm^{-1}$):ν 3350, 1732, 1700, 1607, 1493, 1456, 1438, 1404, 1339, 1245, 1222, 1158, 1028, 870, 810.

(2) (2S*,3S*,4S*,5R*)-3-[N-(2-methoxy-5-trifluoromethoxybenzyl)amino]-4-methoxycarbonyl-5-methyl-2-phenylpyrrolidine and (2S*,3S*,4R*,5R*)-3-[N-(2-Methoxy-5-trifluoromethoxybenzyl)amino]-4-methoxycarbonyl-5-methyl-2-phenylpyrrolidine 20% $Pd(OH)_2$—C (Pearlman's cat., 600 mg) was added to a solution of (2S*,3S*,4S*,5R*)-1-benzyloxycarbonyl-3-[N-(2-methoxy-5-trifluoromethoxybenzyl)amino]-4-methoxycarbonyl-5-methyl-2-phenylpyrrolidine 1.08 g, 1.89 mmol) and $HCO_2NH_4$ (714 mg, 11.3 mmol) in methanol (25 ml). The reaction mixture was stirred and heated at a gentle reflux for 30 min. The catalyst was filtered off by the aid of a Celite pad, and washed with MeOH. The combined filtrate and washings were concentrated in vacuo. The residue was basified to pH 10–11 with 10% NaOH aq. solution, and extracted with $CH_2Cl_2$ (60 ml×4). The combined $CH_2Cl_2$ extracts were washed with brine, dried ($MgSO_4$) and concentrated in vacuo to give a crude mixture of (2S*,3S*,4R*,5R*)-3-[N-(2-methoxy-5-trifluoromethoxybenzyl)amino]-4-methoxycarbonyl-5-methyl-2-phenylpyrrolidine and (2S*,3S*,4R*,5R*)-3-[N-(2-methoxy-5-trifluoromethoxybenzyl)amino]-4-methoxycarbonyl-5-methyl-2-phenylpyrrolidine (794 mg) as a yellow oil. This was purified by column chromatography on silica gel (45 g) with hexane-ethyl acetate (1:1) to give (2S*,3S*,4S*,5R*)-3-[N-(2-methoxy-5-trifluoromethoxybenzyl)amino]-4-methoxycarbonyl-5-methyl-2-phenylpyrrolidine (222 mg, 27.3%) as a pale yellow solid, which was recrystallized from hexane-ethyl acetate to give (2S*,3S*,4S*,5R*)-3-[N-(2-methoxy-5-trifluoromethoxybenzyl)-amino]-4-methoxycarbonyl-5-methyl-2-phenylpyrrolidine (127 mg, 1st crop) as a white solid: mp 81–82° C.

$^1$H-NMR δ 7.38–7.21 (m, 5H), 7.03 (dd, J=2.6, 8.8 Hz, 1H), 6.90 (d, J=2.6 Hz, 1H), 6.70 (d, J=8.8 Hz, 1H), 4.36 (d, J=5.9 Hz, 1H), 3.75 (s, 3H), 3.65 (d, J=14.5 Hz, 1H), 3.56 (s, 3H), 3.58–3.37 (m, 1H), 3.50 (dd, J=3.3, 5.9 Hz, 1H), 3.40 (d, J=14.5 Hz, 1H), 2.55 (dd, J=3.3, 7.7 Hz, 1H), 1.85 (br. s, 2H), 1.43 (d, J=6.2 Hz, 3H) ppm.

IR (KBr, $cm^{-1}$):ν 3450, 1727, 1497, 1459, 1438, 1313, 1263, 1251, 1222, 1164, 1040, 885, 822.

Further elution with $CH_2Cl_2$—MeOH (20:1) gave (2S*,3S*,4R*,5R*)-3-[N-(2-methoxy-5-trifluoromethoxybenzyl) amino]-4-methoxycarbonyl-5-methyl-2-phenylpyrrolidine (342 mg, 41.4%) as a yellow oil.

$^1$H-NMR δ 7.40–7.25 (m, 5H), 7.02 (dd, J=2.8, 8.7 Hz, 1H), 6.87 (d, J=2.8 Hz, 1H), 6.69 (d, J=8.7 Hz, 1H), 4.09 (d, J=7.7 Hz, 1H), 3.75–3.52 (m, 4H), 3.71 (s, 3H), 3.67 (s, 3H), 2.60 (t, J=8.1 Hz, 1H), 1.95 (br. s, 2H), 1.30 (d, J=6.2 Hz, 3H) ppm.

IR (film, $cm^{-1}$):ν 3340, 1728, 1496, 1456, 1438, 1251, 1225, 1167, 1031, 700.

(3) (2S*,3S*, 4R*,5R*)-4-Carboxy-3-[N-(2-Methoxy-5-trifluoromethoxybenzyl)amino]5-methyl-2-phenylpyrrolidine dihydrochloride A solution of (2S*,3S*,4R*,5R*)-3-[N-(2-methoxy-5-trifluoromethoxybenzyl)amino]-4-methoxycarbonyl-5-methyl-2-phenylpyrrolidine (110 mg, 0.25 mmol) in 6M HCl aq. solution (2 ml) was stirred and heated at a gentle reflux for 30 min. After the reaction mixture was cooled to room temperature, precipitation of white solids initiated. The mixture was diluted with ethanol (1.5 ml) and ice-cooled for 1 h. The precipitated white solid was filtered off to give title compound (105 mg, 84.1%) as a white needle: mp 155–159 ° C.

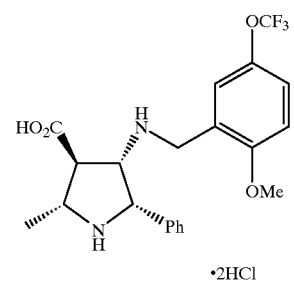

$^1$H-NMR (DMSO-$d_6$) δ 11.27 (br. s, 1H), 10.04 (br. s, 1H), 7.86–7.78 (m, 2H), 7.56–7.33 (m, 5H), 7.09 (d, J=8.8 Hz, 1H), 5.28 (br. s, 1H), 4.54 (br. s, 1H), 4.28–4.11 (m, 2H), 4.00–3.40 (m, 7H), 1.73 (d, J=6.6 Hz, 3H) ppm.

IR (KBr, $cm^{-1}$):ν 3420, 1708, 1585, 1503, 1455, 1257, 1232, 1212, 1173, 1014, 768.

(4) (2S*,3S*,4R*,5R*)-4-Carboxy-3-[N-(2-methoxy-5-trifluoromethoxybenzyl)amino]-5-methyl-2-phenylpyrrolidine dihydrochloride A solution of (2S,3S*,4R*,5R*)-3-[N-(2-methoxy-5-trifluoromethoxybenzyl)amino]-4-methoxycarbonyl-5-methyl-2-phenylpyrrolidine (162 mg, 0.37 mmol) in 6M HCl aq. solution (2.5 ml) was stirred and heated at a gentle reflux for 30 min. The reaction mixture was cooled to room temperature and the solvent was evaporated in vacuo to give crude title compound as a dark red amorphous solid. This was recrystallized from ethanol-ether to give the pure title compound (133 mg, 72.5%) as a white solid. mp 137–140 ° C.

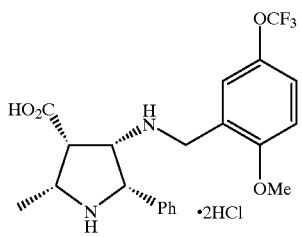

$^1$H-NMR (DMSO-$d_6$) δ 10.38 (br. s, 1H), 7.66–7.57 (m, 2H), 7.55–7.44 (m, 3H), 7.42–7.29 (m, 2H), 7.10 (d, J=8.8 Hz, 1H), 5.35 (br. s, 1H), 4.45 (br. s, 1H), 4.15–3.95 (m, 3H), 3.77 (s, 3H), 3.60–3.30 (m, 1H), 1.60 (d, J=6.2 Hz, 3H) ppm.

IR (KBr, $cm^{-1}$):ν 3430, 2950, 1733, 1620, 1577, 1504, 1462, 1259, 1213, 1177, 1159, 1025, 820, 764, 700.

Example 3

(1) 2-(4-Methylbenzyloxy)methyl-2-propenol

A mixture of p-anisaldehyde (17.31 g, 0.127 mol), 2-methylene-1,3-propanediol (14.00 g, 0.159 mol), and p-TsOH $H_2O$ (121 mg, 0.64 mmol) in dry PhH (100 ml) was stirred and heated at reflux, and the water generated was azeotropically removed in a theoretical amount using a Dean-Stark apparatus. After 70 ml of PhH was distilled off, the resultant red PhH solution containing 2-(4-methoxyphenyl)-5-methylene-1,3-dioxane was cooled with salt-ice, and a solution of diisobutylaluminum hydride (DIBAL-H) in PhMe (1.02M, 100 ml and 1.50M, 67.0 ml; total 0.203 mol) was added dropwise under an atmosphere of $N_2$; at the point when 20 ml of the PhMe solution of DIBAL-H was added, the reaction mixture changed from deep red to light yellow. After the addition was complete, the reaction mixture was allowed to stirr at room temperature overnight. The reaction mixture was ice-cooled, and MeOH (23 ml) was added carefully. $H_2O$ (12 ml) was, then, added dropwise, wherein the mixture became thick and gelatinous, and finally granular. After the stirring was continued at room temperature for an hour, the mixture was filtered through a pad of Celite. The filter cake was washed with PhMe thoroughly. The combined filtrate and washings were dried ($MgSO_4$), and concentrated in vacuo at a bath temperature of 65 C. to give a pale yellow oil (24.88 g). This was distilled in vacuo to give title compound (18.52 g, 70.1%) as a colorless oil. bp 123–147 C./0.80–0.90 mm; $IR_{max}$ (film): 3420(s), 1615(s), 1515(s), 1250(s), 1070(s), 1035(s), 918 (m), 820(s) $cm^{-1}$; $^1$H-NMR δ: 7.26(d, J=8.8 Hz, 2H), 6.88(d, J=8.8 Hz, 2H), 5.19(br.s, 1H), 5.14(br.s, 1H), 4.45(s, 2H), 4.19(s, 2H), 4.07(s, 2H), 3.81(s, 3H), 1.98(br.s., 1H) ppm.

(2) 3-Bromo-2-[-(4-methoxybenzoyloxy)methyl]propene

To a stirred solution of 2-(4-methylbenzyloxy)methyl-2-propenol (21.48 g, 103.1 mmol) and $Ph_3P$ (32.45 g, 123.72 mmol) in dry $CH_2Cl_2$ (200 ml) was added N-bromosuccinimide (NBS, 20.19 g, 113.41 mmol) portionwise with cooling in a salt-ice bath. The reaction mixture was stirred under the same cooling conditions for an hour, and it became turbid with stirring. To the resultant white slurry were added $Ph_3P$ (20.83 g, 79.40 mmol) and NBS (12.85 g, 72.18 mmol) successively, and the stirring was continued with salt-ice-cooling for additional 50 minutes, which led to the yellow reaction mixture. MeOH (3.34 ml, d0.791, 82.5 mmol) was added dropwise to destroy the excess reagents. After stirring with salt-ice-cooling for 40 minutes, the mixture was washed with sat. $NaHCO_3$ aq. solution (40 ml×2), and sat. NaCl aq. solution (40 ml×1). This dark green $CH_2Cl_2$ solution was dried ($MgSO_4$), and concentrated in vacuo to give a dark brown solid (100 g). This was extracted with exhaustively with ice-chilled n-hexane-$Et_2O$ (10:1). The combined extracts were filtered through a short pad of Celite, and the filtrate was, then, concentrated in vacuo to give title compound (20.59 g, 73.5%) as a colorless oil. The solid residue was further extracted with n-hexane-$Et_2O$ (4:1, 100 ml×5), and the combined extracts were filtered through a pad of Celite. The filtrate was concentrated in vacuo to give a solid white residue, which was extracted with ice-chilled n-hexane. The combined n-hexane extracts were filtered through a pad of Celite, and the filtrate was concentrated in vacuo to give an additional amount of title compound (1.84 g, 6.6%) as a colorless oil; a total yield: 22.43 g, 80.1%. $IR_{max}$ (film): 1653(w), 1613(s), 1510(s), 1250(s), 1090(s), 1035(s), 912 (s), 819(s) $cm^{-1}$; $^1$H-NMR δ: 7.28(d, J=8.8 Hz, 2H), 6.89(d, J=8.8 Hz, 2H), 5.35(d, J=1.1 Hz, 1H), 5.34(s, 1H), 4.46(s, 2H), 4.12(s, 2H), 4.04(s, 2H), 3.81(s, 3H) ppm. This was employed in the next step without further purification.

(3) (3S*,4R*)-1-tert-Butyldimethylsilyl-3-[2-(4-methoxybenzoyloxy)methyl-2-propenyl]4-phenyl-2-azetidinone Under an atmosphere of $N_2$, a 1.5M solution of $LiN(Pr^i)_2$ THF in c-$C_6H_6$ (Aldrich; 43.9 ml, 65.9 mmol) was added dropwise to a stirred solution of 1-tert-butyldimethylsilyl-4-phenyl-2-azetidinone (13.24 g, 50.64 mmol) in dry THF (230 ml) at an inner temperature between −78 and −73 C. After stirring at −78 C for 30 minutes, the reaction mixture became a white slurry. A solution of 3-bromo-2-[(4-methoxybenzoyloxy)methyl]propene (14.69 g, 54.18 mmol) in dry THF (30.0 ml) was added dropwise at an inner temperature between −78 and −71 C. After the addition was complete, the dropping funnel used was rinsed with dry THF (5 ml×2). The resultant homogeneous reaction mixture was stirred at −78 C. for an hour, and then at −10 C. for 50 minutes. The reaction was quenched by adding sat. $NH_4Cl$ aq. solution (30.0 ml) below 0 C. The mixture was taken up in AcOEt (500 ml). The AcOEt solution separated was washed with sat. NaCl aq. solution (100 ml×2), dried ($MgSO_4$), and concentrated in vacuo to give a heterogeneous yellow oil (26.51 g). This was, then, diluted with $Et_2O$ (250 ml), washed with $H_2O$ (×2), and sat. NaCl aq. solution (×1), dried ($MgSO_4$), and concentrated in vacuo to give a homogeneous yellow oil (24.91 g). This was flash chromatographed over $SiO_2$ (Merck Kieselgel 60, 250 g). Elution with n-hexane-AcOEt (40:1/30:1/20:1/10:1) gave title compound (19.73 g, 86.3%) as a viscous pale yellow oil. $IR_{max}$ (film): 1745(s), 1645(m), 1610(m), 1510(m), 990(shoulder, m), 910(m), 775(m), 745(w), 700(m), 680(m) $cm^{-1}$; $^1$H-NMR δ: 7.40–7.25(m, 5H), 7.20(d, J=8.8 Hz, 2H), 6.85(d, J=8.8 Hz, 2H), 5.05(s, 1H), 4.84(s, 1H), 4.35(s, 2H), 4.20(d, J=2.6 Hz, 1H), 3.86(s, 2H), 3.80(s, 3H), 3.25(ddd, J=10.5, 5.1, 2.6 Hz, 1H), 2.70(dd, J=15.7, 5.1 Hz, 1H), 2.48(dd, J=15.7, 10.7 Hz, 1H), 0.92(s, 9H), 0.21(s, 3H), −0.21(s, 3H) ppm.

(4) (3S*,4R*)-1-tert-Butyldimethylsilyl-3-(2-hydroxymethyl-2-propenyl)-4-phenyl-2-azetidinone To a stirred mixture of (3S*,4R*)-1-tert-Butyldimethylsilyl-3-[2-(4-methoxybenzoyloxy)methyl-2-propenyl]-4-phenyl-2-azetidinone (18.74 g, 41.5 mmol), pH7 phosphate buffer (15.0 ml), and $CH_2Cl_2$ (250 ml) was added 2,3-dichloro-5.6-dicyano-1,4-benzoquinone (DDQ, 15.1 g, 66.4 mmol) portionwise at room temperature; on the addition, the reaction mixture became dark green, and then red solids precipitated with stirring. (In the course of addition, a slight heat evolution was observed.) The stirring was continued at room temperature for two hours, the reaction being monitored by TLC[Merck Kieselgel 60, n-hexane-AcOEt (3:1)]. sat. $NaHCO_3$ aq. solution (80.0 ml) was added to quench the reaction, wherein gas evolution was observed. After Celite was added, the mixture was filtered through a pad of Celite, and the filter cake was washed with $CH_2Cl_2$. The combined filtrate and $CH_2Cl_2$ washings were washed with sat. $NaHCO_3$ aq. solution (×2), and dried ($MgSO_4$). The combined aqueous washings were filtered through a pad of Celite, and the filter cake was washed with $CH_2Cl_2$. From the combined filtrate and washings, the $CH_2Cl_2$ layer was separated, and the aqueous layer was extracted with $CH_2Cl_2$ (100 ml×3). The combined $CH_2Cl_2$ layer and washings were dried ($MgSO_4$). The $CH_2Cl_2$ solution dried were combined, treated with activated charcoal, and concentrated in vacuo to give an orange oil (22.1 g). This was flash chromatographed over $SiO_2$ (Merck Kieselgel 60, 200 g). Elution with n-hexane-AcOEt (15:1/5:1/3:1) gave title compound (11.18 g, 81.2%) as a viscous pale yellow oil. $IR_{max}$ (film): 3420(s), 1750(s), 1733(s), 1718(s), 1705(s), 1650(m), 1040(s), 900(s), 775(s) 700(s) cm$^{-1}$; $^1$H-NMR δ: 7.43–7.25(m, 5H), 5.04(br.s, 1H), 4.82(br.s, 1H), 4.20(d, J=2.2 Hz, 1H), 4.06(br.s, 2H), 3.26(ddd, J=8.2, 7.0, 2.2 Hz, 1H), 2.67(dd, J=15.2, 7.0 Hz, 1H), 2.54(dd, J=15.2, 8.2 Hz, 1H), 2.42(br.s, 1H, OH), 0.92(s, 9H), 0.21(s, 3H), −0.19(s, 3H) ppm.

(5) (3S*,4R*)-1-tert-Butyldimethylsilyl-3-(2-chloromethyl-2-propenyl)-4-phenyl-2-azetidinone To a stirred and ice-cooled slurry of (3S*,4R*)-1-tert-Butyldimethylsilyl-3-(2-hydroxymethyl-2-propenyl)-4-phenyl-2-azetidinone (13.66 g, 41.0 mmol), 2,6-lutidine (15.3 ml, d0.920, 123 mmol), and LiCl (anhydros, 4.37 g, 103 mmol) in DMF (103 ml) was added MeSO$_2$Cl (MsCl, 7.93 ml, d1.480, 103 mmol) dropwise under an atmosphere of N$_2$. After the reaction mixture was stirred with ice-cooling for 5 hours and 50 minutes, H$_2$O (40 ml) was added. The stirring was continued at room temperature for additional 20 minutes to destroy the excess MsCl. The resultant dark red mixture was poured into H$_2$O (70 ml). The mixture was extracted with Et$_2$O (70 ml×5). The combined Et$_2$O extracts were washed with H$_2$O (×3), sat. NaHCO$_3$ aq. solution (×1), and sat. NaCl aq. solution (×1), dried (MgSO$_4$), treated with activated charcoal, and concentrated in vacuo to give practically pure title compound (15.36 g, quantitative) as a pale yellow oil. IR$_{max}$ (film): 1735(v.s), 1650(w), 1175(s), 825(s), 750(s), 700(s) cm$^{-1}$; $^1$H-NMR δ: 7.43–7.25(m, 5H), 5.14 (br.s, 1H), 4.87(br.s, 1H), 4.22(d, J=2.6 Hz, 1H), 3.99(s, 2H), 3.25(ddd, J=10.1, 5.1, 2.6 Hz, 1H), 2.78(dd, J=16.1, 5.1 Hz, 1H), 2.60(dd, J=16.1, 10.1 Hz, 1H), 0.92(s, 9H), 0.22(s, 3H), −0.20(s, 3H) ppm. This was employed in the next step without further purification.

(6) (2R*,3S*)-3-Methoxycarbonyl-5-methlene-2-phenylpiperidine

A homogeneous mixture of (3S*,4R*)-1-tert-butyldimethylsilyl-3-(2-chloromethyl-2-propenyl)-4-phenyl-2-azetidinone (12.98 g, 33.8 mmol) and Hydrogen Chloride, Methanol Reagent 10 (Tokyo Kasei, 150 ml) was stirred and heated at reflux for an hour. The mixture was concentrated in vacuo. The syrupy dark orange residue was ice-cooled, and then basified with sat. Na$_2$CO$_3$ aq. (ca. 50 ml) to pH 9–10. The mixture was extracted with AcOEt (50 ml×5). The combined AcOEt extracts were dried (Na$_2$SO$_4$), and concentrated in vacuo to give a yellow semisolid (9.74 g). To this were added NaI (7.60 g, 50.7 mmol), NaHCO$_3$ (8.52 g, 101 mmol), and DMF (70 ml), and the resultant mixture was stirred and heated at a bath temperature of 160 C. for 15 minutes. After the mixture was allowed to cool to room temperature, sat. Na$_2$CO$_3$ aq. solution (70 ml) was added, and the insoluble inorganic materials were filtered off by the aid of Celite. The filter cake was washed with AcOEt—PhMe (2:1, ×3). From the combined filtrate and washings was separated the AcOEt—PhMe layer, and the aqueous layer was extracted with AcOEt—PhMe (2:1, 30 ml×5). The combined AcOEt—PhMe layer and extracts were washed with H$_2$O (40 ml×3), and sat. NaCl aq. solution (40 ml×1), dried (Na$_2$SO$_4$), and concentrated in vacuo at a bath temperature below 70 C. to give practically pure title compound (7.66 g, overall 98.0% from (3S*,4R*)-1-tert-butyldimethylsilyl-3-(2-chloromethyl-2-propenyl)-4-phenyl-2-azetidinone) as a red orange oil. IR$_{max}$ (film): 3320(w), 1728(s), 1650(w), 1165(s), 900(m), 738(m), 698(s) cm$^{-1}$; $^1$H-NMR δ: 7.41–7.14(m, 5H), 4.88(br.s, 1H), 4.75 (br.s, 1H), 4.09(d, J=2.9 Hz, 1H), 3.68(br.d, J=14.0 Hz, 1H), 3.45(s, 3H), 3.43(br.d,J=14.0 Hz, 1H), 3.23–3.14(m, 1H), 2.83–2.62(m, 1H), 1.78(br.s, 1H, NH) ppm. This was employed in the next step without further purification.

(7) (2R*,3S*)-3-Methoxycarbonyl-5-methlene-2-phenylpiperidine

To a stirred mixture of crude (2R*,3S*)-3-methoxycarbonyl-5-methlene-2-phenylpiperidine (8.58 g, 37.1 mmol), NaHCO$_3$ (6.23 g, 74.2 mmol), and H$_2$O (75.0 ml) was added a solution of di-tert-butyl dicarbonate [(Boc)$_2$O, 9.72 g, 44.5 mmol) in THF (5.0 ml); on the addition, CO$_2$ gas evolved violently. The resultant pale yellow mixture was stirred at room temperature for 3 hours, and then extracted with AcOEt (70 ml×3). The combined AcOEt extracts were washed with sat. NaCl aq. solution (×1), dried (MgSO$_4$), and concentrated in vacuo to give an orange oil (14.35 g). This was flash chromatographed over SiO$_2$ (Merck Kieselgel 60, 150 g). Elution with n-hexane-AcOEt (50:1/20:1) gave title compound (11.91 g, 96.9%) as a relatively unstable, almost colorless oil. IR$_{max}$ (film): 1735 (s), 1697(s), 1685(s), 1650(shoulder, m), 1170(s), 895(s), 765(m), 700(s) cm$^{-1}$; $^1$H-NMR δ: 7.36–7.17(m, 5H), 4.95 (br.s, 1H), 4.89(br.s, 1H), 4.40–4.20(m,1H), 3.80–3.35(m, 2H), 3.63(s, 3H), 3.14–3.03(m, 1H), 2.84–2.57(m, 2H), 1.42(br.s, 9H) ppm.

(8) A mixture of (2R*,3S*,5S*)- and (2R*,3S*,5R*)-1-tert-Butoxycarbonyl-5-hydroxymethyl-3-methoxycarbonyl-2-phenylpiperidine To a stirred solution of (2R*,3S*)-3-methoxycarbonyl-5-methylene-2-phenylpiperidine (9.90 g, 29.9 mmol) and (Ph$_3$P)$_3$RhCl (1.38 g, 1.50 mmol) in dry THF (150 ml) was added a 1.0M solution of catecholborane in THF (Aldrich, 89.7 ml, 89.7 mmol) dropwise at room temperature under an atmosphere of N$_2$. The resultant dark red reaction mixture was allowed to stir at room temperature for 2.5 hours. The mixture was ice-cooled, and then MeOH (150 ml) was added carefully. 5% NaHCO$_3$ aq. solution (60.0 ml, 35.7 mmol) and 30% H$_2$O$_2$ aq. solution (99.0 ml, 874 mmol) were added successively, and the black mixture was stirred with ice-cooling for 1.5 hours. This was concentrated in vacuo at a bath temperature between 40 and 50 C. The aqueous residue was extracted with AcOEt (70 ml×5). The combined AcOEt extracts were washed with ice-chilled 1.0M NaOH aq. solution (×4), and sat. NaCl aq. solution (×1), dried (MgSO$_4$), treated with activated charcoal, and concentrated in vacuo to give a dark red syrup (11.42 g). This was flash chromatographed over SiO, (Merck Kieselgel 60, 120 g). Elution with n-hexane-AcOEt (10:1/5:1/3:1) gave a mixture of title compounds (9.17 g, 87.8%) as a viscous pale orange oil. IR$_{max}$ (film): 3450(s), 1730(s), 1680(br., s), 1290(br., s), 1150(br., s), 1040(s), 765(w), 738(m), 700(s) cm$^{-1}$; $^1$H-NMR δ: in part, 3.61(s, 3H, CO$_2$CH$_3$), 1.53, 1.50, and 1.48(each s, total 9H, NCO$_2$C$_4$H$_9$t) ppm.

(9) A mixture of (2R*,3S*,5S*)- and (2R*,3S*,5R*)-5-Hydroxymethyl-3-methoxycarbonyl-2-phenylpiperidine A mixture of (2R*,3S*,5S*)- and (2R*,3S*,5R*)-1-tert-Butoxycarbonyl-5-hydroxymethyl-3-methoxycarbonyl-2-phenylpiperidine (19.31 g, 55.26 mmol) was dissolved in MeOH (50 ml), and Hydrogen Chloride, Methanol Reagent 10 (Tokyo Kasei, 50 ml) was added at room temperature. After the resultant solution was stirred and heated at a gentle reflux for 1.5 hours, an additional amount of Hydrogen Chloride, Methanol Reagent 10 (Tokyo Kasei, 100 ml) was added. The stirring was continued with heating at reflux for an hour. The bright yellow reaction mixture was, then, concentrated in vacuo. The residue was ice-cooled, and basified with sat. Na$_2$CO$_3$ aq. solution to pH9–10. The inorganic precipitates were filtered off by the aid of Celite, and the filter cake was washed with CH$_2$Cl$_2$. From the combined filtrate and washings was separated the CH$_2$Cl$_2$ layer, and the aqueous layer was extracted with CH$_2$Cl$_2$. The combined CH$_2$Cl$_2$ layer and extracts were dried (Na$_2$SO$_4$), and concentrated in vacuo to give a mixture of title compounds (12.89 g, 93.5%) as a dark red oil. IR$_{max}$ (film): 3320(s), 1720(s), 1605(w), 1497(m), 1195(s), 1170(s), 740 (m), 700(s) cm$^{-1}$; $^1$H-NMR δ: 7.40–7.16(m, 5H), 4.40(d, J=5.1H, 0.33H), 3.90(d, J=3.7 Hz, 0.67H), 3.60(d, J=6.6 Hz, 0.66H), 3.52–3.40(m, 0.67H), 3.49(d,J=4.8 Hz, 1.34H), 3.48 (s, 1H), 3.41(s, 2H), 3.10–2.99(m, 1H), 2.93(dd, J=12.6, 4.0 Hz, 0.33H), 2.72(dd, J=12.6, 7.7 Hz, 0.33H), 2.53(dd, J=12.8, 11.4 Hz, 0.67H), 2.25–1.93(m, 4H), 1.93–1.76(m, 0.33H), 1.65(ddd, J=14.3, 14.3, 5.4 Hz, 0.67H) ppm. This was employed in the next step without further purification.

(10) (2R*,3S*,5S*)- and (2R*,3S*,5R*)-5-(tert-Butyldimethylsilyloxy)-methyl-3-methoxycarbonyl-2-phenylpiperidine A mixture of (2R*,3S*,5S*)- and (2R*,3S*,5R*)-5-hydroxymethyl-3-methoxycarbonyl-2-phenylpiperidine (12.89 g, 51.70 mmol) was dissolved in DMF (30 ml), and imidazole (8.80 g, 129.3 mmol) and TBDMS-Cl (9.35 g, 62.0 mmol) were added portionwise successively at room temperature; on the addition of TBDMS-Cl, there took place heat evolution. After stirring, at room temperature for 3 hours, the dark yellow reaction mixture was diluted with AcOEt—PhMe (2:1, 300 ml), washed with H$_2$O (30 ml ×3), and sat. NaCl aq. solution (×1), dried (Na$_2$SO$_4$), and concentrated in vacuo to give an orange oil (18.36 g). This was flash chromatographed over SiO$_2$ (Merck Kieselgel 60, 320 g). Elution with CH$_2$Cl$_2$—MeOH (600:1/500:1/400:1/300:1/200:1) gave (2R*,3S*,5S*)-title compound (11.46 g, 61.0%) as a pale yellow oil. IR$_{max}$ (film): 3320(w), 1725(s), 1605(w), 1495(w), 1250(s), 1165(s), 1105(s), 838(s), 775 (m), 698(m) cm$^{-1}$; $^1$H-NMR 5: 7.35–7. 17(m, 5H), 3.88(d, J=3.3 Hz, 1H), 3.53–3.34(m, 2H), 3.45(dd, J=11.5, 5.5 Hz, 1H), 3.42(s, 3H), 3.13–3.01(m, 1H), 2.54(dd, J=13.2, 11.5 Hz, 1H), 2.18–2.00(m, 2H), 1.80–1.60(m, 2H), 0.90(s, 9H), 0.05(s, 6H) ppm. Further elution with CH$_2$Cl$_2$—MeOH (200:1/100:1/80:1/40:1) gave (2R*,3S*,5R*)-title compound (4.86 g, 25.9%) as a pale yellow oil. IR$_{max}$ (film): 3340(w), 1730(s), 1602(w), 1495(m), 1250(s), 1195(s), 1110 (s), 835(s), 777(s), 700(s) cm$^{-1}$; $^1$H-NMR δ: 7.38–7.17(m, 5H), 4.46(d, J=5.1 Hz, 1H), 3.60–3.40(m, 2H), 3.50(s, 3H), 3.06(ddd, J=10.3, 5.1, 5.1 Hz, 1H), 2.87(dd, J=12.6, 4.0 Hz, 1H), 2.65(dd, J=12.6, 8.8 Hz, 1H), 2.13–1.95(m, 1H), 1.95–1.73(m, 1H), 1.65(br.s, 2H), 0.87(s, 9H), 0.031(s, 3H), 0.027(s, 3H) ppm.

(11) (2R*,3S*,5S*)-1-Benzyloxycarbonyl-5-(tert-butyldimethylsilyloxy)methyl-3-methoxycarbonyl-2-phenylpiperidine To a stirred and ice-cooled mixture of (2R*,3S*,5S*)-5-(tert-butyldimethylsilyloxy)methyl-3-methoxycarbonyl-2-phenylpiperidine (11.46 g, 31.52 mmol), NaHCO$_3$ (3.97 g, 47.3 mmol), H$_2$O (80.0 ml), and THF (10.0 ml) was added a solution of benzyl chloroformate (Cbz-Cl, 5.92 g, 34.67 mmol) in THF (15.0 ml). A precipitated gummy material was dispersed by adding AcOEt (40.0 ml). After the resultant milky suspension was stirred with ice-cooling for 2.5 hours, the organic layer was separated from the mixture, and the aqueous layer was extracted with AcOEt (40 ml×4). The combined organic layer and AcOEt extracts were washed with sat. NaCl aq. solution (×1), dried (MgSO$_4$), and concentrated in vacuo to give a yellow oil (16.56 g). This was flash chromatographed over Sir (Merck Kieselgel 60, 200 g). Elution with n-hexane-AcOEt (60:1/30:1/20:1) gave title compound (13.88 g, 88.5%) as a pale yellow oil. IR$_{max}$ (film): 1735(s), 1700(s), 1498(m), 1290(s), 1253(s), 1100(s), 775(s), 740(m), 700(s) cm$^{-1}$; $^1$H-NMR δ: 7.42–7.28(m, 6H), 7.28–7.16(m, 4H), 5.98–5.87(m, 1H), 5.31–5.10(m, 2H), 3.92(dm, J=13.6 Hz, 1H), 3.63(dd, J=10.1, 9.7 Hz, 1H), 3.60(s, 3H), 3.53(dd, J=10.1, 7.9 Hz, 1H), 3.09(ddd, J=11.2, 5.6, 5.6 Hz, 1H), 3.12–2.95(m, 1H), 2.24–2.06(m, 1H), 2.06–1.93(m, 1H), 0.87(s, 9H), 0.02(s, 6H) ppm.

(12) (2R*,3S*,5S*)-1-Benzyloxycarbonyl-5-(tert-butyldimethylsilyloxy)methyl-3-carbamoyl-2-phenylpiperidine Under an atmosphere of N$_2$, a 2.0M solution of Me$_3$Al in PhMe (Aldrich, 140 ml, 280 mmol) was added dropwise to a stirred and ice-cooled suspension of NH$_4$Cl (14.92 g, 279 mmol) in dry PhMe (280 ml). After the addition was complete, the reaction mixture was allowed to stirr at room temperature for 30 minutes; at this point, solid NH$_4$Cl disappeared completely, and the clear, homogeneous mixture resulted. To this was added a solution of (2R*,3S*,5S*)-1-benzyloxycarbonyl-5-(tert-butyldimethylsilyloxy) methyl-3-methoxycarbonyl-2-phenylpiperidine (13.88 g, 27.89 mmol) in dry PhMe (30.0 ml) dropwise at room temperature: on the addition, the reaction mixture became turbid. This was stirred and heated at a bath temperature of 50 C. overnight (ca. 20 hours). The turbid white reaction mixture was ice-cooled; and H$_2$O (80.0 ml, 4.40 mol) was added carefully, wherein H$_2$ gas evolved violently. The resultant white precipitates were filtered off by the aid of Celite, and washed with AcOEt (80 ml×5). The combined filtrate and AcOEt washings were washed with sat. NaCl aq. solution (×2), dried (MgSO$_4$), and concentrated in vacuo to give a viscous colorless oil (13.76 g). This was flash chromatographed over SiO$_2$ (Merck Kieselgel 60, 100 g). Elution with n-hexane-AcOEt (5:1/2:1/1:1) gave title compound (11.10 g, 82.4%) as a colorless syrup. IR$_{max}$ (film): 3405(s), 3340(s), 3200(s), 3100(w), 3070(m), 3045(m), 1735(m), 1675(br., v.s), 1610(s), 1498(s), 1160(s), 1100(s), 836(s), 775(s), 737(s) cm$^{-1}$; $^1$H-NMR δ: 7.42–7.18(m, 10H), 5.83(d, J=5.1 Hz, 1H), 5.67(br.s, 1H), 5.47(br.s, 1H), 5.20(d, J=12.5 Hz, 1H), 5.13(d, J=12.5 Hz, 1H), 3.91(br.d, J=13.9 Hz, 1H), 3.63(dd, J=10.0, 6.8 Hz, 1H), 3.53(dd, J=10.0, 7.7 Hz, 1H), 3.08(dd,J=13.9, 7.7 Hz, 1H), 2.98(ddd, J=17.6, 5.1, 4.8 Hz, 1H), 2.25–1.91(m, 3H), 0.87(s, 9H), 0.02(s, 6H) ppm.

(13) (2S*,3S*,5S*)-1-Benzyloxycarbonyl-3-(N-tert-butoxycarbonyl)amino-5-(tert-butyldimethylsilyloxy) methyl-2-phenylpiperidine A mixture of (2R*,3S*,5S*)-1-benzyloxycarbonyl-5-(tert-butyldimethylsilyloxy)methyl-3-carbamoyl-2-phenylpiperidine (11.1 g, 23.0 mmol) and tert-BuOH (200 ml) was stirred and heated to a bath temperature of 80 C. To the resultant homogeneous mixture was added Pb(OAc)$_4$ (17.3 g, 39.1 mmol) in one portion at that temperature. On the addition, the reaction mixture became yellow brown, and this was stirred and heated at reflux for 45 minutes. After cooling to room temperature, the mixture was neutralized with sat. NaHCO$_3$ aq. solution (ca. 200 ml) with occasional ice-cooling. The dark brown precipitates were filtered off by the aid of Celite, and washed with AcOEt. The combined filtrate and AcOEt washings were concentrated in vacuo to give an aqueous residue, from which white solids precipitated in the course of the concentration. This residue was extracted with AcOEt (60 ml×4). The combined AcOEt extracts were washed with sat. NaCl aq. solution (×1), dried (MgSO$_4$), and concentrated in vacuo to give a viscous colorless oil (14.18 g). This was crystallized from n-hexane (ca. 30 ml)-AcOEt (ca. 2 ml) to give title compound (11.42 g, 89.5%) as white powders. The mother liquor concentrated in vacuo (1.02 g) was purified by SiO$_2$ flash chromatography [Merck Kieselgel 60, 15.0 g; n-hexane-AcOEt (30:1/20:1)] to give an additional amount of title compound (0.68 g, 5.3%); a total yield: 12.10 g (94.8%). mp 119.0–119.5 C. (white powders); IR$_{max}$ (nujol): 3330(s), 1700(s), 1685(s), 1520(s), 1248(s), 1160(s), 1118(s), 858(s), 840(s), 780(s), 770(s), 763(s), 738(m), 710(s), 698(m) cm$^{-1}$; $^1$H-NMR δ: 7.41–7.20(m, 10H), 7.100(br.s, 1H), 5.35(br.d, J=5.9 Hz, 1H), 5.13(br.s, 0.6H), 5.08(br.s, 0.4H), 5.01(br.s, 0.7H), 4.96(br.s, 0.3H), 4.28–4.05(m, 2H), 3.93–3.80(m, 1H), 3.73–3.55(m, 3H), 2.3–2.16(m, 1H), 1.77–1.60(m, 1H), 1.40 (br.s, 7.5H), 0.88(br.s, 10.5H), 0.05(s, 3H), 0.04(s, 3H) ppm.

(14) (2S*,3S*,5S*)-1-Benzyloxycarbonyl-3-(N-tert-butoxycarbonyl)amino-5-hydroxymethyl-2-phenylpiperidine To a stirred and ice-cooled suspension of (2S*,3S*,5S*)-1-benzyloxycarbonyl-3-(N-tert-butoxycarbonyl)amino-5-(tert-butyldimethylsilyloxy)methyl-2-phenylpiperidine (12.10 g, 21.81 mmol) and molecular sieves 4A (MS 4A, activated powder, Aldrich; 15.0 g) in dry THF (100 ml) was added a 1.0M solution of (n-Bu)$_4$NF in THF (Aldrich, 26.2 ml, 26.2 mmol) dropwise. After the addition was complete, the reaction mixture was allowed to stir at room temperature for 1.5 hours. The zeolite was filtered off by the aid of Celite, and washed with THF. To the combined filtrate and washings was added H$_2$O (50.0 ml), and the mixture was neutralized with 1.0M AcOH aq. solution (1.0 ml). The solvent THF was evaporated in vacuo, and the aqueous residue was extracted with CH$_2$Cl$_2$ (40 ml×4). The combined CH$_2$Cl$_2$ extracts were washed with sat. NaHCO$_3$ aq. solution (×1), H$_2$O (×2), and sat. NaCl aq. solution (×1), dried (MgSO$_4$), and concentrated in vacuo to give a pale orange solid (12.82 g). This was flash chromatographed over SiO$_2$ (Merck Kieselgel 60, 120 g). Elution with CHCl$_2$—MeOH (300:1/150:1) gave a white solid (7.81 g), which was recrystallized from AcOEt-n-hexane to give title compound (7.05 g, 73.4%) as a white powder. From the pale yellow mother liquor (0.16 g) was recovered an additional amount of title compound (0.08 g, 0.83%); a total yield: 7.13 g (74.3%). mp 121.0–124.0 C. (white powders); IR$_{max}$(nujol): 3300(s), 1712(s), 1699(s), 1671(s), 1538(s), 1498(w), 1263 (s), 1170(s), 1050(s), 738(m), 699(s) cm$^{-1}$; $^1$H-NMR δ: 7.43–7.24(m, 10H), 7.28–7.13(m, 1H), 5.48(br. d, J=5.5 Hz, 1H), 5.20(d, J=12.5 Hz, 1H), 5.03(br.d, J=12.5 Hz, 1H), 4.31–4.13(m, 1H), 3.99(br.dd, J=14.5, 4.1 Hz, 1H), 3.75–3.58(m, 2H), 3.36(br.dd, J=14.5, 4.6 Hz, 1H), 2.88–2.11(m, 2H), 1.97–1.75(m, 2H), 1.39(s, 9H) ppm.

(15) (2S*,3S*,5S*)-1-Benzyloxycarbonyl-3-(N-tert-butoxycarbonyl)amino-5-formyl-2-phenylpiperidine To a stirred and ice-cooled solution of (2S*,3S*,5S*)-1-benzyloxycarbonyl-3-(N-tert-butoxycarbonyl)amino-5-hydroxymethyl-2-phenylpiperidine(2.50 g, 5.68 mmol) and Et$_3$N (3.55 ml, d0.726, 25.5 mmol) in DMSO (25.0 ml) was added SO$_3$ pyridine (4.06 g, 25.5 mmol) portionwise. The resultant orange mixture was stirred at room temperature for 45 minutes, and then poured into ice-water (50 ml). The mixture was extracted with CH$_2$Cl$_2$ (30 ml×4). The combined CH$_2$Cl$_2$ extracts were washed with 10% citric acid aq. solution (×2), H$_2$O (×1), sat. NaHCO$_3$ aq. solution (×1), and sat. NaCl aq. solution (×1), dried (MgSO$_4$), and concentrated in vacuo to give crude title compound (2.80 g, quantitative) as a pale yellow solid. This was employed in the next step without further purification. A portion of it (0.112 g) was recrystallized from AcOEt—Et$_2$O to give an analytical sample of title compound (0.051 g). mp 125.0–127.0 C. (white powders); IR$_{max}$ (nujol): 3300(s), 1720(shoulder, s), 1710(v.s), 1698(shoulder, s), 1538(s), 1500(m), 1170(s), 773(m), 738(s), 700(s) cm$^{-1}$; $^1$H-NMR δ: 9.79(br.s, 0.6H), 9.73(br.s, 0.4H), 7.50–7.20(m, 10H), 7.22 (br.s, 1H), 5.04–4.92(m, 1H), 5.17(br.d, J=12.1 Hz, 1H), 5.11–4.98(m, 1H), 4.68–4.54(m, 0.6H), 4.54–4.39(m, 0.4H), 4.30–3.95(m, 2H), 3.60–3.45(m, 0.6H), 3.38–3.15(m, 0.4H), 2.90–2.67(m, 1H), 2.52–2.39(m, 0.6H), 2.34–2.21(m, 0.4H), 1.41(br.s, 9H) ppm.

(16) (2S*,3S*,5S*)-1-Benzyloxycarbonyl-3-(N-tert-butoxycarbonyl)amino-5-methoxycarbonyl-2-phenylpiperidine To a stirred and ice-cooled suspension of crude (2S*,3S*,5S*)-1-benzyloxycarbonyl-3-(N-ten-butoxycarbonyl)amino-5-formyl-2-phenylpiperidine (2.80 g, 5.86 mmol) in THF (3.0 ml) and MeOH—H$_2$O (9:1, 10.0 ml) was added solid NaHCO$_3$ (17.2 g, 205.1 mmol). To this suspension was added a 2.0M stock solution of Br$_2$ in MeOH—H$_2$O (9:1, 20.5 ml, 41.0 mmol) dropwise with ice-cooling. After the addition was complete, the deep red reaction mixture was allowed to stir at room temperature for 5 hours. The orange red mixture was ice-cooled, and solid Na$_2$S$_2$O$_3$ was added portionwise with stirring until the red color of the excess Br$_2$ was discharged. The inorganic precipitates were filtered off by the aid of Celite, and washed with CH$_2$Cl$_2$. The combined filtrate and CH$_2$Cl$_2$ washings were concentrated in vacuo. To the residue was added H$_2$O, and the mixture was extracted with AcOEt—CH$_2$Cl$_2$ (4:1). The combined AcOEt—CH$_2$Cl$_2$ (4:1) extracts were washed with sat. NaHCO$_3$ aq. solution (×1), and sat. NaCl aq. (×1), dried (MgSO$_4$), and concentrated in vacuo to give a yellow solid (2.03 g). This was flash chromatographed over SiO$_2$ (Merck Kieselgel 60, 35 g). Elution with CH$_2$Cl$_2$—MeOH (30:1) gave a white solid (1.19 g), which was recrystallized from AcOEt-n-hexane to afford title compound (1.01 g, overall 36.7% from (2S*,3S*,5S*)-1-benzyloxycarbonyl-3-(N-tert-butoxycarbonyl)amino-5-hydroxymethyl-2-phenylpiperidine in two steps). mp 128.0–129.0 C. (white fine needles); IR$_{max}$ (nujol): 3320(s), 1735(s), 1710(v.s), 1700(v.s), 1673(v.s), 1583(s), 1498(m), 1250(s), 1175(s), 1110(s), 770(m), 738(s), 700(s) cm$^{-1}$; $^1$H-NMR δ: 7.50–7.10 (m, 10H), 7.18(br.s, 1H), 5.47(br.d, J=5.9 Hz, 1H), 5.18(d, J=12.5 Hz, 1H), 4.99(d, J=12.5 Hz, 1H), 4.56–4.33(m, 1H), 4.36–4.05(m, 1H), 3.69(s, 3H), 3.65–3.40(m, 1H), 2.99–2.86(m, 1H), 2.42–2.25(m, 1H), 1.96–1.80(m, 1H), 1.41(br.s, 9H), ppm.

(17) (2S*,3S*,5S*)-3-Amino-1-benzyloxycarbonyl-5-methoxycarbonyl-2-phenylpiperidine A suspension of (2S*,3S*,5S*)-1-benzyloxycarbonyl-3-(N-tert-butoxycarbonyl)amino-5-methoxycarbonyl-2-phenylpiperidine (1.01 g, 2.16 mmol) in Hydrogen Chloride, Methanol Reagent 10 (20.0 ml) was stirred and heated at reflux for 10 minutes; the reaction mixture became homogeneous with evolution of CO$_2$ gas. This mixture was concentrated in vacuo, and the syrupy residue was basified with sat. Na$_2$CO$_3$ aq. solution. The mixture was extracted with CH$_2$Cl$_2$ (×4). The combined CH$_2$Cl$_2$ extracts were dried (Na$_2$SO$_4$), and concentrated in vacuo to give crude title compound (0.789 g, quantitative) as a pale yellow syrup. IR$_{max}$ (film): 3375(m), 3310(w), 1730(br., s), 1700(br., s), 1603(m), 1585(m), 1497(s), 1122(s), 740(s), 700(s) cm$^{-1}$; $^1$H-NMR δ: 7.45–7.15(m, 10H), 5.26(d, J=5.9 Hz, 1H), 5.15(d, J=12.5 Hz, 1H), 5.01(d, J=12.5 Hz, 1H), 4.51(dd, J=13.9, 2.1 Hz, 1H), 3.65(s, 3H), 3.56–3.43(m, 1H), 3.54 (dd, J=13.9, 4.2 Hz, 1H), 2.95–2.85(m, 1H), 2.22(ddd, J=14.9, 4.0, 4.0 Hz, 1H), 1.95(ddd, J=14.9, 10.9, 6.6 Hz, 1H) ppm.

(18) (2S*,3S*,5S*)-1-Benzyloxycarbonyl-5-methoxycarbonyl-3-[N-(2-methoxy-5-trifluoromethoxybenzyl)amino]-2-phenylpiperidine To a stirred solution of (2S*,3S*,5S*)-3-amino-1-benzyloxycarbonyl-5-methoxycarbonyl-2-phenylpiperidine (0.79 g, 2.16 mmol) and 2-methoxy-5-trifluoromethoxybenzaldehyde (0.59 g, 2.70 mmol) in CH₂Cl₂ (25.0 ml) was added NaB(OAc)₃H (0.69 g, 3.24 mmol) potionwise at room temperature. The turbid reaction mixture was stirred at room temperature for 3 hours; the NaB(OAc)₃H added dissolved gradually with stirring, and the turbidity of the reaction mixture decreased. sat. Na₂CO₃ aq. solution was added, and from the mixture was separated the CH₂C₂ layer. The aqueous layer was extracted with CH₂Cl₂. The combined CH₂Cl₂ layer and extracts were dried (Na₂SO₄), and concentrated in vacuo to give a pale yellow oil (1.55 g). This was flash chromatographed over SiO₂ (Merck Kieselgel 60, 32.0 g). Elution with CH₂Cl₂—MeOH (300:1/200:1) gave title compound (1.15 g, 93.1%) as a colorless syrup, which crystallized spontaneously on standing in a refrigerator. This was recrystallized from (i-Pr)₂O to give analytically pure title compound (1.058 g, 85.3%). mp 93.5–95.0 C. (fine colorless needles); IR$_{max}$ (nujol): 1730(s), 1700(s), 1610(w), 1498(s), 1220(s), 1147 (s), 1110(s), 1080(s), 1055(s), 1028(s), 742(s), 730(s), 703 (s), 695(s) cm⁻¹; ¹H-NMR δ: 7.43–7.23(m, 9H), 7.21(br.s, 1H), 7.09–7.00(m, 2H), 6.73(d, J=9.2 Hz, 1H), 5.39(br.d, J=5.3 Hz, 1H), 5.16(d, J=12.5 Hz, 1H), 5.02(d, J=12.5 Hz, 1H), 4.50(dd, J=13.7, 1.8 Hz, 1H), 3.79(d, J=13.9 Hz, 1H), 3.68(d, J=13.9 Hz, 1H), 3.63(s, 3H), 3.54(dd, J=13.7, 5.5 Hz, 1H), 3.28(ddd, J=10.2, 5.5 4.8 Hz, 1H), 2.89–2.28(m, 1H), 2.24–2.01(m, 1H), 1.54(br.s, 2H) ppm.

(19) (2S*,3S*,5S*)-5-Methoxycarbonyl-3-[N-(2-methoxy-5-trifluoromethoxybenzyl)amino]-2-phenylpiperidine A mixture of (2S*,3S*,5S*)-1-benzyloxycarbonyl-5-methoxycarbonyl-3-[N-(2-methoxy-5-trifluoromethoxybenzyl)amino]-2-phenylpiperidine (1.007 g, 1.758 mmol) and 20% Pd(OH)₂/C (0.258 g), THF (5.0 ml), and MeOH (30.0 ml) was stirred under an atmosphere of H₂ (baloon) at room temperature for an hour. The catalyst was filtered off by the aid of Celite, and washed with THF. The combined filtrate and THF washings were concentrated in vacuo to give title compound (0.789 g, quantitatively) as a pale yellow oil. IR$_{max}$ (film): 3340(s), 1735(s), 1718(s), 1608(m), 1250(br., s), 1150(br., s), 1033(s), 810(m), 750(m), 700(m) cm⁻¹; ¹H-NMR δ: 7.36–7.18(m, 5H), 7.00(dd, J=9.2, 2.2 Hz, 1H), 6.84(d, J=2.2 Hz, 1H), 6.62(d, J=9.2 Hz, 1H), 3.89(d, J=2.2 Hz, 1H), 3.71(s, 3H), 3.68(d, J=14.3 Hz, 1H), 3.51(ddd, J=11.9, 3.7, 1.8 Hz, 1H), 3.47(s, 3H), 3.40(d, J=14.3 Hz, 1H), 3.05(dddd, J=12.3, 11.9, 3.7, 3.7 Hz, 1H), 2.92–2.82(m, 1H), 2.88(dd, J=11.9, 11.9 Hz, 1H), 2.37(dm, J=13.6 Hz, 1H), 1.78(ddd, J=13.6, 12.3, 2.9 Hz, 1H), 1.68 (br.s, 2H, NH×2) ppm.

(20) (2S*3S*,5S*)-5-Methoxycarbonyl-3-[N-(2-methoxy-5-trifluoromethoxybenzyl)amino]-2-phenylpiperidine dihydrochloride To a solution of (2S*,3S*,5S*)-5-methoxycarbonyl-3-[N-(2-methoxy-5-trifluoromethoxybenzyl)amino]-2-phenylpiperidine (0.856 g, 1.952 mmol) in MeOH (2.0 ml) was added an excess amount of Hydrogen Chloride, Methanol Reagent 10 (Tokyo Kasei, >1.60 ml) until the mixture became sufficiently acidic (pH<2); in the course of the addition, precipitation of a white solid took place. After Et₂O (1.5 ml) was added, the heterogeneous yellow mixture was left to stand in a refrigerator overnight. The white solids precipitated were collected by filtration, washed with i-PrOH-(i-Pr)₂O (2:1), and dried in vacuo with heating at 50 C. to give title dihydrochloride (0.933 g, 93.6%) as white powders. mp 217.8–218.3 C.; IR$_{max}$ (nujol): 3230–2150(br., s), 1748(s), 1620(w), 1580(m), 1557(m), 1502(s), 1272(s), 1238(s), 1210(s), 1173(s), 1152(s), 1130(s), 1030(s), 858 (m), 810(m), 770(m), 752(m), 700(s), 687(m) cm³¹ ¹; ¹H-NMR δ (DMSO-d₆): 7.69–7.58(m, 2H), 7.57–7.42(m, 3H), 7.38–7.26(m, 2H), 7.02(br.d, J=8.8 Hz, 1H), 4.93(br.s, 1H), 4.10–3.80(m, 1H), 3.87(br.d, J=12.84 Hz, 1H), 3.71(s, 3H), 3.70(br.s, 2H), 3.68–3.60(m, 1H), 3.60–3.05(m, 8H), 2.63(br.d, J=12.8 Hz, 1H), 2.19(br.dd, J=12.8, 12.8 Hz, 1H) ppm.

(21) (2S*,3S*5S*)-5-Carboxy-3-[N-(2-methoxy-5-trifluoromethoxybenzyl)amino]-2-phenylpiperidine dihydrochloride To a suspension of (2S*,3S*,5S*)-5-methoxycarbonyl-3-[N-(2-methoxy-5-trifluoromethoxybenzyl)amino]-2-phenylpiperidine dihydrochloride (0.197 g, 0.385 mmol) in MeOH (6.0 ml) was added 6M HCl aq. solution (8.0 ml), and the mixture was stirred and heated at a gentle reflux for an hour; the mixture became homogeneous with heating. After conc. HCl (7.0 ml) was added, the stirring was continued with heating at reflux for additional two hours. The mixture was cooled to room temperature, and acetone was added. After the mixture was ice-cooled, the white solids precipitated were collected by filtration, washed with acetone, dried in vacuo with heating at 60 C. overnight to give title hydrochloride (0.138 g, 71.8%) as white plates.

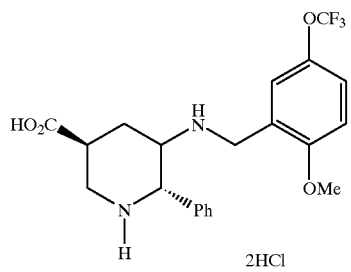

mp 207.8–211.8 C.; IR$_{max}$ (nujol): 3270–2200(br., s), 1760 (s), 1745(s), 1580(w), 1550(m), 1500(s), 1253(s), 1238(s), 1210(s), 1180(s), 1157(s), 1125(m), 1026(m), 810(m), 759 (m), 723(m), 700(s), 680(w) cm⁻¹;
¹H-NMR δ (DMSO-d₆): 7.69–7.55(m, 2H), 7.56–7.40(m, 3H), 7.37–7.24(m, 2H), 7.00(br.d, J=8.4 Hz, 1H), 4.88(br.s, 1H), 4.00–3.75(m, 1H), 3.85(br.d, J=13.9 Hz, 1H), 3.71(s, 3H), 3.69–3.55(m, 1H), 3.67(br.s, 2H), 3.57–3.10(m, 6H), 2.69–2.50)m, 1H), 2.26–2.04(m,1H) ppm.

(22) (2S*,3S*,5S*)-3-Amino-1-benzyloxycarbonyl-5-hydroxymethyl-2-phenylpiperidine A suspension of (2S*,3S*,5S*)1-benzyloxycarbonyl-3-(N-tert-butoxycarbonyl)amino-5-hydroxymethyl-2-phenylpiperidine (0.60 g, 1.36 mmol) in Hydrogen Chloride, Methanol Reagent 10 (Tokyo Kasei, 10.0 ml) was stirred and heated at reflux for 15 minutes; the reaction mixture became homogeneous with heating. The mixture was, then, concentrated in vacuo. The pale yellow syrupy residue was basified with sat. Na₂CO₃ aq. solution. The mixture was extracted with CH₂Cl₂. The combined CH₂Cl₂ extracts were dried (Na₂SO₄), and concentrated in vacuo to give crude title compound (0.500 g, quantitative) as a red oil. IR$_{max}$ (film): 3380(s), 3300(s), 1700(s), 1683(s), 1603(w), 1585(w), 1495 (m), 1130(m), 1077(m), 1048(m), 740(m), 698(s) cm⁻¹; ¹H-NMR δ: 7.43–7.13(m, 10H), 5.20(d, J=5.9 Hz, 1H), 5.16(d,,J=12.6 Hz, 1H), 5.04(d, J=12.6 Hz, 1H), 4.04(dd, J=13.9, 2.0 Hz, 1H), 3.60(d, J=7.0 Hz, 2H), 3.49(dd, J=13.9, 4.6 Hz, 1H), 3.54–3.33(m, 1H), 2.25–2.10(m, 1H), 1.92 (ddd, J=13.9, 9.9, 7.3 Hz, 1H), 1.65(ddd, J=13.9, 4.8, 4.5 Hz, 1H), 1.65–1.26(m, 3H) ppm. This was employed in the next step without further purification.

(23) (2S*,3S*,5S*)-1-Benzyloxycarbonyl-5-hydroxymethyl-3-[N-(2-methoxy-5-trifluoromethoxybenzyl)amino]-2-phenylpiperidine To a stirred solution of (2S*,3S*,5S*)-3-amino-1-benzyloxycarbonyl-5-hydroxymethyl-2-phenylpiperidine (0.50 g, 1.36 mmol)) and 2-methoxy-5-trifluoromethoxybenzaldehyde (0.37 g, 1.70 mmol) in CH$_2$Cl$_2$ (20.0 ml) was added NaB(OAc)$_3$H (0.43 g, 2.04 mmol) portionwise. The reaction mixture was stirred at room temperature for 3 hours, and then basified with sat. Na$_2$CO$_3$ aq. solution. The mixture was extracted with CH$_2$Cl$_2$. The combined extracts were dried (Na$_2$SO$_4$), and concentrated in vacuo to give a red oil (0.90 g), which solidified spontaneously on standing in a refrigerator (4 C.). This was flash chromatographed over SiO$_2$ (Merck Kieselgel 60, 18.0 g). Elution with CH$_2$Cl$_2$—MeOH (300:1/200:1/100:1) gave title compound (0.678 g, 91.6%) as a colorless syrup. IR$_{max}$ (film): 3450(s), 1698(s), 1682(s), 1670(s), 1498(s), 1230(br., s), 1160(br., s), 1030(s), 738(s), 700(s) cm$^{-1}$; $^1$H-NMR δ: 7.44–7.21(m, 9H), 7.18(br.s, 1H), 7.04 (br.d, J=8.8 Hz, 1H), 7.00(br.s, 1H), 6.92(d, J=8.8 Hz, 1H), 5.40–5.27(m, 1H), 5.17(d, J=121.5 Hz, 1H), 5.05(d, J=12.5 Hz, 1H), 4.03(br.d, J=13.9 Hz, 1H), 3.74(d, J=13.9 Hz, 1H), 3.70–3.41(m, 4H), 3.62(s, 3H), 3.23–3.11(m, 1H), 2.20–1.95(m, 2H), 1.70–1.45(m, 3H) ppm.

(24) (2S*,3S*,5S*)-5-Hydroxymethyl-3-[N-(2-methoxy-5-trifluoromethoxybenzyl)amino]-2-phenylpiperidine To a solution of (2S*,3S*,5S*)-1-benzyloxycarbonyl-5-hydroxymethyl-3-[-N-(2-methoxy-5-trifluoromethoxybenzyl)amino]-2-phenylpiperidine (0.545 g, 1.00 mmol) and HCO$_2$NH$_4$ (0.252 g, 4.00 mmol) in MeOH (15.0 ml) was added 20% Pd(OH)$_2$/C (0.159 g) in one portion. The mixture was stirred and heated at reflux for 30 minutes. The catalyst was filtered off by the aid of Celite, and washed with MeOH. The combined filtrate and washings were concentrated in vacuo to give a yellow syrupy residue, which was basified with IM NaOH aq. solution. The mixture was extracted CH$_2$Cl$_2$, and the combined CH$_2$Cl$_2$ extracts were dried (Na$_2$SO$_4$), and concentrated in vacuo to give a pale yellow oil (0.419 g). This was flash chromatographed over SiO$_2$ (Merck Kieselgel 60, 4.0 g). Elution with CH$_2$Cl$_2$—MeOH (30:1/20:1) gave title compound (0.380 g, 92.7%) as a yellow oil. IR$_{max}$ (film): 3320(br., s), 1608(m), 1498(s), 1487(s), 1230(br., s), 1160(br., s), 1030(s), 810(m), 740(m), 700(s) cm$^{-1}$; $^1$H-NMR δ: 7.40–7.20(m, 5H), 6.99 (dd, J=8.8, 2.9 Hz, 1H), 6.85(d, J=2.9 Hz, 1H), 6.63(d, J=8.8 Hz, 1H), 3.86(d, J=2.2 Hz, 1H), 3.64(d, J=14.5 Hz, 1H), 3.60–3.47(m, 2H), 3.50(s, 3H), 3.46–3.36(m, 1H), 3.38(d, J=14.5 Hz, 1H), 2.92–2.84(m, 1H), 2.54(dd, J=1.5, 11.5 Hz, 1H), 2.28–2.10(m, 1H), 2.12(dm, J=12.9 Hz, 1H), 1.69(br.s, 3H; NH×2+OH), 1.35(ddd, J=12.9, 12.9, 2.8 Hz, 1H) ppm.

(25) (2S*,3S*,5S*)-5-Hydroxymethyl-3-[N-(2-methoxy-5-trifluoromethoxybenzyl)amino]-2-phenylpiperidine dihydrochloride To a solution of (2S*,3S*,5S*)-5-hydroxymethyl-3-[N-(2-methoxy-5-trifluoromethoxybenzyl)amino]-2-phenylpiperidine (0.455 g, 1.11 mmol) in i-PrOH was added Hydrogen Chloride, Methanol Reagent 10 (Tokyo Kasei), until the mixture became acidic (pH 2). The volatiles were evaporated in vacuo. The yellow syrupy residue was crystallized from (i-Pr)$_2$O. After the mixture was left to stand in a refrigerator (at 4 C.) overnight, the white crystals were collected by filtration, washed #with (i-Pr)$_2$O, and dried in vacuo to give title hydrochloride (0.460 g, 86.0%). An additional amount (0.021 g, 3.9%) of title hydrochloride was obtained as a second crop; a total yield: 0.481 g (89.9%). mp 188.0–192.0 C. (white powders); IR$_{max}$ (nujol): 3450(s), 3250–2320(br., s), 1580(m), 1555(s), 1502(s), 1260(s), 1213 (s), 1030(s), 817(m), 755(s), 700(s) cm$^{-1}$; $^1$H-NMR δ (DMSO-d$_6$): 7.75–7.62(m, 2H), 7.58–7.41(m, 3H), 7.40–7.30(m,2H), 7.03(d, J=9.5 Hz, 1H), 4.89(br.s, 1H), 4.10–3.79(m, 2H), 3.70(br.s, 3H), 3.57–3.10(m, 9H), 2.97 (br.dd, J=11.6, 11.6 Hz, 1H), 2.60–2.40(m, 1H), 2.35–2.17 (m, 1H), 2.00–1.78(m, 1H) ppm.

(26) (2R*,3S*,5R*)-1-Benzyloxycarbonyl-5-(tert-butyldimethylsilyloxy)methyl-3-methoxycarbonyl-2-phenylpiperidine To a stirred and ice-cooled mixture of (2R*,3S*,5R*)-5-(tert-butyldimethylsilyloxy)methyl-3-methoxycarbonyl-2-phenylpiperidine (4.86 g, 13.4 mmol), NaHCO$_3$ (1.68 g, 20.1 mmol), THF (5.0 ml), and H$_2$O (30.0 ml) was added Cbz-Cl (2.51 g, 14.7 mmol), and the mixture was stirred with ice-cooling for 30 minutes. The mixture was extracted with AcOEt (40.0 ml×3). The combined AcOEt extracts were washed with sat. NaCl aq. solution (×1), dried (MgSO$_4$), and concentrated in vacuo to give a viscous pale yellow oil (6.82 g). This was flash chromatographed over SiO$_2$ (Merck Kieselgel 60, 80.0 g). Elution with n-hexane-AcOEt (30:1/20: 1) gave title compound (6.51 g, 97.9%) as a viscous colorless oil. IR$_{max}$ (film): 1735(s), 1700(s), 1605 (w), 1585(w), 1495(m), 1250(s), 1115(s), 775(s), 740(m), 700(s) cm$^{-1}$; $^1$H-NMR δ: 7.45–7.31(m, 4H), 7.31–7.15(m, 6H), 6.05(d, J=5.5 Hz, 0.6H), 5.87(d, J=5.5 Hz, 0.4H), 5.32–5.10(5.30, 5.25, 5.21, 5.18, and 5.13; m, 2H), 4.20–4.05(m, 1H), 3.65–3.45(m, 2.4H), 3.60(br.s, 3H), 3.40 (dd, J=9.9, 6.6 Hz, 0.6H), 3.08–2.91(m, 1H), 2.63(dd, J=11.7, 11.7 Hz, 0.4H), 2.52(dd, J=13.6, 11.7 Hz, 0.6H), 2.11–1.98(m, 1H), 1.98–1.70(m, 2H), 0.86(s, 3.6H), 0.83(s, 5.4H), 0.026, 0.018, and 0.008(each s, total 6H) ppm.

(27) (2R*,3S*,5R*)-1-Benzyloxycarbonyl-5-(tert-butyldimethylsilyloxy)-methyl-3-carbamoyl-2-phenylpiperidine Under an atmosphere of N$_2$, a 2.0M solution of Me$_3$Al in hexanes (Aldrich, 66.0 ml, 132 mmol) was added dropwise to a stirred and ice-cooled suspension of NH$_4$Cl (7.00 g, 131 mmol) in dry PhMe (130.0 ml). After the addition was complete, the reaction mixture was allowed to stirr at room temperature. At the point when evolution of H$_2$ gas ceased, the mixture became gelatinous. Dry PhMe (20.0 ml) was added, and the stirring was continued at room temperature for 30 minutes. To this white slurry was added dropwise a solution of (2R*,3S*,5R*)-1-benzyloxycarbonyl-5-(tert-butyldimethylsilyloxy)methyl-3-methoxycarbonyl-2-phenylpiperidine (6.51 g, 13.1 mmol) in dry PhMe (20.0 ml). The reaction mixture was stirred and heated at a bath temperature of 50 C. overnight (ca. 21 hours); the mixture became homogeneous with stirring, and then turbid again. The mixture was ice-cooled, and H$_2$O (40.0 ml) was added carefully. The resultant gelatinous white mixture was filtered through a pad Celite, and the filter cake was washed with AcOEt (80 ml×4). The combined filtrate and AcOEt washings were washed with sat. NaCl aq. solution (×2), dried (MgSO$_4$), and concentrated in vacuo to give a viscous colorless oil (6.56 g), which crystallized spontaneously on standing at room temperature. These solids were recrystallized from AcOEt-n-hexane to give title compound (4.75 g, 75.25). The recovered pale yellow mother liquor (1.16 g) was purified by flash chromatography [SiO$_2$, Merck Kieselgel 60, 15.0 g; n-hexane-AcOEt (8:1/5:1/1:1)] to give an additional amount (0.44 g, 7.0%) of title compound; a total yield:5.19 g (82.1%). mp 120.0–122.5 C. (fine colorless needles); IR$_{max}$ (nujol): 3390(s), 3180(m), 1673(v.s), 1630 (shoulder, m), 1500(w), 1162(s), 1100(s), 838(s), 773(m), 735(m), 695(s) cm$^{-1}$; $^1$H-NMR δ: 7.55–7.21(m, 10H), 5.91 (d, J=5.1 Hz, 0.7H), 5.84(br.s, 0.7H), 5.79(d, J=4.8 Hz, 0.3H), 5.42(br.s, 1.3H), 5.34(d, J=12.5 Hz, 0.3H), 5.24(d, J=12.2 Hz, 0.7H), 5.19(d, J=12.2 Hz, 0.7H), 5.13(d, J=12.5 Hz, 0.3H), 4.24–4.04(m, 1H), 3.57(dd, J=9.9, 4.4 Hz, 1.3H), 3.39(dd, J=10.3, 6.6 Hz, 0.7H), 3.00–2.85(m, 1H), 2.77(dd, J=13.2, 10.6 Hz, 0.3H), 2.53(dd, J=13.6, 11.4 Hz, 0.7H), 2.10–1.70(m, 3H), 0.87(s, 3H), 0.83(3, 6H), 0.03(s, 2H), 0.01(s, 4H) ppm.

(28) (2S*,3S*,5R*)-1-Benzyloxycarbonyl-3-(N-tert-butoxycarbonyl)amino-5-(tert-butyldimethylsilyloxy)methyl-2-phenylpiperidine Solid (2R*,3S*,5R*)-1-benzyloxycarbonyl-5-(tert-butyldimethylsilyloxy)methyl-3-carbamoyl-2-phenylpiperidine (5.19 g, 10.8 mmol) was dissolved in tert-BuOH (100 ml) by heating to a bath temperature of 70 C. To the resultant homogeneous mixture was added Pb(OAc)$_4$ (90%, 8.10 g, 18.3 mmol) in one portion. The red reaction mixture was stirred and heated at reflux for 45 minutes. The dark brown mixture was ice-cooled, and then neutralized with sat. NaHCO$_3$ aq. solution (ca. 90 ml). The inorganic dark brown precipitates were filtered off by the aid of Celite, and washed with AcOEt. The combined filtrate and AcOEt washings were concentrated in vacuo, and the aqueous residue was extracted with AcOEt (50.0 ml×4). The combined AcOEt extracts were washed with sat. NaCl aq. solution (×1), dried (MgSO$_4$), and concentrated in vacuo to give crude title compound (6.35 g, quantitative) as a viscous pale yellow oil. IR$_{max}$ (film): 3450(shoulder, m), 3350(s), 1718(v.s), 1700(v.s), 1682(v.s), 1250(s), 1165(s), 1110(s), 838(s), 778(s), 700(s) cm$^{-1}$; $^1$H-NMR δ: 7.51–7.19(m, 10H), 7.13(br.s, 1H), 5.59–5.37(m, 1H), 5.19, and 5.14 (each br.s, total 1H), 5.11–4.94(m, 1H), 4.26–4.00(m, 2H), 3.71–3.46(m, 2H), 3.26–3.00)m, 1H), 2.06–1.70(m, 2H), 1.40(br.s, 9H), 0.91(br.s, 9H), 0.05(br.s, 6H) ppm. This was employed in the next step without further purification.

(29) (2S*,3S*,5R*)-1-Benzyloxycarbonyl-3-(N-tert-butoxycarbonyl)amino-5-hydroxymethyl-2-phenylpiperidine To a stirred and ice-cooled solution of (2S*,3S*,5R*)-1-benzyloxycarbonyl-3-(N-tert-butoxycarbonyl)amino-5-(tert-butyldimethylsilyloxy)methyl-2-phenylpiperidine (6.35 g, 10.8 mmol) in dry THF (45.0 ml) was added a 1.0M solution of (n-Bu)$_4$NF in THF (Aldrich, 13.0 ml, 13.0 mmol) dropwise. After the resultant orange reaction mixture was stirred at room temperature for an hour, MS 4A (activated powder, Aldrich; 8.0 g) was added. The stirring was continued at room temperature for an additional hour. The zeolite was filtered off by the aid of Celite, and washed with THF. The combined filtrate and THF washings were adjusted to neutral with 1.0M AcOH aq. solution and sat. NaHCO$_3$ aq. solution. The mixture was concentrated in vacuo, and the aqueous residue was extracted with CH$_2$Cl$_2$ (20.0 ml×4). The combined CH$_2$Cl$_2$ extracts were washed with sat. NaCl aq. solution (×1), dried (MgSO$_4$), and concentrated in vacuo to give an orange oil (7.47 g). This was flash chromatographed over SiO$_2$ (Merck Kieselgel 60, 75.0 g). Elution with CH$_2$Cl$_2$—MeOH (200:1/150:1/100:1) gave a white solid (4.71 g), which was recrystallized from AcOEt-n-hexane to give title compound [4.11 g, overall 86.5% from (2R*,3S*,5R*)-1-benzyloxycarbonyl-5-(tert-butyldimethylsilyloxy)methyl-3-carbamoyl-2-phenylpiperidine in two steps] as white powders. mp 132.0–134.0 C.; IR$_{max}$ (nujol): 3485(s), 3303(s), 1690 (shoulder, v.s), 1675(v.s), 1605(w), 1538(v.s), 1500(m), 1288(s), 1170(s), 1075(s), 733(s), 700(s) cm$^{-1}$; $^1$H-NMR δ: 7.48–7.20(m, 10H), 7.16(br.s, 1H), 5.48(br.s, 1H), 5.17(br.s, 0.25H), 5.13(br.s, 0.75H), 5.05(br.s, 0.75H), 5.00(br.s, 0.25H), 4.37–4.00(m, 2H), 3.73–3.56(m, 2H), 3.03(dd, J=12.8, 12.8 Hz, 1H), 2.10–1.90(m, 1H), 2.05–1.82(m, 1H), 1.68–1.47(m, 2H), 1.40(br.s, 9H) ppm.

(30) (2S*,3S*,5R*)-1-Benzyloxycarbonyl-3-(N-tertbutoxycarbonyl)amino-5-formyl-2-phenylpiperidine To a stirred and ice-cooled solution of (2S*,3S*,5R*)-1-benzyloxycarbonyl-3-(N-tert-butoxycarbonyl)amino-5-hydroxymethyl-2-phenylpiperidine (0.50 g, 1.14 mmol), and Et$_3$N (0.71 ml, d0.726, 5.11 ml) in DMSO (8.0 ml) was added S03 pyridine (0.81 g, 5.11 mol) portionwise. After the addition was complete, the reaction mixture was stirred at room temperature for an hour. The mixture was poured into ice-water (10.0 ml), and the mixture was extracted with CH$_2$Cl$_2$ (×5). The combined CH$_2$Cl$_2$ extracts were washed with 10% citric acid aq. solution (×3), H$_2$O (×1), sat. NaHCO$_3$ aq. solution (×1), and sat. NaCl aq. solution (×1), dried (MgSO$_4$), and concentrated in vacuo to give title compound (0.535 g, quantitative) as a white solid. This was employed in the next step without further purification. A portion of it (0.063 g) was recrystallized from AcOEt-n-hexane to give an analytical sample of title compound (0.044 g). mp 124.0–125.0 C. (white powders); IR$_{max}$ (nujol): 3300(s), 1720(shoulder, s), 1710(v.s), 1695(v.s), 1675(v.s), 1605(w), 1537(s), 1500(m), 1288(s), 1170(s), 1072(s), 773 (m), 736(s), 698(s) cm$^{-1}$; $^1$H-NMR δ: 9.79(s, 0.12H), 9.73(s, 0.88H), 7.40–7.15(m, 11H), 5.50(br.d, J=5.5 Hz, 0.88H), 5.46(br.d, J=5.5 Hz, 0.12H), 5.17(d, J=12.5 Hz, 1H), 5.04(d, J=12.5 Hz, 1H), 4.60(dm, J=14.1 Hz, 0.12H), 4.45(dm, J=14.1 Hz, 0.88H), 4.32–3.90(m, 1H), 3.21(dd, J=13.9, 11.7 Hz, 1H), 2.90–2.68(m, 1H), 2.45(dm, J=12.7 Hz, 0.12H), 2.27(dm, J=12.7 Hz, 0.88H), 1.80(ddd, J=12.7, 12.7, 12.7 Hz, 1H), 1.41(br.s, 9H) ppm.

(31) (2S*,3S*,5R*)-1-Benzyloxycarbonyl-3-(N-tert-butoxycarbonyl)amino-5-methoxycarbonyl-2-phenylpiperidine To a stirred and ice-cooled mixture of (2S*,3S*,5R*)-1-benzyloxycarbonyl-3-(N-tert-butoxycarbonyl)amino-5-formyl-2-phenylpiperidine (0.45 g, 1.03 mmol), NaHCO$_3$ (3.35 g, 39.9 mmol), THF (3.0 ml), and MeOH-H$_2$O (9:1, 12.0 ml) was added dropwise a 2.0M stock solution of Br$_2$ in MeOH—H$_2$O (9:1, 3.99 ml. 7.98 mmol). After the resultant red orange reaction mixture was stirred at room temperature for 2 hours and 35 minutes, the mixture was ice-cooled, and then solid Na$_2$S$_2$O$_3$ was added to discharge the orange color of the excess Br$_2$. The inorganic precipitates were filtered off by the aid of Celite, and washed with CH$_2$Cl$_2$. The combined filtrate and CH$_2$Cl$_2$ washings were concentrated in vacuo. The residue was diluted with H$_2$O, and extracted with CH$_2$Cl$_2$. The combined CH$_2$Cl$_2$ extracts were dried (MgSO$_4$), and concentrated in vacuo to give a white solid (0.52 g). This was flash chromatographed over SiO$_2$ (Merck Kieselgel 60, 13.0 g). Elution with CH$_2$Cl$_2$—AcOEt (150:1/100:1) gave title compound (0.34 g, 70.8%) as a white solid. A portion of it was recrystallized from AcOEt-n-hexane to give an analytically pure sample of the title compound as fine white needles. mp 128.0–129.0 C.; IR$_{max}$ (nujol): 3420(s), 3310(m), 1738(v.s), 1700(v.s), 1672 (v.s), 1610(w), 1590(w), 1515(m), 1510(v.s), 1220(v.s), 1170(s), 1153(s), 775(s), 755(s), 710(s), 700(s) cm$^{-1}$; $^1$H-NMR δ: 7.48–7.15(m, 11H), 5.56–5.41(m, 1H), 5.16(d, J=12.6 Hz, 1H), 5.04 (d, J=12.6 Hz, 1H), 4.50–4.00(m, 2H), 3.72(s, 3H), 3.26(dd, J=13.6, 12.5 Hz, 1H), 2.80–2.70(m, 1H), 2.30–2.15(m,1H), 1.89(ddd, J=12.7, 12.7, 12,7 Hz, 1H), 1.40(br.s, 9H) ppm.

(32) (2S*,3S*,5R*)-3-Amino-1-benzyloxycarbonyl-5-methoxycarbonyl-2-phenylpiperidine A suspension of (2S*,3S*,5R*)-1-benzyloxycarbonyl-3-(N-tert-butoxycarbonyl)amino-5-methoxycarbonyl-2-phenylpiperidine (1.11 g, 2.37 mmol) in Hydrogen Chloride, Methanol Reagent 10 (Tokyo Kasei; 20.0 ml) was stirred and heated at reflux for 30 minutes; violent evolution of CO$_2$ gas took place with heating, and the reaction mixture became homogeneous. The reaction mixture was, then, concentrated in vacuo to give a solid residue, which was basified with sat. $Na_2CO_3$ aq. solution. The mixture was extracted with $CH_2Cl_2$, and the combined $CH_2Cl_2$ extracts were dried ($Na_2SO_4$), and concentrated in vacuo to give crude title compound (0.777 g, 89.0%) as a viscous pale yellow oil. $IR_{max}$ (film): 3380(m), 3315(w), 1735(s), 1720 (s), 1700(s), 1685(s), 1603(m), 1584(m), 1497(s), 1200(s), 765(s), 750(s), 740(s), 700(s) cm$^{-1}$; $^1$H-NMR δ: 7.58–7.16 (m, 10H), 5.45–5.23(m, 1H), 5.20–5.04(m, 2H), 4.55–4.26 (m, 1H), 3.73(s, 3H), 3.36–3.22(m, 2H), 2.83–2.65(m, 1H), 2.20–2.02)m, 1H), 1.97(ddd, J=12.5, 12.5, 12.5 Hz, 1H), 1.43(br.s, 2H) ppm. This was employed in the next step without further purification.

(33) (2S*,3S*,5R*)-1-Benzyloxycarbonyl-5-methoxycarbonyl-3-[N-(2-methoxy-5-trifluoromethoxybenzyl)amino]-2-phenylpiperidine To a stirred solution of (2S*,3S*,5R*)-3-amino-1-benzyloxycarbonyl-5-methoxycarbonyl-2-phenylpiperidine (0.84 g, 2.28 mmol) and 2-methoxy-5-trifluoromethoxybenzaldehyde (0.63 g, 2.85 mmol) in $CH_2Cl_2$ (18.0 ml) was added $NaB(OAc)_3H$ (0.73 g, 3.42 mmol) potionwise at room temperature. After the turbid reactin mixture was stirred vigorously at room temperature for 4 hours, sat. $Na_2CO_3$ aq. solution (15.0 ml) was added to make the mixture to be basic (pH10–11). The $CH_2Cl_2$ layer was separated from the mixture, and the aqueous layer was extracted with $CH_2Cl_2$ (×4). The combined $CH_2Cl$ layer and extracts were dried ($Na_2SO_4$), and concentrated in vacuo to give a viscous pale yellow oil (1.49 g). This was chromatographed over $SiO_2$ (Merck Kieselgel 60, 30.0 g). Elution with $CH_2Cl_2$—MeOH (300:1/250:1) gave title compound (1.26 g, 96.2%) as a viscous colorless oil. IR $v_{max}$ (film): 3450(w), 3330(w), 1740(shoulder, s), 1735(s), 1703(s), 1700(s), 1687(s), 1610(w), 1497(s), 1160(br., s), 1030(s), 815(m), 765(s), 740(s), 700(s) cm$^{-1}$; $^1$H-NMR δ: 7.65–7.50 (m, 1H), 7.52–7.38(m, 1H), 7.40–7.11(m, 8H), 7.2–6.96(m, 2H), 6.74(br.d, J=8.8 Hz, 1H), 5.45–5.34(m, 0.5H), 5.20–5.00(m, 2H), 5.17–5.05(m, 0.5H), 4.49–4.33(m, 0.5H), 4.35–4.17(m, 0.5H), 3.90–3.53(m, 2H), 3.69(br.s, 6H), 3.20 (br.dd, J=13.2, 13.2 Hz, 1H), 3.20–3.00(m, 1H), 2.83–2.60 (m, 1H), 2.26–1.99(m,2H), 1.52(br.s, 1H) ppm.

(34) (2S*,3S*,5R*)-5-Methoxycarbonyl-3-[N-2-methoxy-5-trifluoromethoxybenzyl)amino]-2-phenylpiperidine A mixture of (2S*,3S*,5R*)-1-benzyloxycarbonyl-5-methoxycarbonyl-3-[N-(2-methoxy-5-trifluoromethoxybenzyl)amino]-2-phenylpiperidine (1.26 g, 2.20 mmol) and 20% $Pd(OH)_2$/C (0.30 g) in MeOH (20.0 ml) was stirred at room temperature under an atmosphere of $H_2$ (baloon) for 5.5 hours. An additional amount (0.20 g) of 20% $Pd(OH)_2$/C was added, and the stirring was continued under an atmosphere of $H_2$ (baloon) for an hour. The catalyst was filtered off by the aid of Celite, and washed with $CH_2Cl_2$. The combined filtrate and washings were concentrated in vacuo. The yellow oily residue was diluted with $CH_2Cl_2$, washed with sat. $Na_2CO_3$ aq. solution (×1), dried ($Na_2SO_4$), and concentrated in vacuo to give a viscous yellow oil (1.00 g). This was chromatographed over $SiO_2$ (Merck Kieselgel 60, 10.0 g). Elution with $CH_2Cl_2$—MeOH (250:1/50:1) gave title compound (0.873 g, 90.6%) as a viscous yellow oil. $IR_{max}$ (film): 3320(m), 1735(s), 1720(s), 1605(m), 1508(s), 1498(s), 1490(s), 1133(s), 810(s), 762(s), 741(s), 700(s) cm$^{-1}$; $^1$H-NMR δ: 7.33–7.18(m, 4H), 7.17–7.10(m,1H), 7.01(dd, J=9.2, 2.6 Hz, 1H), 6.87(d, J=2.6 Hz, 1H), 6.60(d, J=9.2 Hz, 1H), 3.94(d, J=1.7 Hz, 1H), 3.77(ddd, J=13.6, 1.9, 1.9 Hz, 1H), 3.94(d, J=1.7 Hz, 1H), 3.77(ddd, J=13.6, 1.9, 1.9 Hz, 1H), 3.66(s, 3H), 3.65(d, J=13.9 Hz, 1H), 3.39(d, 13.9 Hz, 1H), 3.36(s, 3H), 2.88(dd, J=13.6, 3.7 Hz, 1H), 2.84–2.73(m, 2H), 2.37–2.29(m, 1H), 1.95(ddd, J=15.0, 5.5, 3.3 Hz, 1H), 1.68(br.s, 2H) ppm.

(35) (2S*,3S*,5R*)-5-Methoxycarbonyl-3-[N-(2-methoxy-5-trifluoromethoxybenzyl)amino]-2-phenylpiperidine fumarate To a solution of (2S*,3S*,5R*)-5-methoxycarbonyl-3-[N-(2-methoxy- 5-trifluoromethoxybenzyl)amino]-2-phenylpiperidine (0.194 g, 0.443 mmol) in EtOH (3.0 ml) was added fumaric acid (0.103 g, 0.886 mmol) in one portion. An additional volume of EtOH was added with heating at reflux until the mixture became homogeneous. The resultant clear solution was left to stand at room temperature, wherein recrystallization took place. After $Et_2O$ (0.50 ml) was added, the mixture was kept in a refrigerator. The white solids precipitated were collected by filtration, washed with $Et_2O$ (×1), and dried in vacuo with heating at 50 C. to give title fumarate salt (0.197 g, 80.1%) as colorless fine needles. mp 176.7–176.9 C.; $IR_{max}$ (nujol): 3200–2100(br., s), 1749(s), 1704(s), 1693(s), 1655(w), 1643 (w), 1548(s), 1500(m), 1268(s), 1253(s), 1208(s), 1182(s), 1158(s), 990(s), 750(s), 700(s) cm$^{-1}$; $^1$H-NMR δ (DMSO-$d_6$): 7.40–7.16(m, 5H), 7.15(dd, J=8.8, 2.6 Hz, 1H), 6.94(d, J=2.6 Hz, 1H), 6.87(d, J=8.8 Hz, 1H), 6.58(s, 2H), 4.07–3.97 (m, 1H), 4.00–3.25(m, 8H) 3.56(s, 3H), 3.44(s, 3H), 2.91–2, 80(m, 1H), 2.79–2.71(m, 1H), 2.66–2.54(m, 1H), 2.01–1.87 (m, 1H) ppm.

(36) (2S*,3S*,5R*)-5-Carboxy-3-[N-(2-methoxy-5-trifluoromethoxybenzyl)amino]-2-phenylpiperidine dihydrochloride A mixture of (2S*,3S*,5R*)-5-methoxycarbonyl-3-[N-(2-methoxy-5-trifluoro-methoxybenzyl)amino]-2-phenylpiperidine (0.241 g, 0.551 mmol) in conc. HCl (3.0 ml) was stirred and heated are reflux for 30 minutes. After cooling to room temperature, the dark orange mixture was filtered through a short pad of Celite to remove a black precipitate. The filtrate was concentrated in vacuo. The syrupy dark red residue was dissolved in acetone. After (i-Pr)$_2$O was added, the mixture was subjected to sonication to induce crystallization. The mixture was left to stand in a refrigerator (at 4 C.) overnight. The solids precipitated were collected by filtration, washed with $Et_2O$, and dried in vacuo with heating at 50 C. to give the title dihydrochloride salt (0.103 g, 37.6%). The combined filtrate and $Et_2O$ washings were concentrated in vacuo, and the dark red syrupy residue was crystallized from i-PrOH-(i-Pr)$_2$O to give an additional amount (0.041 g) of the title dihydrochloride salt; a total yield: 0.144 g (52.5%).

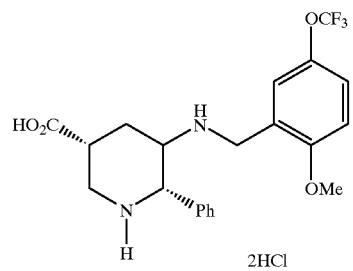

mp 179.9–182.9 C. (colorless short prisms); $IR_{max}$ (nujol): 3250–2100(br., s), 1758(w), 1720(s), 1502(s), 1255(s) cm$^{-1}$; $^1$H-NMR δ (DMSO-$d_6$): 7.83–7.65(m, 2H), 7.64–7.77(m, 3H), 7.43–7.29(m, 2H), 7.15–6.98(m, 1H), 5.17–4.88(m, 1H), 4.15–3.80(m, 2H), 3.75–3.60(m, 5H), 3.62–3.05(m, 7H), 2.77–2.20(m, 2H) ppm.

(37) (2S*,3S*,5R*)-3-Amino-1-benzyloxycarbonyl-5-hydroxymethyl-2-phenylpiperidine To a stirred solution of (2S*,3S*,5R*)-1-benzyloxycarbonyl-3-(N-tert-butoxycarbonyl)amino-5-hydroxymethyl-2-phenylpiperidine (0.50 g, 1.14 mmol) in AcOEt (10.0 ml) was added conc. HCl (5.0 ml) dropwise with occasional ice-cooling. After stirring at room temperature for 40 minutes, the mixture was concentrated in vacuo to give a yellow syrupy residue, which was, then, basified to pH 10 with 1M NaOH aq. solution. The mixture was extracted with $CH_2Cl_2$, and the combined $CH_2Cl_2$ extracts were dried ($K_2CO_3$), and concentrated in vacuo to give crude title compound (0.405 g, quantitative) as a pale yellow syrup. $IR_{max}$ (film): 3360(s), 3300(s), 1693(shoulder, v.s), 1685(v.s), 1603(m), 1585(m), 1497(s), 1263(s), 1150(s), 1070(s), 760(s), 739(s), 700(s) cm$^{-1}$; $^1$H-NMR δ: 5.42–5.19 (m, 1H), 5.16–5.00)m, 2H), 4.35–4.14(m, 1H), 3.70–3.53 (m, 2H), 3.38–3.25(m, 1H), 3.04(dd, J=13.2, 12.5Hz, 1H), 2.15–1.94(m, 1H), 1.86(ddd, J=13.2, 4.8, 4.2 Hz, 1H), 1.75–1.35(m, 4H) ppm. This was employed in the next step without further purification.

(38) (2S*,3S*,5R*)-1-Benzyloxycarbonyl-5-hydroxymethyl-3-[N-(2-methoxy-5-trifluoromethoxybenzyl)amino]-2-phenylpiperidine To a stirred solution of (2S*,3S*,5R*)-3-amino-1-benzyloxycarbonyl-5-hydroxymethyl-2-phenylpiperidine (0.405 g, 1.14 mmol) and 3-methoxy-5-trifluoromethoxybenzaldehyde (0.301 g, 1.71 mmol) in dry $CH_2Cl_2$ (25.0 ml) was added $NaB(OAc)_3H$ (0.362 g, 1.71 mmol) portionwise. The mixture was sonicated to dissolve the $NaB(OAc)_3H$ added, and then stirred at room temperature for 2 hours and 40 minutes. To this was added sat. $Na_2CO_3$ aq. solution (12.0 ml), and the $CH_2Cl_2$ layer was separated. The aqueous layer was extracted with $CH_2Cl_2$. The combined $CH_2Cl_2$ layer and extracts were dried ($K_2CO_3$), and concentrated in vacuo to give a pale yellow oil (0.72 g). This was flash chromatographed over $SiO_2$ (Merch Kieselgel 60, 14.0 g). Elution with $CH_2Cl_2$—MeOH (300:1/ 200:1/100:1) gave title compound [0.416 g, overall 67.0% from (2S*,3S*,5R*)-1-benzyloxycarbonyl-3-(N-tert-butoxy-carbonyl)amino-5-hydroxymethyl-2-phenylpiperidine in two steps] as a colorless syrup. $IR_{max}$ (film): 3450(s), 1700(s), 1682(s), 1670(s), 1652(s), 1610(w), 1497(s), 1490(s), 1260(br., s), 1220(br., s), 1152(br., s), 1030(s), 738(s), 700(s) cm$^{-1}$; $^1$H-NMR δ: 7.50–7.11(m, 10H), 7.13–6.93(m, 1H), 6.69(br.d, J=8.4 Hz, 1H), 5.60–5.22(m, 1H), 5.20–4.95(m, 2H), 4.36–4.10(m, 1H), 3.79(d, J=13.9 Hz, 1H), 3.65–3.45(m, 3H), 3.59(br.s, 3H), 3.23–2.95(m, 2H), 2.15(br.s, 1H), 2.02–1.86(m, 1H), 1.86–1.68(m, 1H), 1.68–1.45)m, 2H) ppm.

(39) (2S*,3S*,5R*)-5-Hydroxymethyl-3-[N-(2-methoxy-5-trifluoromethoxybenzyl)amino]-2-phenylpiperidine A mixture of (2S*,3S*,5R*)-1-benzyloxycarbonyl-5-hydroxymethyl-3-[N-(2-methoxy-5-trifluoromethoxybenzyl)-amino]-2-phenylpiperidine (0.416 g, 0.76 mmol), 20% $Pd(OH)_2$/C (0.11 g), and MeOH (10.0 ml) was stirred at room temperature under an atmosphere of $H_2$ (baloon) for 90 minutes. An additional amount of 20% $Pd(OH)_2$/C (0.08 g) was added, and the stirring was continued under an atmosphere of $H_2$ (baloon) for 45 minutes. The catalyst was filtered off by the aid of Celite, and washed with MeOH. The combined filtrate and washings were concentrated in vacuo to give a yellow semi-solid (0.309 g). This was dissolved in MeOH (3.0 ml) again, and the mixture was basified with 1M NaOH aq. solution. The solvent MeOH was evaporated in vacuo, and the aqueous residue was extracted with $CH_2Cl_2$. The combined $CH_2Cl_2$ extracts were dried ($K_2CO_3$), and concentrated in vacuo to give title compound (0.298 g, 95.5%) as a yellow syrup. $IR_{max}$ (film): 3310(s), 3070(br.s,), 1605(w), 1498(s), 1250(s), 1150(s), 1035(s), 756(s), 700(s) cm$^{-1}$; $^1$H-NMR δ: 7.34–7.16(m, 4H), 7.15–7.03(m, 2H), 6.85(d, J=2.6 Hz, 1H), 6.62(d, J=8.8 Hz, 1H), 3.92(d, J=2.6 Hz, 1H), 3.91–3.71(m, 3H), 3.45(d, J=11.4 Hz, 1H), 3.40(d, J=11.4 Hz, 1H), 3.35(s, 3H), 3.1 (ddd, J=13.6, 4.8, 1.5 Hz, 1H), 2.72(ddd, J=2.9, 2.9, 2.6 Hz, 1H), 2.25–2.07(m, 2H), 1.85(br.s, 3H; OH+NH×2), 1.75–1.65(m, 1H), ppm.

(40) (2S*,3S*,5R*)-5-Hydroxymethyl-3-[N-(2-methoxy-5-trifluoromethoxybenzyl)amino]-2-phenylpiperidine difumarate To a solution of (2S*,3S*,5R*)-5-hydroxymethyl-3-[N-(2-methoxy-5-trifluoromethoxybenzyl)amino]-2-phenylpiperidine (0.298 g, 0.726 mmol) in EtOH (3.0 ml) was added fumaric acid (0.169 g, 1.45 mmol) in one portion. An additional volume of EtOH was added with heating at reflux, until the mixture became homogeneous. After the resultant pale yellow solution was allowed to cool to room temperature, (i-Pr)$_2$O (2.0 ml) was added. After the mixture was left to stand in a refrigerator (at 4 C.) overnight, and then the precipitated white solids were collected by filtration, washed with (i-Pr)$_2$O-i-PrOH, and dried in vacuo with heating at 50 C. to give title difumarete (0.382 g, 82.1%) as white powders.

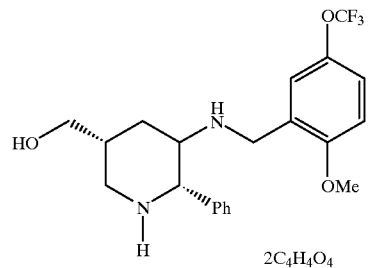

mp 162.0–165.0 C.; $IR_{max}$ (nujol): 2565(br., s), 17179s), 1705(s), 1641(s), 1630(s), 1561(s), 1502(s), 1280(s), 1250 (s), 1162(s), 973(s), 790(m), 751(s), 648(s) cm$^{-1}$; $^1$H-NMR δ (DMSO-d$_6$): 7.45–7.33(m, 4H), 7.22–7.12(m, 1H), 7.18–7.11(m, 2H), 6.91(d, J=8.8 Hz, 1H), 6.54(s, 4H), 4.29(br.s, 1H), 3.88–3.13(m, 13H), 3.56(s, 3H, 3.06–2.96(m, 1H), 2.90–2.83(m, 1H), 2.07–1.95(m, 1H), 1.93–1.80(m, 1H) ppm.

We claim:

1. A compound of the chemical formula (I) and its pharmaceutically acceptable salt:

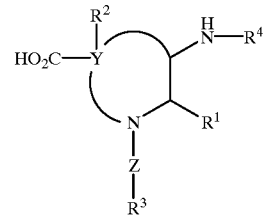

wherein

Y is $C_3$ alkylene;

Z is a valence bond or $C_1$–$C_6$ alkylene;

R$^1$ is phenyl, biphenyl, indanyl, naphthyl, thienyl, furyl, pyridyl, thiazolyl, isothiazolyl, oxazolyl, isoxazolyl, tetrazolyl, quinolyl, phenyl $C_1$–$C_6$ alkyl- or benzhydryl, wherein each of the ring moieties may optionally be substituted by one or more substituents independently selected from halogen, $C_1$–$C_6$ alkyl, halosubstituted $C_1$–$C_6$ alkyl, $C_1$–$C_6$ alkoxy and halosubstituted $C_1$–$C_6$ alkoxy;

$R^2$ is hydrogen or $C_1$–$C_6$ alkyl;

$R^3$ is hydrogen, hydroxy, cyano, amino or carboxy; and $R^4$ represents a group of the formula (II) or (III)

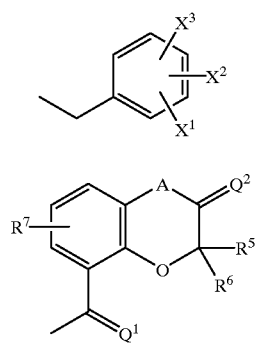

wherein
$X^1$, $X^2$ and $X^3$ are each halo, hydrogen, nitro, $C_1$–$C_6$ alkyl, halosubstituted $C_1$–$C_6$ alkyl, $C_1$–$C_6$ alkoxy, halosubstituted $C_1$–$C_6$ alkoxy, hydroxy, amino, $C_1$–$C_6$ alkylthio, $C_1$–$C_6$ alkylsulfinyl or $C_1$–$C_6$ alkylsulfonyl;

$Q^1$ and $Q^2$ are each $H_2$, oxygen or sulfur;

A is valence bond, methylene, oxygen, sulfur or NH;

$R^5$ and $R^6$ are each hydrogen or $C_1$–$C_6$ alkyl; and $R^7$ is hydrogen, halogen, $C_1$–$C_6$ alkyl, halosubstituted $C_1$–$C_6$ alkyl or $C_1$–$C_6$ alkoxy;

provided that when Z is a valence bond, $R_3$ must be hydrogen.

2. A compound according to claim 1, wherein $R^4$ is the formula (II).

3. A compound according to claim 2, wherein Y is propylene.

4. A compound according to claim 3, wherein —$ZR^3$ is hydrogen.

5. A compound according to claim 4, wherein $R^1$ is phenyl.

6. A compound according to claim 5, wherein $R^2$ is attached to the carbon atom adjacent to the nitrogen of $NZR^3$.

7. A compound according to claim 6 selected from

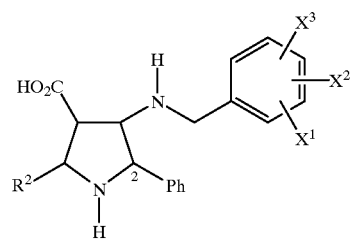

and

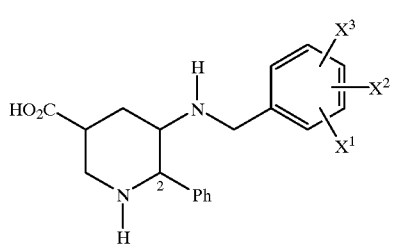

wherein in the compound (Ia) the stereochemistry is (2S*,3S*,4R*,5R*) or (2S*,3S*,4S*) and in the compound (Ib) the stereochemistry is (2S*,3S*,5S*).

8. A compound according to claim 7, wherein $X^1$ is 2-methoxy.

9. A compound according to claim 8, wherein $X^2$ is hydrogen and $X^3$ is ($C_1$–$C_6$) alkyl or trifluoro ($C_1$–$C_6$) alkoxy.

10. A compound selected from the following:

(2S*,3S*,4S*,5R*)-4-Carboxy-3-[N-(5-Isopropyl-2-methoxy-benzyl)amino]-5-methyl-2-phenylpyrrolidine and (2S*,3S*,5S*)-5-Carboxy-3-[N-(2-methoxy-5-trifluoromethoxybenzyl)amino]-2-phenylpiperidine.

11. A pharmaceutical composition for the treatment of gastrointestinal pain, migraine or emesis in a mammalian subject, which comprises a therapeutically effective amount of a compound of claim 1 or its pharmaceutically acceptable salt together with a pharmaceutically acceptable carrier.

12. A method of treating gastrointestinal disorders, central nervous system disorders, allergy, inflammatory diseases, asthma, pain, migraine or emesis in a mammalian subject, which comprises administering to the said subject a therapeutically effective amount of a compound of claim 1 or its pharmaceutically acceptable salt.

* * * * *